US012721857B2

(12) United States Patent
Scorei et al.

(10) Patent No.: US 12,721,857 B2
(45) Date of Patent: Sep. 1, 2026

(54) BORATE COMPLEXES OF CHLOROGENIC ACID AND USES THEREOF

(71) Applicant: P.L. Thomas & Co., Inc., Morristown, NJ (US)

(72) Inventors: Ion Romulus Scorei, Morristown, NJ (US); Andrei Bita, Morristown, NJ (US); Laura Dinca, Morristown, NJ (US); George Dan Mogosanu, Morristown, NJ (US); Nagendra Rangavajla, Morristown, NJ (US)

(73) Assignee: P.L. Thomas & Co., Inc., Morristown, NJ (US)

( * ) Notice: Subject to any disclaimer, the term of this patent is extended or adjusted under 35 U.S.C. 154(b) by 0 days.

(21) Appl. No.: 18/703,647

(22) PCT Filed: Oct. 21, 2022

(86) PCT No.: PCT/US2022/078488
§ 371 (c)(1),
(2) Date: Apr. 22, 2024

(87) PCT Pub. No.: WO2023/070074
PCT Pub. Date: Apr. 27, 2023

(65) Prior Publication Data
US 2024/0325418 A1 Oct. 3, 2024

Related U.S. Application Data

(60) Provisional application No. 63/326,931, filed on Apr. 4, 2022, provisional application No. 63/271,159, filed on Oct. 24, 2021.

(51) Int. Cl.
*A61K 31/69* (2006.01)
*A23F 5/02* (2006.01)
(Continued)

(52) U.S. Cl.
CPC ................ *A61K 31/69* (2013.01); *A23F 5/02* (2013.01); *A61K 36/742* (2024.05); *A61K 45/06* (2013.01);
(Continued)

(58) Field of Classification Search
CPC ...... A23F 5/02; A61P 1/12; A61P 1/14; A61P 3/00; A61P 3/10; A61P 1/00; A61P 43/00; G01N 33/50
See application file for complete search history.

(56) References Cited

U.S. PATENT DOCUMENTS 659,416 A 10/1900 Perry
5,962,049 A 10/1999 Milijkovic
(Continued)

FOREIGN PATENT DOCUMENTS

CN 112457051 A 3/2021
CN 112457501 A 3/2021
(Continued)

OTHER PUBLICATIONS

Bell et al., Boric Acid Complexes of Phenolic Acids, Polyhedron, 1991, 10(6), pp. 613-618 (Year: 1991).*
(Continued)

*Primary Examiner* — Renee Claytor
*Assistant Examiner* — Andrew P Lee
(74) *Attorney, Agent, or Firm* — KRAMER & AMADO, P.C.

(57) ABSTRACT

A borate diester of chlorogenic acid is prepared by reacting a solution comprising chlorogenic acid and boric acid in a ratio of at least 2:1 in a superheated water solvent or an aqueous acetonitrile solvent. If aqueous acetonitrile is used as a solvent, the acetonitrile solvent is evaporated to leave a water solution. A product containing the desired borate diester is obtained by freeze-drying or air-drying the water
(Continued)

solution. Insufficient levels of boron in a microbiome in a subject in need thereof may be treated by administering the borate diester of chlorogenic acid to the subject.

19 Claims, 14 Drawing Sheets

(51) Int. Cl.

| | |
|---|---|
| *A61K 36/74* | (2006.01) |
| *A61K 45/06* | (2006.01) |
| *A61P 1/12* | (2006.01) |
| *A61P 1/14* | (2006.01) |
| *G01N 33/50* | (2006.01) |

(52) U.S. Cl.

CPC *A61P 1/12* (2018.01); *A61P 1/14* (2018.01); *G01N 33/50* (2013.01); *A61K 2236/333* (2013.01)

(56) References Cited

U.S. PATENT DOCUMENTS

| | | | |
|---|---|---|---|
| 6,569,416 | B1 | 5/2003 | Laub |
| 6,576,229 | B2 | 6/2003 | Laub |
| 2010/0311827 | A1 | 12/2010 | Daneshtalab |
| 2013/0131165 | A1 | 5/2013 | Sugiyama |
| 2015/0041083 | A1 | 2/2015 | Yoshikawa et al. |
| 2018/0318323 | A1 | 11/2018 | Roman |
| 2020/0023021 | A1 | 1/2020 | Lewis |
| 2021/0290717 | A1 | 9/2021 | Doering |

FOREIGN PATENT DOCUMENTS

| | | | |
|---|---|---|---|
| EP | 1555885 | B1 | 8/2013 |
| JP | 7140503 | B2 | 9/2022 |
| WO | 2009/132888 | A1 | 11/2009 |
| WO | 2013/094393 | A1 | 6/2013 |
| WO | 2018230032 | A1 | 12/2018 |
| WO | 2020/152673 | A1 | 7/2020 |
| WO | 2020/193752 | A1 | 10/2020 |

OTHER PUBLICATIONS

Colin F. Bell, et al., "Boric Acid Complexes of Phenolic Acids," Polyhedron vol. 10, No. 6, pp. 613-681, 1991.

Xin Chen, et al., "Structural Identification of a Bacterial Quorum-Sensing Signal Containing Boron," Nature, vol. 415, Jan. 31, 2002, pp. 545-549.

Jiali Chen, et al., "Changes of Porcine Gut Microbiota in Response to Dietary Chlorogenic Acid Supplementation," Applied Microbiology and Biotechnology, Aug. 10, 2019, https://doi.org/10.1007/s00253-0019-10025-8.

Dai Cheng, et al., "Chlorogenic Acid Relieves Lead-Induced Cognitive Impairments and Hepato-Renal Damage via Regulating the Dysbiosis of the Gut Microbiota in Mice," Food & Function, the Royal Society of Chemistry, 2019, DOI: 10.1039/c8fo01755g.

M.-P. Gonthier, et al., "Microbial Metabolism of Caffeic Acid and Its Esters Chlorogenic and Caftaric Acids by Human Faecal Microbiota In Vitro," Biomedicine & Pharmacotherapy, vol. 60, 2006, pp. 536-540, Aug. 31, 2006.

Daniel Hernandez-Patlan, et al., "Evaluation of the Antimicrobial and Intestinal Integrity Properties of Boric Acid in Broiler Chickens Infected with *Salmonella enteritidis*: Proof of Concept," Research in Veterinary Science, vol. 123, Apr. 2019, pp. 7-13.

Sofia Moco, et al., "Metabolomics View on Gut Microbiome Modulation by Polyphenol-rich Foods," J. Proteome Res., vol. 11, 2012, pp. 4781-4790, dx.doi.org/10.1021/pr300581s.

Olivier Mortele, et al., "Chlorogenic Acid as a Model Compound for Optimization of an In Vitro Gut Microbiome-Metabolism Model," Proceedings, vol. 11, 31, 2019, doi: 10.3390/proceedings2019011031.

W. Mullen, et al., "The Antioxidant and Chlorogenic Acid Profiles of Whole Coffee Fruits are Influenced by the Extraction Procedures," Journal of Agricultural and Food Chemistry, 59, 2011, pp. 3754-3762, dx.doi.org/10.1021/jf200122m.

Kazuchika Nishitsuji, et al., "Effect of coffee or coffee components on gut microbiome and short-chain fatty acids in a mouse model of metabolic syndrome," Scientific Reports, 8, 2018, doi: 10.1038/s41598-018-34571-9.

Ludwig Erik Aguilar, et al., "Supramolecular Caffeic Acid and Bortezomib Nanomedicine: Prodrug Inducing Reactive Oxygen Species and Inhibiting Cancer Cell Survival," Pharmaceutics, 12, 2020, doi: 10.3390/pharmaceutics12111082.

Ernest Sondheimer, et al., "Isolation of Chlorogenic Acid and Its Isomers from Coffee," Agricultural and Food Chemistry, vol. 9, No. 2, Mar.-Apr. 1961.

J. Song, et al., "Modulation of Gut Microbiota by Chlorogenic Acid Pretreatment on Adrenocorticotropic Hormone, Induced Depression-like Behavior Rats," Food Funct., 2019, DOI: 10.1039/C8FO02599A.

Zhengyu Wang, et al., "Chlorogenic Acid Alleviates Obesity and Modulates Gut Microbiota in High-Fat-Fed Mice," food Sci Nutr., vol. 7, 2019, pp. 579-588, doi: 10.1002/fsn3.868.

International Search Report & Written Opinion for PCT/US2022/078488 mailed on Jan. 24, 2023.

Ruby I. Rowe, et al., "Boron is Required for Zebrafish Embryogenesis," The Journal of Experimental Biology 202, pp. 1649-1654, 1999.

Meng Jiang et al., "Boric Acid Was Orally Toxic to Different Instars of *Blattella germanica* (L.) (Blattodea: Blattellidae) and Caused Dysbiosis of the Gut Microbiota," Pesticide Biochemistry and Physiology, Dec. 13, 2020, https://doi.org/10.1016/j.pestbp.2020.104756.

Jessica A. Thompson, et al., "Chemical Conversations in the Gut Microbiota," Gut Microbes, 2016, vol. 7, No. 2, pp. 163-170, http://dx.doi.org/10.1080/19490976.2016.1145374.

Hyo-Joong Kim, et al., "Evaporite Borate-Containing Mineral Ensembles Make Phosphate Available and Regiospecifically Phosphorylate Ribonucleosides: Borate as a Multifaceted Problem Solver in Prebiotic Chemistry," Angew. Chem. Int. Ed. 2016, 55, pp. 1-6, doi: 10.1002/anie.201608001.

Daan Kremer, et al., "A systematic review and meta-analysis of Covid-19 in kidney transplant recipients: Lessons to be learned," Am J Transplant. 2021, 21, pp. 3936-3945, doi: 10.1111/ajt/16742.

Naresh Kumar, et al., "Phenolic acids: Natural versatile molecules with promising therapeutic applications," Biotechnology Reports 24, 2019, https://doi.org/10.1016/j.btre.2019.e00370.

M. Makkee, et al., "Studies on Borate Esters III*, Borate Esters of D-Mannitol, D-Glucitol, D-Fructose, and D-glucose in Water," Reel. Trav. Chim. Pays-Bas 104, pp. 230-235, 1985.

Ravichandra Vemuri, et al., "Beyond Just Bacteria: Functional Biomes in the Gut Ecosystem Including Virome, Mycobiome, Archaeome, and Helminths," Microorganisms 2020, 8, 483, doi: 10.3390/microorganisms8040483.

S. Miyamoto, et al., "Determination of Boron in Animal Materials by Reactor Neutron Induced Prompt Gamma-Ray Analysis," Journal of Radioanalytical and Nuclear Chemistry, vol. 244, No. 2, 2000, pp. 307-309.

Michael Hofer, et al., "Granulocyte Colony-Stimulating Factor in the Treatment of Acute Radiation Syndrome: A Concise Review," Molecules 2014, 19, pp. 4770-4778, doi: 10.3390/molecules19044770.

Jesus Santana-Galvez, et al., "Chlorogenic Acid: Recent Advances on Its Dual Role as a Food Additive and Nutraceutical against Metabolic Syndrome," Molecules 2017, 22, 358, doi: 10.3390/molecules22030358.

M. Deeny, et al., "Changes in the bone and liver isoenzymes of alkaline phosphatase in postmenopausal women being treated with norethisterone," Clin. Chim. ACTA, 171/1, pp. 103-108, 1988.

Forrest H. Nielsen, "The Justification for Providing Dietary Guidance for the Nutritional Intake of Boron," Biological Trace Element Research, vol. 66, 1998, pp. 319-330.

Forrest H. Nielsen, "Update on Human Health Effects of Boron," J Trace Elem Med Biol, 2014, http://dx/doi.org/10.1016/j.jtemb.2014.06.023.

(56) References Cited

OTHER PUBLICATIONS

Ansel Hsiao, et al., "Members of the human gut microbiota involved in recorvery from Vibrio cholerae infection," Nature, Nov. 20, 2014, 515(7527), doi: 10.1038/nature13738.
Melinda A. Engevik, et al., "Biochemical features of beneficial microbes: foundations for therapeutic microbiology," Microbiol Spectr., Oct. 2017, 5(5), doi: 10.1128/microbiolspec.BAD-0012-2016.
"Boric Acid Technical Fact Sheet," National Pesticide Information Center, npic/orst.edu/factsheets/archive/borictech.html.
Glenn R. Gibson, et al., "The International Scientific Association for Probiotics and Prebiotics (ISAPP) Concensus Statement on the Definition and Scope of Prebiotics," Nature Reviews, Gastroenterology & Hepatology, vol. 14, Aug. 2017, pp. 491-502, doi: 10.1038/nrgastro.2017.75.
Forrest H. Nielsen, "Is Boron Nutritionally Relevant?" Nutrition Reviews, vol. 66(4), pp. 183-191, doi: 10.1111/j.1753-4887.2008.00023.x.
O. Sizmaz et al., "Rumen microbial fermentation, protozoan abundance and boron availability in yearling rams fed diets with different boron concentrations," Journal of Animal and Feed Sciences, 26, 2017, 59-64, https://doi.org/10.22358/jafs/69038/2017.
Stephen T. Miller, et al., "*Salmonella typhimurium* Recognizes a Chemically Distinct Form of the Bacterial Quorum-Sensing Signal Al-2," Molecular Cell, vol. 15, pp. 677-687, Sep. 10, 2024.
Jessica Ann Thompson, et al., "Manipulation of the Quorum Sensing Signal Al-2 Affects the Antibiotic-Treated Gut Microbiota," Cell Reports 10, pp. 1861-1871, Mar. 24, 2015.
Joelle Fournier, et al., "Mechanism of Infection Thread Elongation in Root Hairs of Medicago Truncatula and Dynamic Interplay with Associated Rhizobial Colonization," Plant. Physiology, Dec. 2008, vol. 148, pp. 1985-1995.
Juraj Prejac, et al., "Assessing the boron nutritional status by analyzing its cummulative frequency distribution in the hair and whole blood," Journal of Trace Elements in Medicine and Biology 25, 2018, pp. 50-56, http://dx.doi.org/10.1016/j.jtemb.2017.09.018.
Andrei Bita, et al., "New Insights into the Boron Essentiality on Humans and Animals," doi: 10.20944/preprints202206.0030.v1.
Polasa Indira, et al., "Quantification of Pentaerythritol Tetrastearate—A Mold Release Agent Used in Polycarbonate by Non-Aqueous Reversed Phase HPLC Method," Journal of Separation Science, doi: 10.1002/jssc.201801086.
Ioana Mitrut, et al., "Preclinical and Histological Study of Boron-Containing Compounds Hydrogels on Experimental Model of Periodontal Disease," Rom J Morphol Embryol 2021, 62(1), pp. 219-226, doi: 10.47162/RJME.62.1.21.
Mariangela Rondanelli, et al., "Pivotal Role of Boron Supplementation on Bone Health: A Narrative Review," Journal of Trace Elements in Medicine & Biology 62, 2020, https://doi.org/10.1016/j.jtemb.2020.126577.
Ruby I. Rowe, et al., "The Response of Trout and Zebrafish Embryos to Low and High Boron Concentrations is U-Shaped," Biological Trace Element Research, vol. 66, 1998, pp. 261-270.
Steve Atkinson, et al., "Quorum Sensing and Social Networking in the Microbial World," J.R. Soc. Interface, 2009, 6, pp. 959-978, doi: 10.1098/rsif.2009.0203.
R. Scorei et al., "Boron Enhances the Thermostability of Carbohydrates," Origins of Life and Evolution of Biospheres, 2006, 26, pp. 1-11.
Romulus Scorei, "Is Boron a Prebiotic Element? A Mini-Review of the Essentiality of Boron for the Appearance of Life on Earth," Orig Life Evol Biosph, 2012, 42, pp. 3-17, doi: 10.1007/s11084-012-9269-2.
Amrita Vijay et al., "Role of the Gut Microbiome in Chronic Diseases: A Narrative Review," European Journal of Clinical Nutrition, 2022, 76, pp. 489-501, https://doi.org/10.1038/s41430-021-00991-6.
Tal Frolinger et al, "The gut microbiota composition affects dietary polyphenolsmediated cognitive resilience in mice by modulating the bioavailability of phenolic acids," Scientific Reports, 2019, 9, 3546, https://doi/org/10.1038/s41598-019-39994-6.
Hao Guo, et al.,"Multi-Omics Analyses of Radiation Survivors Identify Radioprotective Microbes and Metabolites," Science 370, 549, Oct. 30, 2020, doi: 10.1126/science.aay9097.
Romulus Ion Scorei, et al., "Calcium Fructoborate—Potential Anti-Inflammatory Agent," Biol Trace Elem Res, 2011, 143, pp. 1223-1238, doi: 10.1007/s12011-011-8972-6.
Vijay K. Singh, et al., "Radiation countermeasure agents: an update (2011-2014)," Expert Opin. Ther. Patents, 2014, 24(11), pp. 1229-1255.
Ibrahim Sogut, et al., "The Antioxidant and Antiapoptotic Effect on Boric Acid on Hepatoxicity in Chronic Alcohol-Fed Rats," Can. J. Physiol. Pharmacol.
Hideyuki Tominaga et al., "A water-soluble tetrazolium salt useful for colormetric cell viability assay," Anal. Commun., 1999, 36, pp. 47-50.
P.R. Twentyman et al., "A study of some variables in a tetrazolium dye (MTT) based assay for cell growth and chemosensitivity," Br. J. Cancer, 1987, 56, pp. 279-285.
Kan Usuda et al., "Serum and urinary boron levels in rats after single administration of sodium tetraborate," Arch Toxicol, 1998, 72, pp. 468-474.
Hao-Nan Wang et al., "Isochlorogenic acid (ICGA): natural medicine with potentials in pharmaceutical developments," Chinese Journal of Natural Medicines, 2020, 18 (11), pp. 860-871, doi: 10.1016/s1875-5364(20)60029-2.
Ionut Donoiu et al., "Effects of Boron-Containing Compounds on Cardiovascular Disease Risk Factors—A Review," Journal of Trace Elements in Medicine and Biology 50, 2018, pp. 47-56.
Annie-Claude Bourgeois, et al., "Low Dietary Boron Reduces Parasite (Nematoda) Survival and Alters Cytokine Profiles by the Infection Modifies Liver Minerals in Mice," The Journal of Nutrition, Nutrition and Disease, pp. 2080-2086.
Vijay K. Singh, et al., "Entolimod as a Radiation Countermeasure for Acute Radiation Syndrome," Drug Discovery Today, vol. 00, No. 00, Oct. 2020.
Forrest H. Nielsen, et al., "Boron", The Author(s) 2019, Adv Nutr 2020, 11, pp. 461-462, https://doi.org/10.1093/advances/nmz110.
Tošovič, J., et al., "Antioxidative mechanisms in chlorogenic acid," Food Chemistry (2017), doi: http://dx.doi.org/10.1016/j.foodchem.2017.05.080.
Havalli Bommegowda Rashmi et al., "Phenolic Acids from Vegetables: A Review on Processing Stability and Health Benefits," Food Research International 136, 2020.
Ruya Kuru, et al., "Boron-Rich Diet May Regulate Blood Lipid Profile and Prevent Obesity: A Non-Drug and Self-Controlled Clinical Trial," Journal of Trace Elements in Medicine and Biology, 54, 2019 pp. 191-198.
Luis Bolanos, et al., "Why Boron?", Plant Physiology and Biochemistry 42, Dec. 16, 2004, pp. 907-912.
Ivan J. Bazany-Rodriguez, et al., "Chemosensing of Neurotransmitters with Selectivity and Naked Eye Detection of L-DOPA based on Flourescent Zn(II)-terpyridine Bearing Boronic Acid Complexes", Dalton Transactions, 2021, 50, 4255.
C. Sanchez-Moreno, "Review: Methods Used to Evaluate the Free Radical Scavenging Activity in Foods and Biological Systems," Food Science and Technology International, http://fst.sagepub.com/content/8/3/121.
Huijie Lu, et al., "Chlorogenic Acid: A Comprehensive Review of the Dietary Sources, Processing Effects, Bioavailability, Beneficial Properties, Mechanisms of Action, and Future Directions," Comprehensive Reviews in Food Science and Food Safety, Jul. 23, 2020, DOI: 10.1111/1541-4337.12620.
Dr. Krishna Sharma, et al., "Gut-Organ Axis: A microbial Outreach and Networking," doi:10.111.LAM.13333.
A. Ricardo, et al., "Borate Minerals Stabilize Ribose," Science, New Series, vol. 303, No. 5655, Jan. 9, 2004 p. 196.
Dursun Ali Kose, et al., "Mixed-Ligand Complexes of Boric Acid with Organic Biomolecules," Chemical Papers 66 (1), pp. 54-60, 2012, doi: 10.2478/s11696-011-0108-0.
Omer Faruk Kocak, et al., "Bor Sitrat Uygulanan Ratlarin Serum ve Plamalarinda Bor Tayini," Boron 7(2) pp. 482-486, 2022.

(56) References Cited

OTHER PUBLICATIONS

Matthew J. Bull, et al., "The Human Gut Microbiome in Health and Disease," Integrative Medicine, vol. 13, No. 6, Dec. 2014, pp. 17-22.
Juan E. Gonzalez et al., "Quorum Sensing in Nitrogen-Fixing Rhizobia," Microbiology and Molecular Biology Reviews, Dec. 2003, pp. 574-592, doi: 10.1128/MMBR/67.4.574-592.2003.
Katharina S. Weber, et al., "Plasma Boron Concentrations in the General Population: A Cross-Sectional Analysis of Cardio-Metabolic and Dietary Correlates," European Journal of Nutrition (2022) 61, pp. 1363-1375.
James B. Kaper, et al., "Bacterial Cell-to Cell Signaling in the Gastrointestinal Tract," Infection and Immunity, Jun. 2005, pp. 3197-3209, doi: 10.1128/IAI.73.6.3197-3209.2005.
John M. Hunter, et al., "The Fructoborates: Part of a Family of Naturally Occurring Sugar-Borate Complexes—Biochemistry, Physiology, and Impact on Human Health: A Review," Biological Trace Element Research (2019) 188, pp. 11-25.
Michael J. Federle, et al., "Interspecies Communication in Bacteria," The Journal of Clinical Investigation 2003, 112 (9), pp. 1291-1299, https://doi.org/10.1172/JCI20195.
Lei Zhang, et al., "Sensing of Autoinducer-2 by Functionality Distinct Receptors in Prokaryotes," Nature Communications. https://doi.org/10.1038/s41467-020-19243-5.
Rex E. Newnham, "Essentiality of Boron for Healthy Bones and Joints," Eviron Health Perspect 102 (Suppl 7), pp. 83-85, 1994.
Hyun Min Cho, et al., "Moderate Dietary Boron Supplementation Improved Growth Performance, Crude Protein Digestibility and Diarrhea Index in Weaner Pigs Regardless of the Sanitary Condition," Anim Biosc, vol. 35, No. 3, pp. 434-443, Mar. 2022, https://doi.org/10.5713/ab.21.0110.
Isidro Abreu et al., "Boron Deficiency Affects Rhizobia Cell Surface Polysaccharides Important for Suppression of Plant Defense Mechanisms During Legume Recognition and for Development of Nitrogen-Fixing Symbiosis," Plant Soil, 2012, 361, pp. 385-395.
Iftikhar Ahmed, et al., "Mechanism of Boron Tolerance in Soil Bacteria," Can. J. Microbiol. 56, pp. 22-26, 2010.
PengPeng Sun et al., "Effects of Supplemental Boron on Intestinal Proliferation and Apoptosis in African Ostrich Chicks," Int. J. Morphol., 34 (3), pp. 830-835, 2016.
Colin F. Bell, et al., "Boric Acid Complexes of Phenolic Acids," Polyhedron vol. 10, No. 6, pp. 613-618, 1991.
Stig Bengmark, "Colonic Food: Pre- and Probiotics," The American Journal of Gastroenterology, vol. 95, No. 1, Suppl., 2000.
Michael V. Berridge et al., "Tetrazolium Dyes as Tools in Cell Biology: New Insights into their Cellular Reduction," Biotechnology Annual Review, vol. 11, doi: 10.1016/S1387-2656(05)11004-7.
Andrei Bita, et al., "Simultaneous Quantitation of Boric Acid and Calcium Fructoborate in Dietary Supplements by HPTLC-Densitometry," Analytical Sciences, the Japan Society for Analytical Chemistry, Jun. 2017, vol. 33, 2017.
Luis Bolanos et al., "Essentiality of Boron for Symbiotic Dinitrogen Fixation in Pea (*Pisum sativum*) Rhizobium Nodules," Plant Physiol., 104, pp. 85-90, 1994.
Luis Bolanos et al., "Boron Requirement in the Discaria Trinervis (Rhamnaceae) and Frankia Symbiotic Relationship. Its Essentiality for Frankia BCU110501 Growth and Nitrogen Fixation," Physiologia Plantarum 115, pp. 563-570, 2002.
Xin Chen et al., "Structural Identification of a Bacterial Quorum-Sensing Signal Containing Boron," Nature, vol. 415, Jan. 31, 2002.
Giancarlo A. Cuadra et al., "Autoinducer-2 Detection Among Commensal Oral Streptococci is Dependent on pH and Boric Acid," Journal of Microbiology, vol. 54, No. 7, pp. 492-502, 2016.
Donoiu I, Militaru C, et al., "Effects of Boron-Containing Compounds on Cardiovascular Disease Risk Factors—A Review," Journal of Trace Elements in Medicine and Biology (2018), https://doi.org/10.1016/j.jtemb.2018.06.003.
Dominique Turck et al., "Safety of Calcium Fructoborate as a Novel Food Pursuant to Regulation (EU) 2015/2283," EFSA Journal 2021, vol. 19(7), May 25, 2021, doi: 10.2903/j.efsa.2021.6661.
Curtiss D. Hunt, "The Biochemical Effects of Physiologic Amounts of Dietary Boron in Animal Nutrition Models," Environmental Health Perspectives, Dietary Boron and Animal Physiology, vol. 102, Supplement 7, Nov. 1994.
Elizabeth Estevez-Fregoso, et al., "Effects of Boron-Containing Compounds in the Fungal Kingdom," Journal of Trace Elements in Medicine and Biology 65, 2021, https://doi.org/10.1016/j.jtemb.2021.126714.
Daniel Hernandez-Patlan, et al., "Evaluation of the Antimicrobial and Intestinal Integrity Properties of Boric Acid in Broiler Chickens Infected with Salmonella Enteritidis: Proof of Concept," Dec. 13, 2018, https://doi.org/10.1016/j.rvsc.2018.12.004.
Lauris Evariste et al., "Ecotoxicological assessment of commercial boron nitride nanotubes toward *Xenopus laevis* tadpoles and host-associated gut microbiota," Nanotoxicology, DOI: 10.1080/17435390.2020.1839137.
Yangyang Li et al., "Review: Effect of Gut Microbiota and Its Metabolite SCFAs on Radiation-Induced Intestinal Injury," Front. Cell. Infect. Microbiol., doi: 10.3389/fcimb.2021.577236.
Xialin Ye, et al., "Chlorogenic Acid-Induced Gut Microbiota Improves Metabolic Endotoxemia," Front. Endocrinol., doi: 10.3389/fendo.2021.762691.
Dorna Davani-Davari et al.,, "Prebiotics: Definition, Types, Sources, Mechanisms, and Clinical Applications," Foods, 8, 92, doi:10.3390/foods8030092.
Soirios Kiokias et al., Phenolic Acids of Plant Origin—A Review on their Antioxidant Activity in Vitro (O/W Emulsion Systems) Along with their In Vivo Health Biochemical Properties, Foods 2020, 9, 534, doi: 10.3390/foods9040534.
Greice Leal Pereira, et al., "Boron: More Than an Essential Element for Land Plants?", Front. Plant Sci. 11:610307, doi: 10.3389/fpls.2020.610307.
Mario Matijasic, et al., "Gut Microbiota Beyond Bacteria—Mycobiome, Virome, Archaeome, and Eukaryotic Parasites in IBD," Int. J. Mol. Sci. 2020, 21, 2668, doi: 10.3390/ijms21082668.
Huan Chen et al., "Boron Derivatives Accelerate Biofilm Formation of Recombinant *Escherichia coli* via Increasing Quorum Sensing System Autoinducer-2 Activity," Int. J. Mol. Sci 2022, 23, 8059. https://doi.org/10.3390/ijms23158059.
Andrei Bita, et al., "Diester Chlorogenoborate Complex: A New Naturally Occurring Boron-Containing Compound," Inorganics 2023, 11, 112, https://doi.org/10.3390/inorganics11030112.
Juliana Durack, et al., "The Gut Microbiome: Relationships with Disease and Opportunities for Therapy," J. Exp. Med. 2018, vol. 216, No. 1, pp. 20-40.
Xiao-ming Tan et al., "Complexation Between Borate Ion and Hydroxyl Groups of Phenol-Formaldehyde Resol Resin," Journal of Wuhan University of Technology—Mater. Sc. Ed., vol. 17, No. 1, Mar. 2002, pp. 14-18.
"Boron: the essential element for vascular plants that never was," New Phytologist (2019) 221, pp. 1685-1690.
Valery M. Dembitsky et al., "Aromatic compounds and their fascinating boron complexes as potential quorum sensing molecules," Vietnam J. Chem., 2025, Mar. 6, 2025, pp. 1-29; DOI: 10.1002/vjch.70013.
Adriana Farah, et al., "Consumption of Chlorogenic Acids through Coffee and Health Implications," Beverages 2019, 5,11, doi:10.3390/beverages5010011.
Martin J.G. Hebert et al., "Synthesis and Biological Activity of Arylspiroborate Salts Derived from Caffeic Acid Phenethyl Ester," International Journal of Medicinal Chemistry, vol. 2015, Article ID 418362, 9 pgs., http://dx.doi.org/10.1155/2015/418362.
Andrezej L. Dawidowicz et al., "Formation of Ester and Amine Derivatives of 5-O-Caggeolyquinic Acid in the Process of Its Simulated Extraction," Journal of Agricultural and Food Chemistry, vol. 60, Nov. 25, 2012, pp. 12289-12295.
Paola Vitaglione et al., "Coffee, colon function, and colorectal cancer," The Royal Society of Chemistry 2012, DOI: 10.1039/c2fo30037k.
Zhan Zhang et al., "Chlorogenic Acid Ameliorates Experimental Colitis by Promoting Growth of Akkermansia in Mice," Nutrients 2017, vol. 9, 677, Jun. 29, 2017, doi: 10.3390/nu9070677.

(56) References Cited

OTHER PUBLICATIONS

Jesus Santana-Galvez et al., "Chlorogenic Acid: Recent Advances on Its Dual Role as a Food Additive and a Nutraceutical against Metabolic Syndrome," Molecules 2017, 22, 358, Feb. 26, 2017, doi:10.3390/molecules22030358.
Xiaolin Ye et al., "Chlorogenic Acid-Induced Gut Microbiota Improves Metabolic Endotoxemia," Front. Endocrinol., doi:10.3389/fendo.2021.762691.
Vitaglione P, Fogliano V, Pellegrini N. "Coffee, Colon function and colorectal cancer" Food Funct (2012) Sep 3 (9):916-22.
Adriana Farah and Juliana de Paula Lima. "Consumption of Chlorogenic Acids through Coffee and Health Implications" Beverages (2019), 5(1), 11. (Published Feb. 1, 2019).
Dembitsky V M, Smoum R, Al-Quntar A A, et al. "Natural occurrence of boron-containing compounds in plants, algae and microorganisms". Plant Science, 2002, 163(5): 931-942.
Sun, J., Daniel, R., Wagner-Döbler, I. et al. "Is autoinducer-2 a universal signal for interspecies communication: a comparative genomic and phylogenetic analysis of the synthesis and signal transduction pathways". BMC Evol Biol 4, 36 (2004).
Dupre J N, Keenan M J, Hegsted M, et al. "Effects of dietary boron in rats fed a vitamin D-deficient diet" [J]. Environmental Health Perspectives, 1994, 102(suppl 7): 55-58.
Zumreoglu-Karan, Birgul and Kose, Dursun Ali. "Boric acid: a simple molecule of physiologic, therapeutic and prebiotic significance" Pure and Applied Chemistry, vol. 87, No. 2, (2015), pp. 155-162.
Romulo, A. "Extraction of phenolic compounds using subcritical hot water extraction: a review." In IOP Conference Series: Earth and Environmental Science (Feb. 2020) (vol. 426, No. 1, p. 012173). IOP Publishing.
Martin J.G. Hebert et al. "Synthesis and Biological Activity of Arylspiroborate Salts Derived from Caffeic Acid Phenethyl Ester". International Journal of Medicinal Chemistry (2015). Vol 2015, Issue 1 (published Jan. 2015).
Andrzej L. Dawidowicz and Rafal Typek. "Formation of Ester and Amine Derivatives of 5-O-Caffeoylquinic Acid in the Process of Its Simulated Extraction". Journal of Agricultural and Food Chemistry (2012). vol. 60. Issue 50 (published Nov. 25, 2012).

* cited by examiner

NMR $^1$H

NMR $^1$H

BORATE COMPLEXES OF CHLOROGENIC ACID AND USES THEREOF

CROSS-REFERENCE TO RELATED APPLICATIONS

This application claims the benefit of:

U.S. Provisional Application No. 63/271,159, filed on Oct. 24, 2021; and

U.S. Provisional Application No. 63/326,931, filed on Apr. 4, 2022.

The entire disclosure of each prior application is incorporated herein by reference.

TECHNICAL FIELD

Various exemplary embodiments disclosed herein relate generally to extracts of green coffee beans with a high content of borate complexes of chlorogenic acid having beneficial health effects.

BACKGROUND

Coffee has traditionally been consumed primarily for its taste and aroma and the stimulating effect of caffeine. The two main commercially cultivated species are *Coffea canephora* (predominantly a form known as '*robusta*') and *Coffea Arabica*. Potential health benefits of coffee bean derived phytochemicals include prevention of several chronic and degenerative diseases, such as cancer, cardiovascular disorders, diabetes and Parkinson's disease and also management of obesity. The green coffee beans are a source of beneficial phenolic compounds average 4% phenolic acids per dry matter and 10-25 ppm boron.

Prebiotics, which are food components that stimulate the growth of beneficial bacteria in the human intestine microbiota, are a growing area of food research. Chlorogenic acid (CGA) has shown activity as a prebiotic. Coffee with high levels of CGA (high-CGA coffee) induced a significant increase in the growth of *Bifidobacterium* spp. as well as the *Clostridium coccoides-Eubacterium* rectale group, the latter group having potential to benefit human health. The diverse bacterial communities were able to facilitate conversion of 3-O-caffeoyl-quinic acid (C-QA, a type of chlorogenic acid) into 3-(3-hydroxyphenyl) propanoic acid (HPPA). This requires the removal or the breakdown of the quinic acid moiety, the reduction of the propenoic double bond, and conversion of a 3,4-dihydroxyphenyl moiety to a 3-hydroxyphenyl moiety by dehydroxylation.

Chlorogenic acid alleviates colon mucosal damage induced by a high-fat diet via gut microflora adjustment to increase short-chain fatty acid accumulation in rats. Chlorogenic acid ameliorates colitis and alters colonic microbiota in a mouse model of dextran sulfate sodium-induced colitis. CGA can regulate the abundance and diversity of the intestinal microbial community and improve liver inflammation and steatosis by reducing inflammation mediated by LPS/TLR4 signaling. LPS/TLR4 signaling involves stimulation of Toll-like receptor 4 (TLR4) by lipopolysaccharide (LPS), inducing the release of proinflammatory cytokines that activate immune responses.

Coffee consumption modulates dysbiosis in the gut caused by antibiotics. Coffee consumption has an impact on the microbiome's response to antibiotics.

There is growing evidence that boron is essential for the growth of certain types of bacteria, such as heterocyst cyanobacteria and actinomycetes of the *Frankia* genus. For example: fifteen strains of bacteria (*Arthrobacter, Rhodococcus, Lysinibacillus, Algoriphagus, Gracilibacillus* and *Bacillus* taxa) were isolated and then they showed tolerance to high concentrations of B. In general, in symbiosis with other kingdoms, bacteria use the ability of boron to attach to glycoproteins, thus blocking the bacterium from infecting a symbiotic host organism. The gut microbiota colonizes the gastrointestinal tract and represents an ecosystem that weighs about 1.5 kg, being composed of more than 1500 bacteria and more than 1000 other species, e.g., fungus, viruses, parasites and archaebacteria. The most representative healthy bacterial phyla found in the gut are Bacteroidetes and Firmicutes, followed by Actinobacteria, Fusobacteria and Proteobacteria. The most representative species include species of *Bacteroides, Faecalibacterium* and *Bifidobacterium*. The gut microbiota has several functions such as nutrients absorption, maintaining metabolic homeostasis, protection from infections, and the development of systemic immunity and mucosa. The bacterial quorum-sensing boron compound AI-2B (furanosyl borate diester) may influence bacterial behaviors to restore balance between the major species of Bacteroidetes and Firmicutes bacteria. AI-2B is produced by several bacterial species found in the gastrointestinal tract, including *Bacteroides* spp., *Ruminococcus* spp., *Eubacterium* rectale and *Lactobacillus* spp. These observations led to the conclusion that AI-2B is one of the signaling molecules that regulates bacterial behavior and community dynamics in the microbiota and may also modulate the composition of the microbiota under dysbiosis conditions. The production of AI-2B by a species can influence the expression of genes of other species and can promote communication between species, allowing bacteria to change their behavior, namely virulence, luminescence, and the formation of biofilms between different species. This feature makes AI-2B an excellent candidate for mediating cell-cell interactions in mammalian intestines.

In many diseases, the microbiota has a modified structure, which causes pathophysiological diseases in vital human organs. The interactions between the intestinal microbiota and the host immune system results in the formation of an "axis" between the intestinal microbiota and various organs. The "host-microbe" metabolic axis is a multidirectional systemic communication between the host's cellular pathways and various microbial species in the microbiota. Within these axes, different microbes sequentially modulate metabolic reactions by producing bile acids, choline, and short-chain fatty acids (SCFAs), which are vital to host health. The production of these metabolites contributes to the host's metabolic phenotype and to the risk of developing the disease.

Various embodiments disclosed herein relate to a composition including a borate ester of chlorogenic acid, where the composition is produced by a process of reacting a green coffee bean extract including a chlorogenic acid with boric acid in a solvent comprising water or a mixture of water and an organic solvent to produce an aqueous reaction mixture; if the solvent comprises the organic solvent, evaporating the organic solvent from the aqueous reaction mixture after the completion of the reacting step; and freeze-drying the aqueous reaction mixture to produce the composition including the borate ester of chlorogenic acid. The method may include a step of reacting the green coffee bean extract including the chlorogenic acid with boric acid in superheated water at a pressure of 1.5 bar to 85 bar and a temperature of 110° C. to 300° C.

In view of the foregoing, it would be desirable to provide improved formulations based on chlorogenic acid and/or boron to improve gut health and support microbiome health.

SUMMARY

In light of the present need for improved gut health, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments disclosed herein relate to a method to produce an extract comprising a chlorogenic acid and a borate diester of chlorogenic acid, by extracting green coffee beans in a solvent comprising water or a mixture of water and an organic solvent to produce an aqueous reaction mixture; if the solvent comprises the organic solvent, evaporating the organic solvent from the aqueous reaction mixture after the completion of the extracting step; and either:

- freeze-drying the aqueous reaction mixture to produce the extract comprising the chlorogenic acid and the borate diester; or
- evaporating water from the aqueous reaction mixture to produce the extract comprising the chlorogenic acid and the borate diester. The method may further include adding boric acid to the aqueous reaction mixture during the reacting step to provide the extract with an increased content of the borate diester.

Various embodiments disclosed herein relate to a method to produce a composition including a borate ester of chlorogenic acid, by reacting a chlorogenic acid with boric acid in a solvent comprising water or a mixture of water and an organic solvent to produce an aqueous reaction mixture; if the solvent includes the organic solvent, evaporating the organic solvent from the aqueous reaction mixture after the completion of the reacting step; and either:

- freeze-drying the aqueous reaction mixture to produce the extract comprising the chlorogenic acid and the borate ester; or
- evaporating water from the aqueous reaction mixture to produce the extract comprising the chlorogenic acid and the borate ester. The reacting step may include reacting a green coffee bean extract comprising the chlorogenic acid with the boric acid in superheated water at a pressure of 1.5 bar to 85 bar and a temperature of 110° C. to 300° C.; and then freeze-drying the aqueous reaction mixture. The reacting step may include reacting the chlorogenic acid with the boric acid in superheated water at a pressure of 1.5 bar to 85 bar and a temperature of 110° C. to 300° C., or at a pressure of 4 bar to 25 bar and a temperature of 125° C. to 225° C.; and then freeze-drying the aqueous reaction mixture.

The borate ester of chlorogenic acid may be made by reacting chlorogenic acid and boric acid in superheated water at a pressure of 1.5 bar to 85 bar, 2 bar to 75 bar, 2.5 bar to 65 bar, 3 bar to 50 bar, 3.5 bar to 35 bar, 4 bar to 25 bar, or 4.5 bar to 10 bar; and a temperature of 110° C. to 300° C., 115° C. to 300° C., 120° C. to 250° C., 125° C. to 225° C., 130° C. to 200° C., 135° C. to 1750 C, 140° C. to 160° C., for about 10 minutes to 8 hours, 15 minutes to 6 hours, 20 minutes to 4 hours, 25 minutes to 2 hours, or 30 minutes to 1 hour.

Various embodiments disclosed herein relate to a process for preparing a borate ester of chlorogenic acid, e.g., a chlorogenic boric acid diester or a diester chlorogenoborate (DCB), by preparing a solution comprising chlorogenic acid and boric acid in a mass ratio of at least 1:1 in a solvent comprising water or aqueous acetonitrile at a temperature of 40° C. to 80 C, 55° C. to 70° C., or about 65° C.; evaporating acetonitrile, if present, from the solvent under vacuum to prepare a water solution comprising the borate ester of chlorogenic acid; and either lyophilizing the water solution of the borate ester of chlorogenic acid; or air drying the water solution of the borate ester of chlorogenic acid.

The reacting step may include reacting the chlorogenic acid or a green coffee bean extract comprising the chlorogenic acid with the boric acid in aqueous acetonitrile at a temperature of 40° C. to 80° C., 55° C. to 70° C., or about 65° C.

Various embodiments disclosed herein relate to a method of treating insufficient boron levels, also described as boron deficiency, in a microbiome in a subject in need thereof, by administering an effective amount of a borate ester of chlorogenic acid to the subject, wherein the borate ester is DCB and has a structure of formula (I) or a structure of formula (II), where X is hydrogen or a pharmaceutically acceptable cation:

(I)

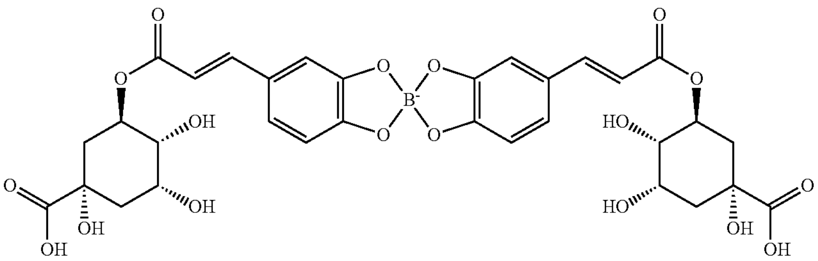

$X^+$

-continued (II)

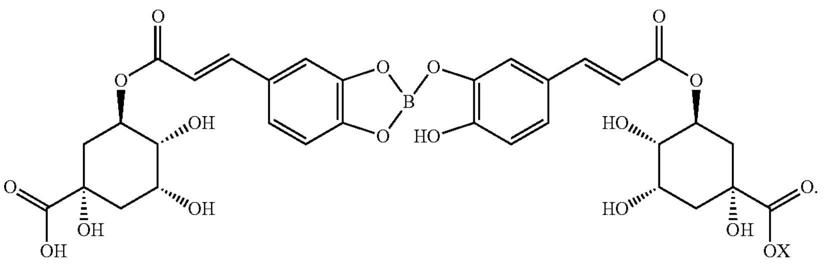

In various embodiments, the microbiome includes microorganisms found in a lower gastrointestinal tract, an oral mucosal surface, a skin surface, or a vaginal surface. The microbiome may include the microorganisms found in the lower gastrointestinal tract or the vaginal surface, and the borate ester may be administered to the subject in a suppository. The microbiome may include the microorganisms found in the lower gastrointestinal tract, and administering the borate ester relieves diarrhea caused by dysbiosis of the microbiome. The microbiome may include the microorganisms found in the oral mucosal surface, and the borate ester may be administered to the subject in a mouthwash, a toothpaste, a sublingual tablet, a buccal tablet, or a candy. The microbiome may include the microorganisms found on the skin surface, and the borate ester may be administered to the subject in a topical cream or ointment.

Administering the borate ester to the subject may improve microbiome health by alleviating boron deficiency, or increasing boron levels, in a beneficial microorganism of the genus *Bifidobacterium*, a beneficial microorganism of the genus *Lactobacillus*, or a mixture thereof; and/or inhibiting the growth of a pathogenic microorganism of the species *Escherichia coli*, a pathogenic microorganism of the species *Klebsiella pneumoniae*, a pathogenic microorganism of the species *Proteus mirabilis*, a pathogenic microorganism of the species *Staphylococcus haemolyticus*, a pathogenic microorganism of the species *Enterococcus faecalis*, a pathogenic microorganism of the species *Candida albicans*, or a mixture thereof.

Various embodiments disclosed herein relate to a method of treating insufficient boron levels of a microbiome in a subject in need thereof, by administering an effective amount of a borate ester of formula (I) or a structure of formula (II) to the subject, wherein the method further includes administering a probiotic bacteria to the subject, wherein the probiotic bacteria may be:

Bacteria from a phylum Bacteroidetes, Firmicutes, or a combination thereof;

Bacteria from a genus *Lactobacillus, Bifidobacterium, Leuconostoc, Pediococcus, Bacteroides, Akkermansia, Streptococcus*, and *Bacillus*, or a combination thereof; and/or Bacteria from a species *Leuconostoc mesenteroides, Lactobacillus plantarum, Pediococcus pentosaceus, Lactobacillus brevis, Leuconostoc citreum, Leuconostoc argentinum, Lactobacillus paraplantarum, Lactobacillus corymformis, Leuconostoc mesenteroides, Lactobacillus lactis, Lactobacillus fermentum, Lactobacillus acidophilus, Bifidobacterium bifidum, Lactobacillus delbrueckii* subsp. *bulgaricus, Lactobacillus helveticus, Lactobacillus kefiranofaciens*, or a combination thereof.

In various embodiments, administering the borate ester to a subject improves the health of the subject by ameliorating metabolic diseases; ameliorating psychiatric diseases; ameliorating dysbiosis of gut and oral microbiota; ameliorating gut mucus layer degradation; ameliorating intestinal barrier hyperpermeability; attenuating brain ischemic injury in patients at risk of ischemic stroke; ameliorating atherosclerosis; increasing neurotransmitter levels; ameliorating hormone imbalance; assisting in obesity management; and/or slowing the aging process.

Dysbiosis of a microbiome may be diagnosed and treated in a patient, by obtaining a sample comprising bacteria from the microbiome of the patient, wherein the microbiome is in an oral mucosa, and the sample comprises a sample of saliva or an oral mucus gel layer; or the microbiome is in a colon, and the sample comprises a stool sample or a sample of a colonic mucus gel layer; detecting a level of furanosyl borate diester in the sample; and, if the level of furanosyl borate diester is less than a target value, increasing the level of furanosyl borate diester in the microbiome of the patient by administering a chlorogenic acid diester of boric acid to the patient. Detecting a level of furanosyl borate diester in the sample may include converting furanosyl borate diester (AI-2B) to a fructose adduct AI-2B-fructose by reacting the sample with fructose; and detecting a level of AI-2B-fructose in the sample.

BRIEF DESCRIPTION OF THE DRAWINGS

In order to better understand various exemplary embodiments, reference is made to the accompanying drawings, wherein:

FIGS. 2A and 2B show HPTLC chromatograms at 254 nm and 365 nm, respectively. At both 254 and 365 nm, a new band is obtained for the chlorogenoborate sample. In the coffee bean extract with added boric acid the band corresponding to the chlorogenic acid turns bright blue in 365 nm UV light. In FIGS. 2A and 2B, bands corresponding to chlorogenic acid CA and chlorogenoborate DCB are marked;

FIG. 2C: UV densitogram for DCB (280 nm); and

FIG. 2D: UV densitogram for CA (280 nm); [BA: Boric acid; DCB: Chlorogenoborate diester complex; HPTLC: High-performance thin-layer chromatography; UV: Ultraviolet].

FIG. 3A: UHPLC/MS confirmation of the identified DCB in GCB extract (UHPLC Protocol B);

FIG. 3B: SIR m/z 715 chromatogram with the chlorogenoborate peak identified at 5.75 minutes (UHPLC Protocol B);

FIG. 3C: Mass spectrum of DCB semisynthetic standard (fragment ion m/z 715) with a small quinic acid fragment ion (m/z 191); and FIG. 3D: Mass spectrum of chlorogenic acid (fragment ion m/z 353), including a dimer (m/z 707);

FIG. 3E: Mass spectra for DCB standard;

FIG. 3F: Mass spectra for CA standard (DCB: Chlorogenoborate diester complex; GCB: Green coffee bean; MS: Mass spectrometry; SIR: Selective ion recording; UHPLC: Ultra-high-performance liquid chromatography);

FIG. 3G: UHPLC chromatograms in SIR mode for caffeine (RT 3.85) (Protocol A);

FIG. 3H: UHPLC chromatograms in SIR mode for CA (RT 3.30) (Protocol (A);

FIG. 3I: UHPLC chromatograms in SIR mode for DCB-rich natural extract (DCB RT 7.88);

FIG. 4A: DCB UV spectrum; and

FIG. 4B: CA UV spectrum (CA: Chlorogenic acid; DCB: Chlorogenoborate diester complex);

Figure 7A:
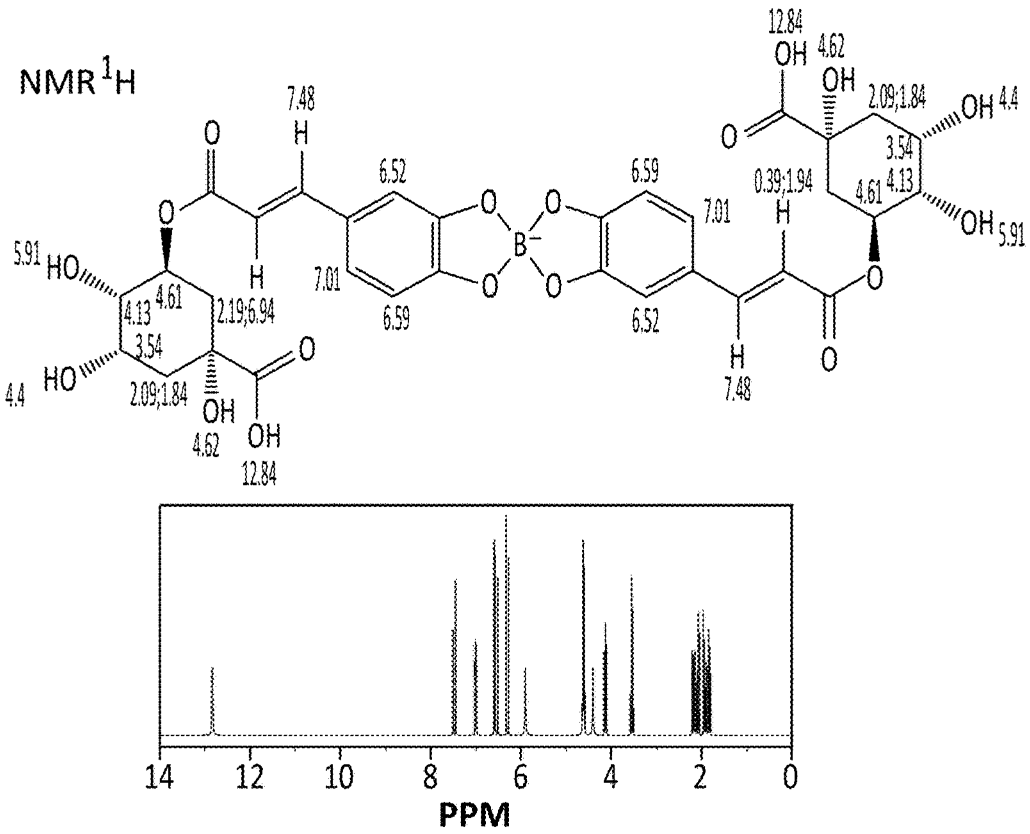
Figure 7B:
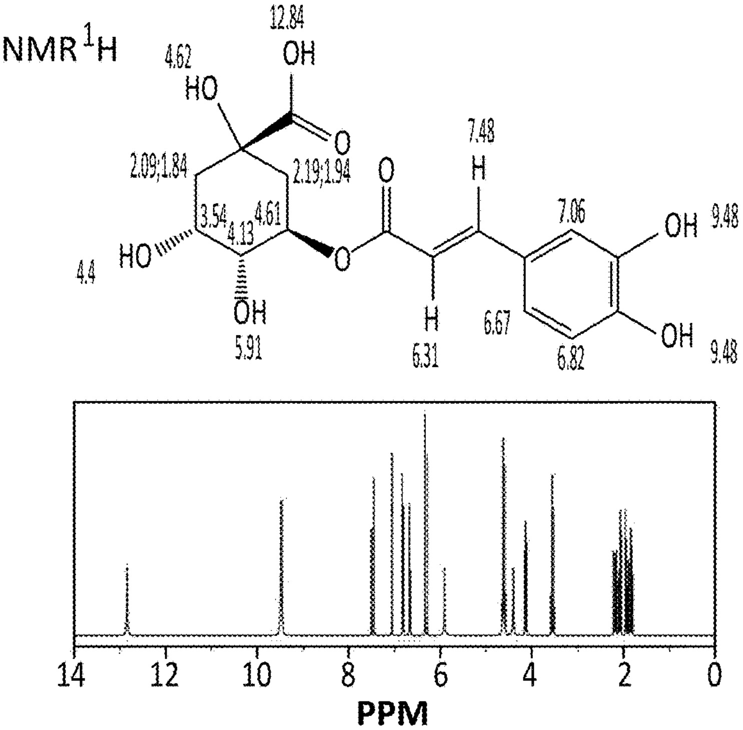
Figure 8:
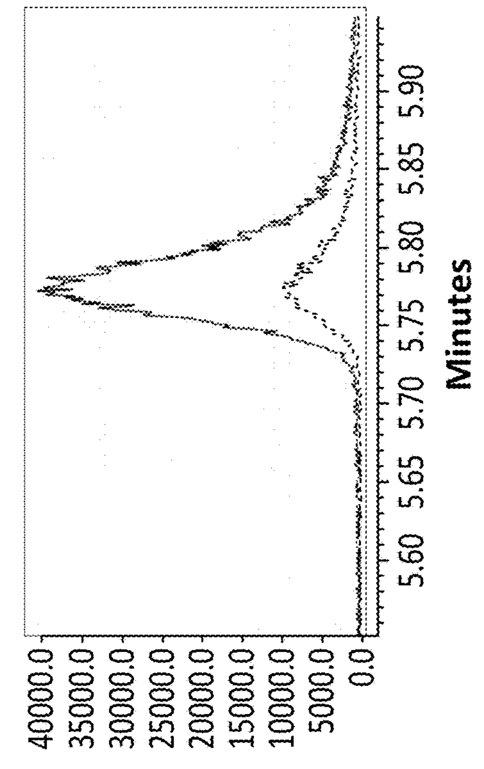
Figure 10:
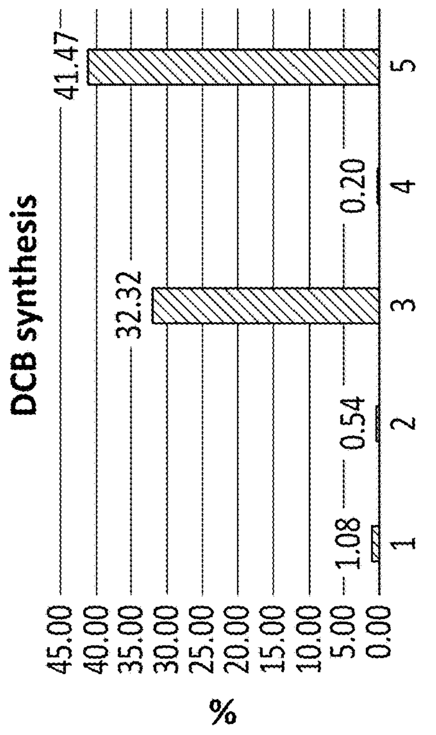
Figure 9:
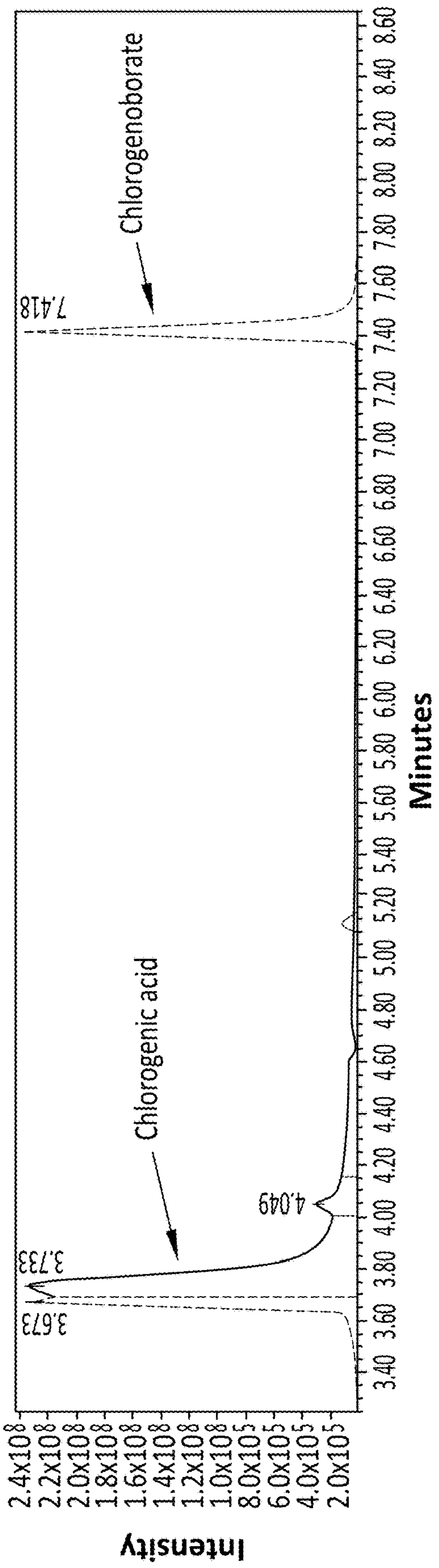
Figure 11:
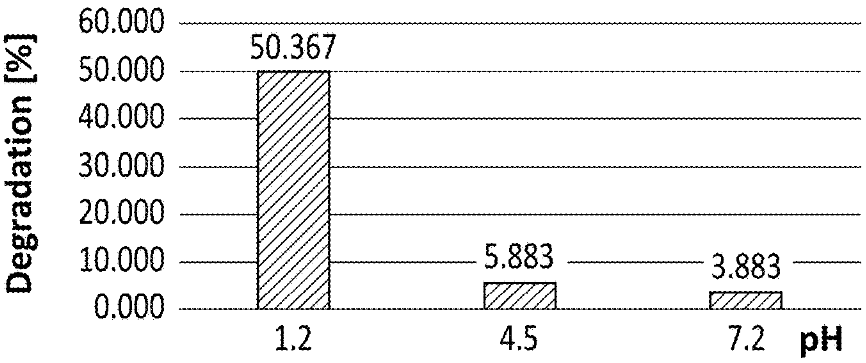
Figure 12A:
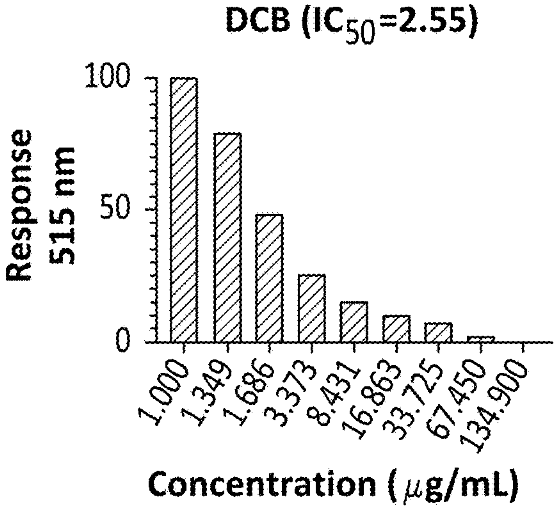
Figure 12B:
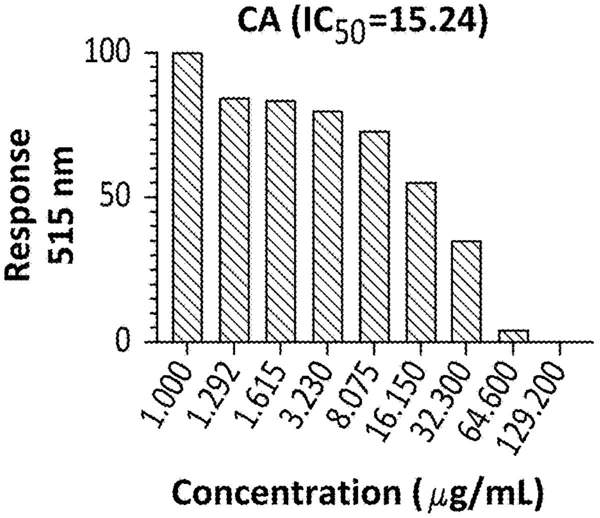
Figure 12C:
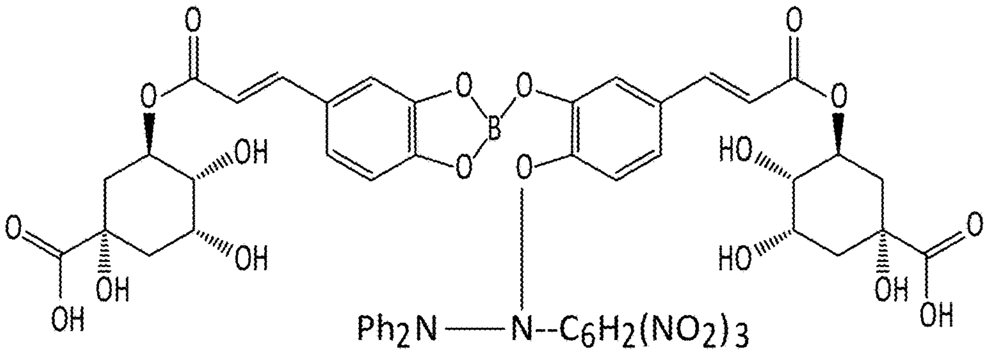
Figure 13A:
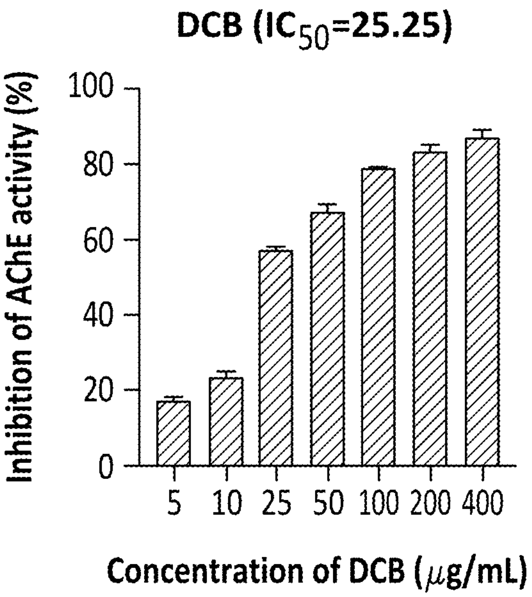
Figure 13B:
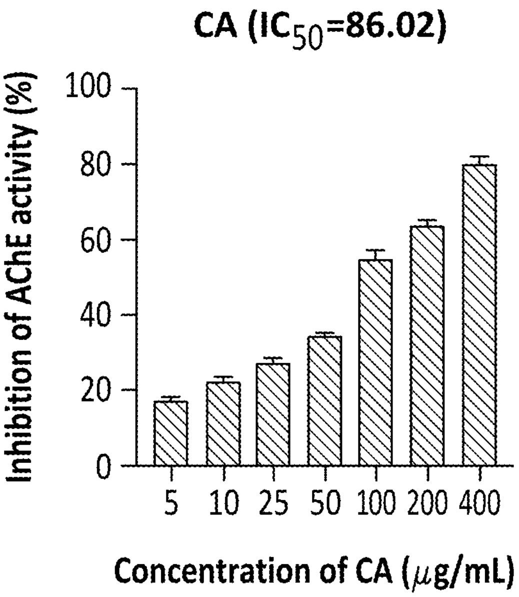
Figure 14:
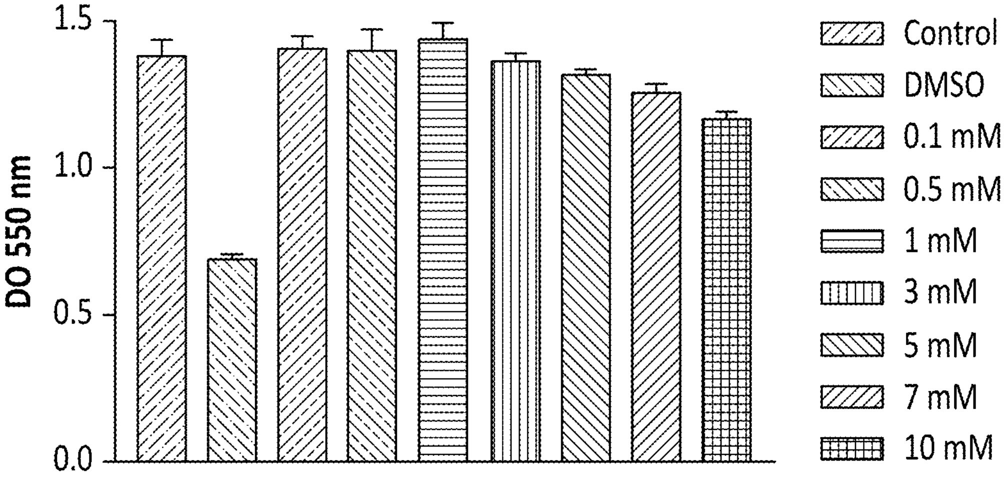
Figure 15:
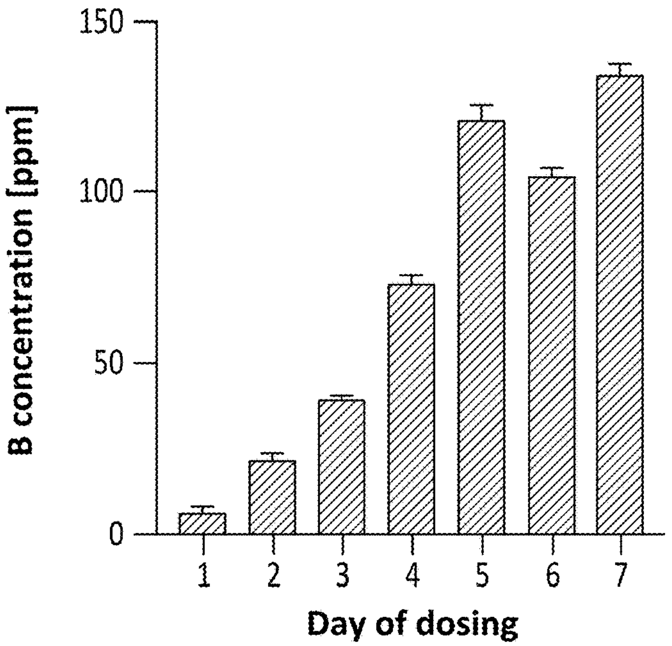

(A) α,β unsaturated aliphatic ester, C═O stretching of protonated carboxylic acid and some esters decompose (1737.51 $cm^{-1}$);

(B) Some esters decompose (1706 $cm^{-1}$);

(C) Presence of dimer of caffeic acid ester (1632.89 $cm^{-1}$);

(D) C≡C stretching (benzene moiety and acyclic chain) and in plane deformation modes or rocking mode for H—H bond (1521.59 $cm^{-1}$);

(E) Dimer of caffeic acid ester and >C═O stretching of carboxylic acid (1463.67 $cm^{-1}$);

(F) Rotation of phenyl CH (1396 $cm^{-1}$);

(G) Wagging modes of $CH_2$ group (1278.15 $cm^{-1}$);

(H) C—O stretching band of triglycerides, assigned to the esters formation (1162.68 $cm^{-1}$);

(I) C—O stretching band of triglycerides (1112.78 $cm^{-1}$);

(J) N/A;

(K) N/A;

(L) B—O bond (816.69 $cm^{-1}$); and (M) B—O bond (763.36 $cm^{-1}$) (DCB: Chlorogenoborate diester complex; FTIR: Fourier-transform infrared (spectroscopy); N/A: Not assigned);

FIGS. 6A to 6D show the molecular structures of (a) Quinic acid, (b) CA, (c and d) Newly formed DCB tautomers (CA: Chlorogenic acid; DCB: Chlorogenoborate diester complex);

FIGS. 7A and 7B show the $^1$H-NMR spectra of (a) DCB and (b) CA (CA: Chlorogenic acid; DCB: Chlorogenoborate diester complex; $^1$H-NMR: Proton nuclear magnetic resonance);

FIG. 8 shows DCB identified in GCB: SIR m/z 715 chromatogram with the chlorogenoborate peak identified at 5.75 minutes. The dashed chromatogram represents $^{10}$B, while the solid chromatogram highlights $^{11}$B. The ratio between the areas is approximately 1:5, which is corresponding to the specific boron isotope ratio (B: Boron; DCB: Chlorogenoborate diester complex; GCB: Green coffee bean; SIR: Selective ion recording);

FIG. 9 shows the CA (RT 3.6 minutes) and DCB (RT 7.4 minutes) UHPLC/UV chromatograms (CA: Chlorogenic acid; DCB: Chlorogenoborate diester complex; RT: Retention time; UHPLC: Ultra-high-performance liquid chromatography; UV: Ultraviolet);

FIG. 10 highlights the obtaining of semisynthetic DCB (CA:BA in at least 1:2 molar ratio):

(1) Rotary evaporated (solvent acetonitrile-water 1:1, v/v);

(2) Oven evaporated (solvent acetonitrile-water 1:1, v/v);

(3) Freeze dried (solvent water);

(4) Freeze dried with calcium (solvent water);

(5) Air evaporated (solvent water) (BA: Boric acid; CA: Chlorogenic acid; DCB: Chlorogenoborate diester complex);

FIG. 11 is the in vitro simulation of DCB digestion: stomach (gastric phase, at pH 1.2 and pH 4.5) and duodenum (small intestinal phase, at pH 7.2). (DCB: Chlorogenoborate diester complex);

FIG. 12A shows the DPPH antioxidant activity of DCB (DCB: Chlorogenoborate diester complex; DPPH: 2,2-Diphenyl-1-picrylhydrazyl; $IC_{50}$: Half maximal inhibitory concentration);

FIG. 12B shows the DPPH antioxidant activity of CA (CA: Chlorogenic acid; DPPH: 2,2-Diphenyl-1-picrylhydrazyl; $IC_{50}$: Half maximal inhibitory concentration);

FIG. 12C shows an adduct of the DPPH superoxide radical and the trigonal form of DCB;

FIG. 13A shows the Anti-AChE activity of DCB (AChE: Acetylcholinesterase; DCB: Chlorogenoborate diester complex; $IC_{50}$: Half maximal inhibitory concentration);

FIG. 13B shows the Anti-AChE activity of CA (AChE: Acetylcholinesterase; CA: Chlorogenic acid; $IC_{50}$: Half maximal inhibitory concentration);

FIG. 14 shows the in vitro cytotoxicity of DCB by MTT assay (DCB: Chlorogenoborate diester complex; MTT: 3-(4,5-Dimethylthiazol-2-yl)-2,5-diphenyltetrazolium bromide); and FIG. 15 shows DCB concentrations (expressed as boron amounts) in rats' feces (B: Boron; DCB: Chlorogenoborate diester complex).

Figure 16:
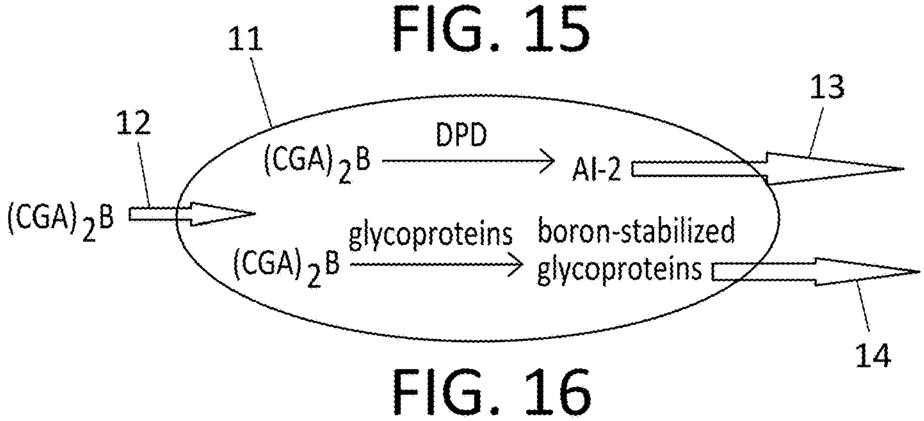
Figure 17A:
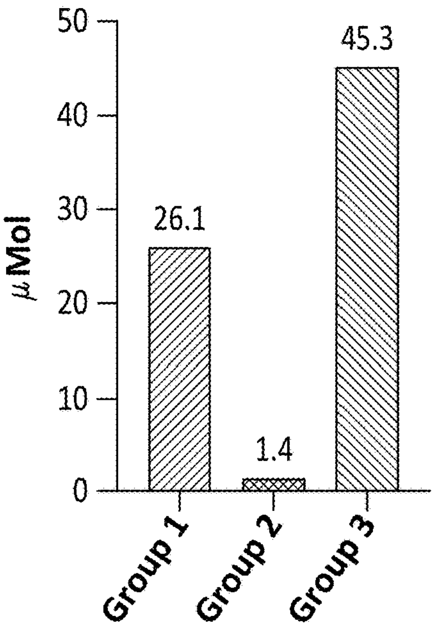
Figure 17B:
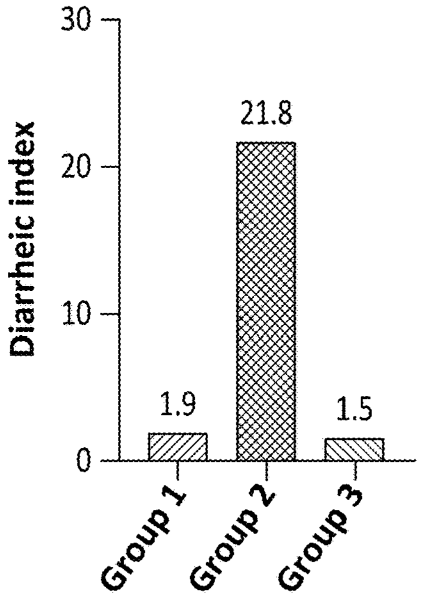
Figure 18A:
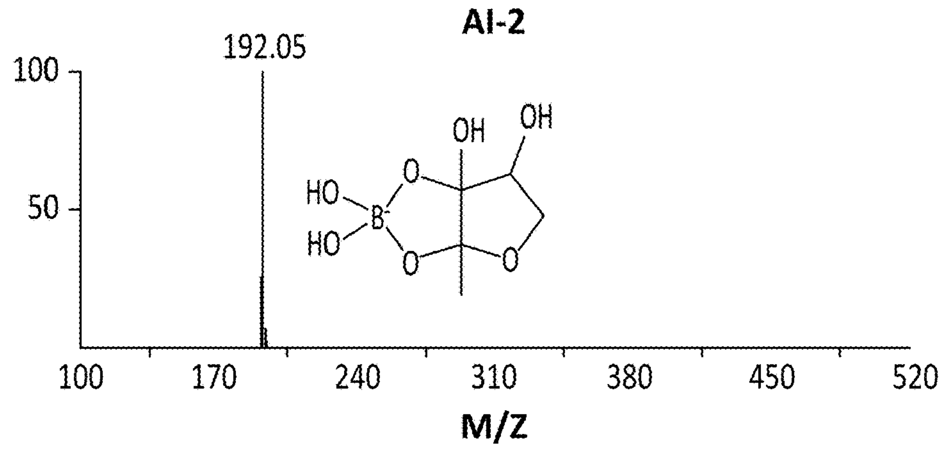
Figure 18B:
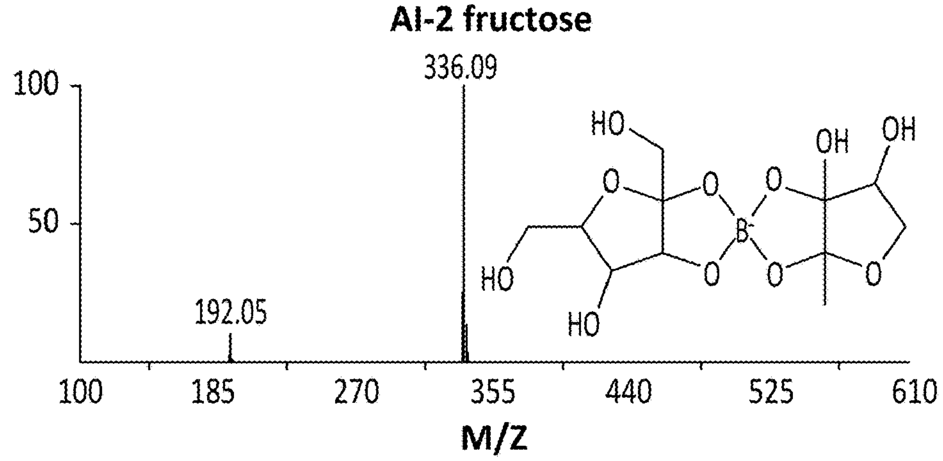
Figure 19:
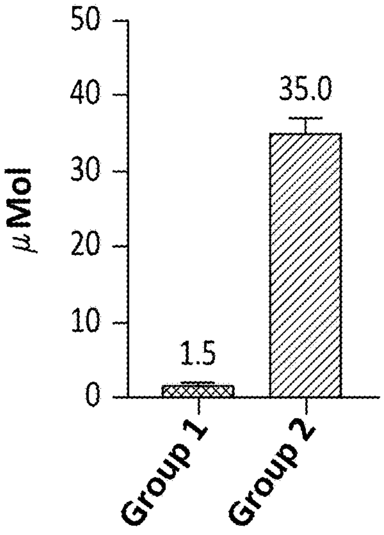
Figure 20:
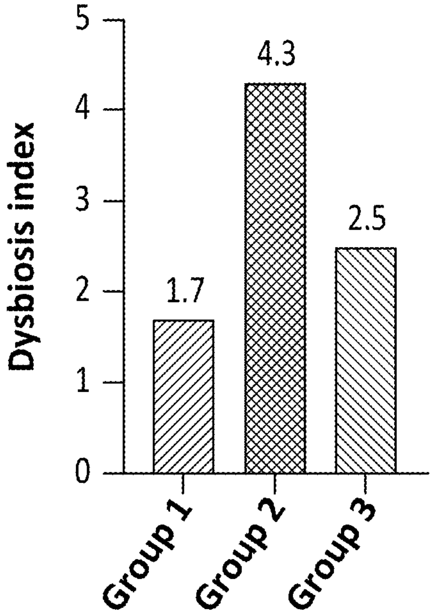

FIG. 16 shows the proposed mechanism of action of DCB;

FIGS. 17A and 17B show levels of AI-2B and diarrhea index in a rat model of castor oil-induced diarrhea, respectively. Group 1: Reference; Group 2: Castor oil-induced diarrhea; Group 3: DCB extract (15 ppm B) intake five days after diarrhea appeared. AI-2B: Autoinducer-2-borate;

FIGS. 18A and 18B show mass spectra of autoinducer-2-borate (AI-2B) and AI-2B-fructose complex, respectively;

FIG. 19 shows the level of AI-2B in the saliva. Group 1: Mechanical dental treatment; Group 2: Mechanical dental treatment and a mouthwash with DCB-rich natural extract;

FIG. 20 shows the DI in the stool of the patients with long-term antibiotic therapy supplemented with a DCB-rich natural extract. DI: Dysbiosis index.

DETAILED DESCRIPTION

Figure 6A:
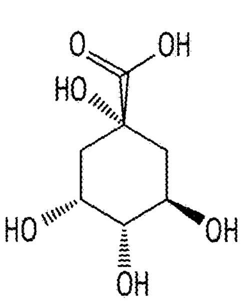
Figure 6B:
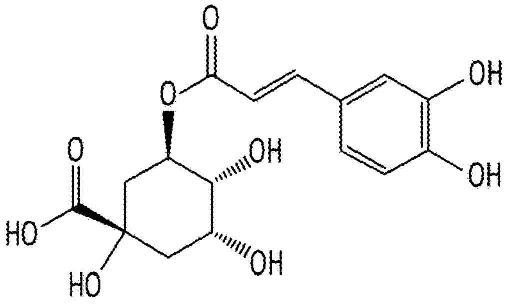
Figure 6C:
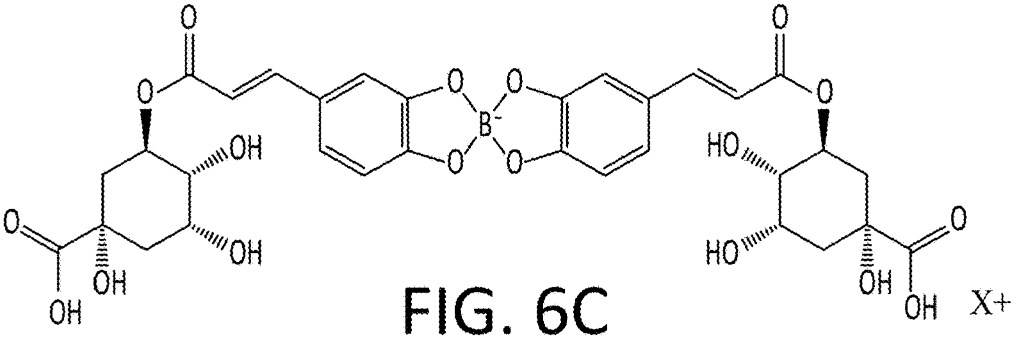
Figure 6D:
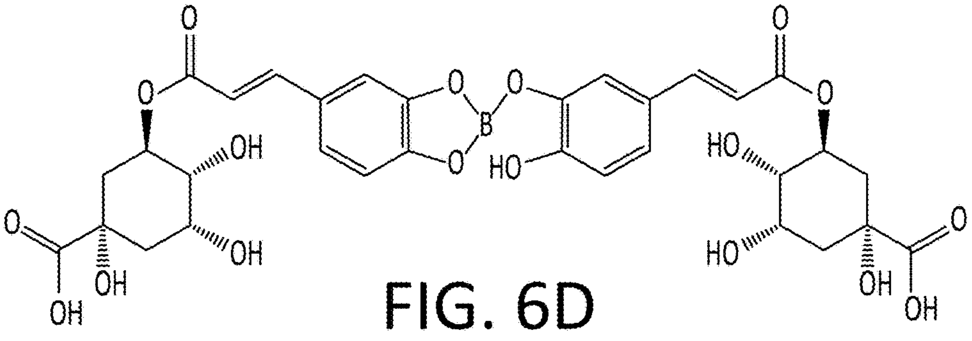

The term "green coffee bean" (GCB) refers to either immature coffee beans or even mature coffee beans which have not been roasted. Nonvolatile nitrogenous compounds (including caffeine, alkaloids, trigonelline, proteins and free amino acids) and carbohydrates are of major importance in producing the full aroma of roasted coffee and for its biological action. GCB are a rich source of the chlorogenic acid (CHL; FIG. 6B) and a 2:1 complex of chlorogenic acid and boric acid (diester chlorogenoborate DCB, which is synonymous with diester chlorogenoborate complex, CBDC; FIG. 6C (a borate anion, where $X^+$ is a pharmaceutically acceptable cation) or FIG. 6D)), which are associated with several beneficial health effects. A substantial portion of phytochemicals gets destroyed during heating and roasting of the coffee beans.

The term "prebiotic" is intended to mean a selectively fermented ingredient that allows specific changes, both in the composition and/or activity in the gastrointestinal microflora flora that confers benefits upon host wellbeing and health. Prebiotics act in the colon and produce changes in the microbial flora which affect energy metabolism and gut long-acting affect. These criteria of a prebiotic are as follows:

1) A prebiotic resists gastric acidity, mammalian enzyme hydrolysis and gastrointestinal absorption;
2) A prebiotic is fermented by the intestinal microflora;
3) A prebiotic selectively stimulates the growth and/or activity of intestinal bacteria associated with health and well-being.
4) A prebiotic is stable in food processing treatments. Specifically, prebiotics should be chemically stable in food processing treatments, such as heat, low pH, and Maillard reaction conditions, to reach their active form in the intestinal microflora.

A prebiotic, as defined herein, is a compound that is selectively utilized by host microorganisms conferring a health benefit, they are indigestible, and they do not dissociate at a pH of ~4.5 in the upper gastrointestinal tract. DCB is a novel prebiotic candidates. An increasing number of studies show that nutrition may influence gut microbiota and the human health is crucially dependent of the healthy microbiota. The prospective nutrition will be personalized depending on microbiota type for every human being. Thus, DCB will become essential for the personalized nutrition, as further novel prebiotic microbiota-accessible candidates, Prebiotics occur naturally in many dietary foods, such as asparagus, beets, garlic, chicory, onions, artichokes, wheat, honey, bananas, barley, tomatoes, rye, soy, human and cow's milk, peas, beans, green coffee, wine, seaweed, and microalgae.

In science, boron is considered a mineral with a role both in the origin and evolution of life, as well as a micronutrient with a beneficial role in human and animal nutrition. Thus, B falls in both directions of the definition of prebiotic, as necessary mineral in the appearance and evolution of life and as micronutrient with an important role in nutrition in plants, bacteria, fungi, animals, and humans.

Physiological essentiality and nutritional essentiality are two different concepts. Physiological essentiality means an indispensable material for life, while nutritional essentiality means an indispensable material in the diet. A substance is usually considered to be nutritionally essential if a substance deficiency from the diet results in a biological dysfunction. Intake of that substance prevents the biological dysfunction or makes it reversible. Nutritional essentiality was established about 100 years ago, based on the observation that certain pathologies can be stopped or reduced by including a specific food in the diet.

In the case of boron, boron has been recognized as a nutritionally essential micronutrient for plants and other organisms, in micromolar concentrations, for over a century. Boron is also a key element in the formation of a symbiosis between legumes and a group of bacteria called nitrogen-fixing bacteria (*Rhizobium, Azorhizobium* and *Bradyrhizobium*). Boron was claimed as an essential micronutrient (mineral) for the symbiotic interaction and development of bacterial nodules in vegetables, although these bacteria have not shown that boron is essential for them. These results suggest that when boron deficiency exists, or where insufficient boron levels are present, *rhizobia*-legume "chemical dialogue" fails, and the bacterium is recognized as a pathogen by the plant, with disastrous consequences for symbiosis. Subsequently, boron nutrition has a strong effect on *rhizobia*-legume symbiosis, affecting cell-to-cell signaling during the symbiosis stages.

In general, in symbiosis with other kingdoms, bacteria use the ability of boron to attach to glycoproteins, thus blocking the bacterium from infecting the host of the symbiosis. Among other roles, the presence of a capsule of bacterial extracellular polymeric substances (EPS) prevents attachment of host-legume glycoproteins to the bacterial cell surface. Boron could be involved in the production of EPS, and therefore low B-level bacteria strains would result in a low capacity for infection due to the absence of a suitable polysaccharide capsule. Boron-deficient bacterial strains showed an electrophoretic lipopolysaccharides (LPS) profile similar to that of mutants affected in LPS synthesis or polymerization.

The primary function of boron in plants is stabilizing cell walls by generating a borate diester via crosslinking of cis-diols of apiosyl residues between two rhamnogalacturonan II (RG-II) polysaccharides and this B/RG-II complex likely exists in all higher plants. Borate complexes with cis-diols are well-studied in marine bacteria where boron has a strong affinity for complexing siderophores that typically bind and solubilize Fe (III) for transport. For example, boron readily binds hydroxamates in vibrioferrin and rhizoferrin or the catechols in petrobactin, which may play key roles in cell signaling pathways upon binding of boron. The furanosyl borate diester (AI-2B) is produced by same bacteria to regulate activities associated with quorum sensing (QR), such as symbiosis, virulence, motility, biofilm formation and antibiotic production. Various borate polyketides display antibacterial, antiviral, or insecticidal activity, such as borophycin and the structurally similar siderophores boromycin, N-acetyl-boromycin, N-formyl-boromycin, desvalino-boromycin, TmcB transmembrane complex, aplasmomycin A, B, and C, monoacetyl-aplasmomycin and tartrolon B, C and E. These polyketides are hypothesized to be involved in the sequestration of boron in marine organisms that do not have boron transport proteins.

The main physiologically stable phyto-borate ester compounds are boron pectic RG-II polysaccharides, glucose- and fructose-borate esters, bis-sucrose esters, borate polyalcohols, and our recently discovered DCB. Boron organic species are present in plants in a large range of essential primary metabolites as boron-carbohydrate complexes, boron amino acids and secondary metabolites as organic acids and recently in vivo discovered as boron-phenol complexes or compounds (DCB). Phenolic acids are found in plants and exert a significant biological function in achieving communication between plants and other organisms. At the same time, the phenolic acids are acting on microbiota, through suppression of predators and pathogens, as well as through stimulating mycorrhizae.

Although boron is essential for plants, some bacteria, fungi, and algae, in terms of human health, its role is not yet defined in human and animal metabolism, as no biochemical molecule with boron or any metabolic pathway using boron has been discovered. Therefore, boron has not been classified as an essential nutrient for humans, as its biological function has not been clearly identified. However, boron has beneficial effects on biological functions, such as reproduction, growth, calcium metabolism, bone formation, energy metabolism, immunity, brain function and steroid hormones including vitamin D and estrogen.

At present, there is strong evidence for the importance of boron in the health of the microbiota. For chickens, it was observed that nutrition with boron (in the form of boric acid (BA) helped to maintain intestinal homeostasis, and control *Salmonella enteritidis* infection through the microbiota. In humans, a diet rich in boron has led to an improvement in the oral microbiota and, most importantly, a decrease in thyroid stimulating hormone (TSH), which is generally a consequence of dysbiosis. Increased boron in saliva has a beneficial effect on oral and dental health and can reduce the formation of cavities. Significant changes in TSH and salivary buffering capacity during a natural boron-rich diet are of clinical importance, dysbiosis being a common finding in thyroid disorders.

The most important biochemical change caused by a boron-rich diet was related to the lipid profile. Serum levels of LDL-cholesterol, VLDL-cholesterol, and triglycerides significantly decreased after consumption of a high-boron diet for one month. Emerging evidence suggests the important role of the microbiota in regulating dietary fat absorption and postprandial lipid metabolism. In the bacteria of the microbiota, the bacterial quorum-sensing signal compound AI-2B (furanosyl borate diester) contributes to the health of the intestinal flora or microbiota, and may protect against pathogens.

Commensal microbes may exert a protective role against infection by pathogenic bacteria. For example, AI-2B produced from the gut bacteria *Ruminococcus obeumcan* may suppress infection by the pathogen *Vibrio cholerae.*

In host physiology, these changes are most probably due to indirect effects of free boron that may stimulate the maturation of the gut, benefiting bacteria in symbiosis with the host metabolism.

After 5 days of feeding sheep with boron, the feces had a high concentration of B (250 ppm), higher than in the urine, proving that the colon microbiota has a high boron absorption capacity. The higher boron content in the feces is be explained by its availability for the microbiota. Boron is not being accumulated in any internal organ, but only in the intestine. The concentration of B in the rumen fluid was lower than in the feces. When indigestible boron reaches the colon, it interacts with the microbiota, thus stimulating apoptosis and cell proliferation. The proliferation of intestinal cells is determined by the relationship between boron and the microbiota.

As the mechanism of action of boron has not been identified in human/animal cellular metabolism, the market for boron nutraceuticals does not yet distinguish between organic boron compounds (e.g., SBEs, DCB) and inorganic boron compounds (boric acid (BA), borates). There is currently a major scientific gap between the use of boron compounds in human and animal diets and the mechanism of action of boron and its target in the body.

Currently, there are also organic boron compounds sold as dietary supplements: calcium fructoborate (CaFB), boron gluconate chelates, boron aspartate, boron citrate, boron ascorbate, boron glycinate and inorganic compounds, such as BA, sodium borate or sodium tetraborate decahydrate. All known forms of boron easily hydrolyzed in the intestine to BA. BA is reactive and tends to accumulate in tissues.

Boric acid is not metabolized by humans or animals and is excreted unchanged. Studies in both humans and other animals have shown that the absorption of BA is rapid following oral exposure, with 81-95% of the BA absorbed within 24-96 hours of ingestion. More than 98% of all forms of boron ingested (BA, sodium tetraborate) are absorbed as undissociated BA (NPIC, 2022). Boron citrate, boron aspartate, boron ascorbate and boron glycinate are digestible (having low association constants), are being degraded in the stomach and absorbed in the small intestine. Only a small amount of about 2-5% reaches the colon.

It is well known that boron forms very stable complexes with sugars, especially with fructose. CaFB is transformed in BA and fructose in the superior gastric system similar boron citrate, boron ascorbate, boron aspartate, boron glycinate. At the same time, during our experiments, we did not detect fructoborate (FB) anion in feces after an ingested nutrition of rats with 150 ppm of boron per day, for seven days. Other old studies show that FB is being identified in blood of rats fed by CaFB gavage.

New knowledge about the essentiality of boron species for a healthy symbiosis between human/animal hosts and microbiota will lead to the use of natural B-based nutraceuticals to target the human/animal microbiome (oral cavity, gut, vagina, skin, and scalp microbiomes). Of these, the gut microbiome is the most important for human health. Subsequently, boron species have become novel prebiotic candidates and target the colon as novel colonic foods. Moreover, boron species target colon nutrition, resulting in a healthy gut microbiome, as well as a healthy microbiome in the mouth, vagina, skin, and scalp.

Boron is an essential element for autoinducer-2 (AI-2) synthesis of QR system, which affects bacterial collective behavior. QR is the process by which bacteria communicate via secreted signals (AIs). The roles of QS are diverse and include population density detection, virulence, biofilm formation, and the maintenance of the stress response. AI-2 is not a single signaling molecule but a group of 4,5-dihydroxy-2,3-pentanedione (DPD) derivatives that can convert rapidly to one another. Two AI-2 forms engaged by corresponding bacterial receptors have been identified, including the born-containing DPD derivative S-2-methyl-2,3,3,4-tetrahydroxytetrahydrofuran-borate (S-THMF-borate; AI-2B) and the non-borated R-2-methyl-2,3,3,4-tetrahydroxytetrahydrofuran (R-THMF; AI-2). Nevertheless, bacterial species possessing the two different types of receptors can communicate with one another via AI-2 signaling due to rapid interconversion between AI-2 and AI-2B. Boron promoted biofilm formation by upregulating the expression levels of biofilm-related genes, improving the QS system AI-2 activity. It is known that addition of naturally occurring borate to an AI-2 precursor generates active AI-2B. AI-2 is being synthesized within bacteria (intracellularly), while AI-2B is being synthesized outside bacteria (extracellularly) in the presence of borate anion. A recent paper reviews the evidence supporting the essentiality of the boron species in the symbiosis between the microbiota and the human/animal host, with the stated aim of highlighting the mechanism of action and target of these species.

New insights into naturally organic boron (NOB) species essentiality to animals and humans were reported by us. All the known effects of boron on human/animal health can be explained by the essentiality of boron on healthy symbiosis. The mechanism of action of natural organic borate species (DCB) is related to both the boron signaling molecule (autoinducer-2 borate (AI-2B), as well as the fortification of the colonic mucus gel layer with boron species from boron-rich prebiotic diets. Both the microbiota and the colonic mucus gel layer can become DCB targets.

Subsequently, the key aspects of the boron species of DCB that will be in nutrition of the future are:

(i) DCB boron species to be potential prebiotic candidates;

(ii) DCB boron species are needed for the symbiosis between bacteria and human/animal hosts;

(iii) DCB boron species can be considered effective prebiotics when more than 95% of them reach the colon and do not dissociate in the form of inorganic boron;

(iv) DCB boron species to be the functions as carriers for (a) carbon to support microbiome growth; and (v) the essential boron element of DCB needed for healthy symbiosis.

Boron can be a micronutrient essential for symbiotic interaction between microbiota and a mammalian host for healthy humans and animals. The effects of insufficient boron levels in the microbiota could be:

(i) dysbiosis, an alteration of the symbiosis between the host (human/animal) and the microbiota, due to the deficiency of the AI-2B signaling molecule; and (ii) increased intestinal permeability and translocation of the intestinal microbiota from the intestinal lumen to the systemic circulation, due to the lack of boron in the structure of the mucin gel, which determines the interaction of bacterial biofilm directly with host cell membranes, and therefore their direct infection.

Consequently, the microbiota needs boron to achieve:

(i) biosynthesis of a furanosyl borate diester (AI-2B), a member of a family of signaling molecules used in quorum detection; and (ii) a protective barrier that separates the microbiota from the host (B prevents direct contact between bacteria and the host organism, thus preventing the occurrence of direct infectious effects).

Since the specialized literature mentions that the health of the human/animal organism depends on the health of the microbiota, we suppose that the role of boron becomes crucial for the health of the human/animal organism. The microbiota influences the whole health of the organism through the "axes" already formulated and studied in the literature: gut-brain axis, gut-immunity axis, gut-bone axis, gut-cartilage axis, gut-heart axis, gut-lung axis, gut-thyroid axis. Subsequently, if boron is essential for the symbiosis between microbiota and host, then boron has a beneficial role in preventing certain diseases, such as osteoarthritis (OA), osteoporosis (OP), rheumatoid arthritis, cardiovascular inflammation, depression, obesity, diabetes, viral, bacterial and parasitic infections, thyroid disease.

The recommended dosage of a GCB extract containing 50% chlorogenic acids is one capsule of 400 mg taken three times per day, based on the recommendation of a commercial manufacturer. Thus, the recommended daily dosage of chlorogenic acids is 600 mg (if taking 3 GCB capsules of 400 mg, each containing 50% chlorogenic acid). The GCB extract of the present invention contains 50% chlorogenic acids and 6.5% DCB, and the consumption of 1000 milligrams per day of extract is sufficient for the required boron intake. The recommended daily boron requirement is ca. 1 milligram boron/day (calculated for the microbiota and gel mucus layer content our estimates that the for the microbiota for AI-2B synthesis and for mucus gels layer structure).

The total chlorogenic acid content of green *Arabica* beans is typically 6.9% and in the *Robusta* variety it is typically 10%. A number of different chlorogenic acids are present, but 5-mono-caffeoylquinic acid is present in the largest amount. Dicaffeoyl and feruloyl quinnic acids are also present, together with the 3 and 4-isomers of mono-caffeoylquinic acid. Apart from chlorogenic acids, the main acids present in significant quantities are quinic, malic, citric, lactic, pyruvic, succinic and glycolic acids. Moreover, green coffee beans typically contain 1.3% diterpenes in *arabica* and 0.2% diterpenes in green *robusta*. Various sterols and tocopherols are also present in the lipid part of green coffee beans. Trigonelline, an alkaloid which is a product of niacin metabolism, is also found in coffee beans. Trigonelline is present at 1.1% is *arabica* and 0.65% in *robusta*, and is a plant alkaloid with therapeutic potential for diabetes and central nervous system disease.

Chlorogenic acid is the main phenolic acid in coffee and a very important anti-oxidant. Chlorogenic acids in coffee are mainly mono- and di-esters of quinic acid and phenolic compounds (e.g. caffeic, ferulic, coumaric, and methoxy-cinnamic acids) attached to different positions. They have important health benefits, as below:

i. Anti-Oxidant activity;
ii. Anti-mutagenic effect;
iii. Anti-acid activity;
iv. Anti-Obesity activity;
v. Anti-hypertensive activity;
vi. Anti-diabetic activity; and
vii. Activity improving metabolic gut microbiota.

Chlorogenic acid has antimicrobial activity against a wide range of organisms, including bacteria, yeasts, molds, viruses, and amoebas. These antimicrobial properties can be useful for the food industry in its search for new molecules for the preservation of food products. The combination of these properties makes chlorogenic acid an excellent candidate for the formulation of dietary supplements and functional foods.

A new natural compound of boron, chlorogenoborate diester (DCB, FIG. 6C or 6D) was detected and quantified in green coffee beans. DCB is a borate complex of chlorogenic acid, formed by esterification of boric acid and the phenolic hydroxy groups on chlorogenic acid. The compound DCB has been synthesized in the laboratory, and the present disclosure sets forth the method of synthesis to obtain a purified DCB synthetically.

DCB may be prepared in stable form by direct reaction of chlorogenic acid and boric acid. Chlorogenic acid is obtained by extraction from green coffee beans. Powdered coffee beans 1 may be extracted with water, methanol, acetonitrile, or mixtures thereof. The polar compounds thus are extracted into the solvent mixture. A chlorinated solvent, e.g., chloroform or methylene chloride, is used to remove caffeine. The aqueous layer is acidified and extracted with n-butyl alcohol, ethyl acetate, or similar solvent to extract the chlorogenic acids. The resulting extract is concentrated to dryness to obtain a chlorogenic acid extract.

A mixture of the chlorogenic acid extract and boric acid is dissolved in acetonitrile, water, or a mixture thereof and mixed at 65 grade° C. for 3 hours. The solvent is evaporated to produce a crude DCB product. DCB was recovered in this procedure (40% yield) together with unreacted chlorogenic acid. The chlorogenoborate complex DCB is readily separated from unreacted chlorogenic acid by chromatography, ion exchange chromatography, or solvent extraction to obtain pharmaceutical-grade DCB.

Boron phenolic complexes, such as DCB, are promising prebiotic candidates. Since the pKa of DCB is around 4.0, it is indigestible at a pH above the postprandial pH (4.5) of the stomach. In the human cell, there are no known biochemical mechanisms that require boron and, therefore, boron has not found a specific status in the world of nutraceuticals. As the mechanism of action of boron has not been identified in human/animal cellular metabolism, the market for boron nutraceuticals does not yet distinguish between natural organic boron compounds, e.g., sugar borate esters, DCB, and natural inorganic boron compounds, e.g., boric acid, inorganic borate salts.

However, in bacteria present in the mammalian intestine, borates are used to produce the signaling molecule furanosyl borate diester (AI-2B) from AI-2. AI-2B contributes to the health of intestinal flora and offers protection against pathogens. Because the organic borate ester AI-2B is similar to AI-2, they may also cause probiotic capabilities in some bacteria in the microbiota, and reduce virulence of bacterial pathogens.

The colon is considered the optimum place of absorption to improve the bioavailability of nutraceuticals and prebiotics due to its distinct features, including almost neutral pH, low enzymatic activity, and a long transit duration. Nutraceuticals should be preserved in the rough medium of the superior GI tract and then they should be released into the colon to achieve a successful distribution in the colon and to obtain their full bioavailability. Considering that boron compounds are essential for a healthy relationship between microbiota in the intestine and the human/animal host, boron compounds are promising prebiotic candidates in human and animal nutrition. The health of the human/animal organism depends on the health of the microbiota, so that organic boron species role become crucial for the health of the human/animal organism.

Boron compounds increase the buffering capacity of saliva, have a positive impact on the intestinal and oral microbiome, protect the important probiotic bacteria *Bifidobacterium* spp. and *Lactobacillus* spp., improve short-chain fatty acid (SCFA) production, and are essential for improving the integrity and impermeability of the intestinal barrier. Boron compounds also improve the immunity, anti-inflammatory, and antioxidant actions of the microbiota. The microbiota influences the health of the body through the "axes" already formulated and studied in the literature: gut-brain axis, gut-immunity axis, gut-bone axis, gut-cartilage axis, gut-heart axis, gut-lung axis, gut-thyroid axis. This may explain the beneficial role of boron in preventing certain diseases, such as: osteoarthritis, osteoporosis, rheumatoid arthritis, cardiovascular inflammation, depression, obesity, diabetes, viral and bacterial infections, and thyroid diseases.

New insights into boron essentiality to animals and humans show that a new concept in boron science is needed to explain the mechanism of action of boron in their health. The organic DCB is essential for human/animal host healthy microbiome symbiosis. Inorganic boron species, e.g., boric acid, borax, and inorganic borate salts are not prebiotics, as they are digestible and soluble. Boric acid and related species are highly available in the bloodstream, while DCB is indigestible and reach the colon, where they may be incorporated into the microbiota. Inorganic boron species have been shown to have cytotoxic and genotoxic activity toward microorganisms in the microbiota.

From the practical point of view, the essentiality of natural organic borate species will open up new opportunities for supplementing boron in animal nutrition to stay healthy and live long. New knowledge about the essentiality of boron species for a healthy symbiosis between human/animal host and microbiota will lead to the use of natural boron-based nutraceuticals to target the human/animal microbiome (gut, oral, vaginal, skin, and scalp microbiome). Out of these, gut microbiome is the most important for human health. Subsequently, DCB become novel prebiotic candidates and are targeting the colon as novel colonic foods. Moreover, DCB target the colon nutrition, resulting in a healthy gut microbiome, as well as a healthy microbiome in the mouth, vagina, skin, and scalp.

Boron fortification is the practice of deliberately increasing the content of an essential boron micronutrient, boron organic species), in a food, so as to improve the nutritional quality of the food supply and provide a public health benefit with minimal risk to health.

Boron bio-fortification is the process by which the boron nutritional quality of food crops is improved through agronomic practices, conventional plant breeding, or modern biotechnology. Bio-fortification differs from conventional fortification in that bio-fortification aims to increase nutrient levels in crops during plant growth rather than through manual means during processing of the crops. Bio-fortification may therefore present a way to reach populations where supplementation and conventional fortification activities may be difficult to implement and/or limited.

Boron colonic foods are those for which there are no metabolizing enzymes available in the small intestine. Primary examples include DCB. Current guidelines for intake of colonic food are 10% of ingested calories or 20% of total food.

New insights into the essentiality of natural organic borates for healthy symbiosis between the human/animal host and the microbiota will determine the use of natural DCB-based nutraceuticals to target the colon (colonic foods). The mechanism of action of DCB species is related to both the boron signaling molecule (AI-2B), as well as the fortification of the colonic mucus with boron from the specific prebiotic diet.

Boron can be a micronutrient essential for symbiotic interaction between bacteria in the microbiota and a mammalian host, for healthy humans and animals. The microbiota, especially in animals, e.g., pigs, chickens, and ruminants, was influenced by the mineral boron as a micronutrient. The health of the microbiota was positively correlated with a high concentration of boron in the excreted feces.

When boron intake is going directly in the colon in an indigestible form, e.g., as a prebiotic dietary supplement, such as CDBC, then boron level in feces is not correlated with boron levels in the body of the host organism; rather, boron level in feces is correlated with a boron level in the microbiome, including boron levels in bacteria in the gut and in the mucin gel layer in the intestine. High boron levels in the feces after administration of indigestible boron compounds is indicative of a healthy symbiotic relationship between bacteria in the microbiome and the host organism. When boron intake is digestible, e.g., inorganic boric acid or borates, then the boron level in urine and blood is correlated with elevated boron levels in the host organism, e.g., an animal or a human, and may become potentially toxic for the host.

Boron is a prebiotic micronutrient, essential for the healthy microbiota of humans/animals. Its essential role is resulting from numerous scientific experiments that have proven the following:

- boron increases the buffering capacity of saliva
- boron has a positive impact on the intestinal and oral microbiome;
- boron protects important probiotic bacteria, *Bifidobacterium* spp. and *Lactobacillus* spp.;
- boron improves short chain fatty acid (SCFA) production in the microbiome;

boron is essential for improving integrity and impermeability of the mucin gel in the intestinal barrier between the microbiome and the intestinal wall; and boron improves the immunity, anti-inflammatory and antioxidant actions of the microbiota.

The intestinal microbiota (IM) is being spread within the whole GI tract in a heterogeneous way and means an ecosystem with 1.5 kg weigh, being formed of more 1500 bacteria and more 1000 other species (for instance: viruses, fungi, parasites, phages, archaebacteria). The most important healthy bacterial phyla of IM are Firmicutes and Bacteroidetes, followed by Fusobacteria, Actinobacteria and Proteobacteria. Since the most important species are *Faecalibacterium, Bacteroides* and *Bifidobacterium*, IM achieves several functions, such as maintaining metabolic homeostasis, nutrients' absorption, defense against infections, and the development of mucosa and systemic immunity. AI-2B could influence bacterial behaviors in order to maintain balance between Bacteroidetes and Firmicutes species. AI-2B is generated by multiple bacterial phyla found in the GI tract, such as *Bacteroides* spp., *Eubacterium* rectale, *Ruminococcus* spp. and *Lactobacillus* spp.

These remarks helped hypothesizing that AI-2B is a signaling molecule that might regulate bacteria, community dynamics and behavior in the microbiota and could also modulate the composition of the microbiota under dysbiosis conditions. The AI-2B production by one phyla may affect the expression of genes of other species and can promote communication between species, allowing bacteria to change their behavior, namely virulence, luminescence, and biofilm formation between different species. This feature makes AI-2B a great candidate for modulating interactions between cells in mammalian intestines, where thousands of bacterial phyla coexist and communicate. An example of the protective role of commensal microbes against pathogenic bacteria is the following: AI-2B produced from *Ruminococcus* obeum can confuse *Vibrio cholerae*, resulting in premature repression of AI-2B quorum sensing-mediated virulence and decreased colonization in the intestine.

When discussing boron essentiality, we must consider not the element itself, but molecular species. A few essential boron species were detected in bacteria (AI-2 furanosyl borate diester), fungi (as borate esters of carbohydrates) and in plants (as borate esters of carbohydrates and DCB). Essentiality should be correlated with one specific kind of speciation for the same element. In our view, boron natural organic complexes (e.g. ramnogalacturonan II, SBEs, organic polyhydroxy acid borate esters, bis-sucrose borate complexes, amino acid borate esters and DCB) may be prebiotic candidates in human/animal nutrition. This is different from the BA/borates which cannot be prebiotic compounds, since these inorganic compounds are digestible and toxic to the microbiota. In general, in the stomach acidic medium, soluble and insoluble organic boron species degrade into boron monoesters and diesters. Since natural boron monoesters and diesters (polyalcohols, organic acids sugars,) have pKa from 2.5 to 5, many of these do not degrade and therefore they remain mainly in organic form of B. At the same time, because BA can be easily associated with cis-diol sugars (fructose, ribose, glucose, phenolic acids), probably that in the superior part of the digestive tract the organic boron species are reconstituted even at pH 4 (postprandial).

Based on analysis of animal studies, it may be that at the beginning of a boron diet containing DCB, there is an increase of boron concentration in feces, which may be explained by indigestibility of DCB. Boron is released into the colon, where the microbiota uses it. An in vivo study shows the ability of a protein concentrates additive, enriched in borates, to diminish the toxic effect of a corn-based diet contaminated with *Fusarium* toxins in starter pigs. Boron has been hypothesized to have stimulated the activity of intestinal microflora, knowing that mycotoxins can disrupt the intestinal microbiota by altering the relative abundance of the commensal bacteria. The natural explanation for these experiments was: the human/animal body did not need boron, but the intestinal microbiota needed boron to create a healthy symbiotic relationship with the host.

Subsequently, the mechanism of action of boron phenolic compounds is the following: supply with boron phenolic compounds allows species of bacteria that require boron to communicate using AI-2B, and the fortification of the colonic mucus layer with organic boron esters, e.g., borate ester of glycoproteins, helps to protect the host from bacterial infection. Consequently, boron phenolic compounds are a source of boron, essential for symbiosis, and a source of carbon for the specific nutrition of the microbiota.

Giving the above-mentioned mechanism of action, both microbiota and the gel layer of the colonic mucus become the BPCs target. Therefore, in the future, BPCs may become promising novel prebiotic candidates. For instance, in the acidic gastric environment, the BPCs (i.e., chlorogenoborates) have about pKa 4.0, so these do not dissociate in the postprandial upper gastric system. In addition, indirect evidence of boron presence in the gel layer of colonic mucus is the boron "sequestration" in the colon during boron nutrition in animals.

Prebiotic Compositions of Invention

The instant invention is based on the discovery that boron is essential for symbiosis between the microbiota and the human or animal host and that the following classes of DCB are prebiotic candidates because it does not degrade in the upper gastric system and the symbiosis between the microbiota and the human/animal host needs boron as an essential element for a healthy symbiosis. The composition of the present invention may be administered by various routes including but not limiting to topical, oral, buccal, sublingual, parenteral, rectal, and inhalation. The composition may be in the form of a dosage form that includes but is not limited to powders, pills, tablets, pellets, capsules, thin films, solutions, sprays, syrups, linctus's, lozenges, pastilles, chewing gums, pastes, vaporizers, suspensions, emulsions, ointments, creams, lotions, liniments, gels, drops, topical patches, buccal patches, injections and the like. Typically, the composition further comprises at least one pharmaceutically acceptable excipient.

The composition of the present invention can be used in any application in which administration of the composition to a subject provides beneficial health effects. Suitable applications for administration of the composition include, but are not limited to, preventing oxidation (antioxidant activity), controlling and/or reducing body weight, controlling and/or reducing body mass index, controlling and/or reducing obesity, management of hyperlipidemic conditions, reducing oxidative stress, maintaining a healthy lipid profile, regulating blood glucose levels, treatment of liver cirrhosis, treatment of atherosclerosis, and treatment bacterial infection. The composition of the invention may be administered to reduce low density lipids. The composition of the invention may be administered to increase high density lipids. The composition of the invention may be administered to reduce low density lipids and increase high density lipids. Significantly, the composition is non-toxic and non-mutagenic.

The compositions of the invention can be administered to treat obesity in a subject. The compositions of the invention can be administered to reduce body mass index in an obese subject. The compositions of the invention can be administered to reduce body mass index in an overweight subject. The compositions of the invention may be administered to control or prevent weight gain in a subject. In some aspects of the invention may be administered to maintain or achieve a healthy weight in a subject. The compositions of the invention can be administered to reduce body fat in an obese subject. The compositions of the invention can be administered to reduce body fat in an overweight subject. The compositions of the invention may be administered to control or prevent body fat gain in an obese subject. The compositions of the invention may be administered to control or prevent body fat gain in an overweight subject. The compositions of the invention may be administered to control or prevent body fat gain in a healthy weigh subject.

Some diseases may be treated by manipulating the microbes within a person's gut through a DCB-rich diet. The gut microbiota has been defined as a 'vital organ', with its involvement with other organs establishing a link or a bi- or multidirectional communication axes between the organs via neural, endocrine, immune, humoral, and metabolic pathways.

The mechanism of action of DCB species may be primarily related to the boron-containing signaling molecule AI-2B, but also may involve fortifying the colonic mucus with boron from prebiotic DCB-containing diet. The key aspects of DCB use in nutrition are:

(i) DCB is a novel and potential prebiotic candidate;
(ii) DCB is needed for the symbiosis between bacteria and the human/animal host, is not necessary for human cell metabolism;
(iii) DCB can be considered an effective novel prebiotic because more than 95% of DCB reaches the colon, and DCB does not dissociate to form inorganic borates or boric acid;
(iv) boric acid, borax and inorganic borate salts are not prebiotics because a) they are digestible, leading to boron dissociation, and b) they have shown cytotoxic and genotoxic activity for microbes in the microbiota (boric acid is highly available in the bloodstream, while DCB is indigestible and therefore reaches the colon); and
(v) DCB is likely to function as carrier for: (a) carbon to support microbiome growth and
(b) the essential boron element needed for healthy symbiosis.

From the practical point of view, DCB will open up new opportunities for supplementing boron in human/animal nutrition to stay healthy and live long. New knowledge about the essentiality of DCB for a healthy symbiosis between human/animal host and microbiota will lead to the use of DCB-based nutraceuticals to target the human/animal microbiome, particularly in the gut, oral cavity, vagina, skin, and scalp. Out of these, the gut microbiome is the most important for human health. Subsequently, DCB becomes a novel prebiotic candidate, and may be used for targeting the colon as a colonic food. Moreover, DCB targets the colon nutrition, resulting in a healthy gut microbiome. DCB may be used to create a healthy microbiome in the mouth, vagina, skin, and scalp. The prospective nutrition will be personalized depending on microbiota type for every human being, Thus, DCB will become essential for personalized nutrition, as a further novel prebiotic microbiota-accessible candidate.

Supplements containing DCB may be taken preventively at any time, because these supplements ensure the capture and extinction of increased radiation from the living environment. Therefore, these supplements are effective as chemical protection against radiation, particularly natural radioactivity in soil and water. The gut microbiota and its associated metabolites play a central role in protecting against high dose radiation. A group of mice that was found to be resistant to radiation had two main important families of bacteria, Lachnospiraceae and Enterococcaceae, in their gut. Both the Lachnospiraceae and Enterococcaceae families of bacteria communicate by the AI-2B signaling molecule, a furanosyl borate diester.

Without being bound by any theory, the mechanism of action of boron proposed for natural organic borate complexes, such as DCB, is related to both the boron signaling molecule, i.e., AI-2B, as well as the fortification of the colonic mucus with boron from the prebiotic compound DCB. Such a mechanism is shown in FIG. 16, where the diester DCB is represented as $(CGA)_2B$. The ester $(CGA)_2B$ is incorporated into a bacterial cell 11 as shown at 12. In the cell, the $(CGA)_2B$ may react with 4,5-dihydroxy-2,3-pentanedione (DPD) or a hydrate thereof, producing the signaling compound AI-2B, which may the leave the cell 11 (13) and enter the microbiome. AI-2 then participates in intracellular communications with other symbiotic bacteria within the microbiome. In the cell 11, the (CGA)2B may react with glycoproteins to produce borate-stabilized glycoproteins. These borate-stabilized glycoproteins may remain within the cell 11, or exit the cell (14) and enter the mucin gel layer in the gut, protecting the integrity of the gut wall within the host organism. Alternatively, (CGA)2B may enter the mucin gel layer, and react with glycoproteins in the mucin gel layer. Similar mechanisms may occur where DCB enters the microbiome in other mucosal surfaces.

A healthy colon could explain why these complexes, DCB and AI-2B, provide protection against radiation. This is because the relationship between "good" bacteria from the colon and radiation resistance is already known. It is also already known that soils and plants containing a large amount of boron have low radioactivity, due to the absorption of neutrons from radioactive degradation and from blocking specific fusion reactions producing radiation dangerous to humans and animals. Also, in areas where the natural radiation of the soil is increased, the level of boron in the blood of humans and animals is low, since boron in the body is consumed by natural radiation from the environment and transformed into lithium and helium. In these areas, people have very advanced osteoarthritis (over 70%). Granulocyte colony-stimulating factor (GCF) and Entolimod are the only drugs that have been approved by the US Food and Drug Administration (FDA) as an effective countermeasure for high-dose radiation exposure, but they are expensive and have potential side effects. Therefore, DCB could successfully be targeted as a nutraceutical ensuring protection against radiation.

The difference between the sexes at the level of the microbiome also translates into different dietary requirements for boron between the sexes. Thus, women are more susceptible to diseases that are caused by insufficient boron in their diet. Monitoring boron levels and/or the AI-2B biomarker in feces will open new scientific horizons for monitoring the prophylaxis of diseases due to boron deficiency in food. Differences in the gut microbiome between the sexes are partly driven by sex hormones, which in turn contribute to differences in immunity and susceptibility to a multitude of chronic infections and diseases between men and women. Several disease conditions have been explored in relation to the intestinal microbiome and sex differences, including osteoarthritis, osteoporosis, periodontal disease, ovarian cancer, polycystic ovary syndrome, obesity, inflammatory bowel disease, diabetes, fatty liver disease, allergic diseases, and cardiovascular diseases.

There are differences in the level of boron in the hair in men and women, with women having almost two times less boron in their hair. DCB species causes an increase in the level of volatile fatty acids, due to an increase in the activity of commensal bacteria, especially the level of acetates. Also, a link between boron deficiency and osteoarthritis has been suggested. People with osteoarthritis have been reported to have lower stores of boron in their bones than people without the disease. Susceptibility to certain diseases can be ameliorated by high-boron nutrition. In areas with high boron in soil and water, osteoarthritis and osteoporosis have a very low incidence. Boron supplementation in postmenopausal women has been reported to increase the serum concentrations of 17β-estradiol and testosterone.

In the body, a chlorogenic acid/borate complex cannot be digested by mammals. However, boron in the chlorogenic acid/borate complex can be utilized by bacteria in the microbiome. Boron is used to form boron-carbohydrate complexes, including for AI-2 signaling molecule synthesis and boron-glycoprotein complexation. Further, boron may contribute to growth of the mucin gel layer between the microbiome and the wall of the intestine. Certain pathogenic bacteria that do not use boron in communication have been shown to be directly inhibited by the presence of boron. AI-2B produced by nonpathogenic bacteria (*Ruminococcus* obeum) has been shown to reprime the virulence of the pathogenic bacteria (*Vibrio cholerae*). The complexation between boron and CA is synergistic. The complex allows for effective transfer of the complex to the gastrointestinal tract where the complex is locally dissociated to deliver CA for effective metabolism into active metabolites for anti-inflammatory properties. Further, boron is also dissociated and delivered in the colon to support healthy microbiota that in turn helps metabolize CA more productively into metabolites. A healthy microbiota is hypothesized to produce organic acids, e.g., short chain fatty acids, that form esters with boron for better absorption and efficacy.

Various embodiments disclosed herein relate to an extract from green coffee beans with a high content of chlorogenic acid and from about 4% to 7% DCB, which has anti-oxidant, anti-tumor, anti-obesity, anti-hypertensive, antacid and anti-diabetic properties. The extract may be used as a prebiotic dietary supplement and a functional food. The extract contains DCB in a significantly higher concentration (6.5%) than present in extracts obtained by prior art methods, which generally contain only chlorogenic acids (CHL). The extract is obtained by extraction of green coffee beans with processes using specific solvents which are less polar than ethanol, and/or water immiscible solvents. Solvents such as n-butyl alcohol, ethyl acetate, or acetone are used at specific stages of extraction/purification of the green coffee bean extracts. As a result, the final extract is highly enriched with CHL fractions and DCB. The resulting extract is rich in DCB and chlorogenic acids, and is beneficial for colon health and for a healthy microbiome. In various embodiments, the extract contains up to 50% chlorogenic acids, and from 4% to 7%, from 4.5% to 6.5%, or from 5% to 6% DCB.

A final object of the present invention is to provide an improved extract from green coffee beans which has greater ability to quench oxidative stress and destroy free radicals, which contains boron as an essential element for a healthy symbiosis between a host organism and the microbiome. Conventional green coffee bean extracts contain polyphenols, but lack boron and therefore are less beneficial for the microbiome.

Applications of DCB

The claimed health benefits of the borate ester DCB come mainly from the ability of DCB to increase the proliferation of beneficial organisms in the colon, to inhibit the growth of potentially pathogenic microorganisms, and to stimulate the production of short-chain fatty acids (SCFA). These health benefits include:

i) increased resistance to enteric pathogens due to resistance to colonization provided by increased growth of lactic acid bacteria;
ii) increased resistance to infections due to nonspecific stimulation of the immune system;
iii) increased absorption of minerals;
iv) improvement of serum lipid parameters; and
v) increased intestinal mucin production and trophic effects on colonic epithelium, secondary to increased SCFA production.

In another aspect of the invention, practical applications of DCB, and green coffee extracts containing DCB, include:

- Non-digestible dietary supplements, containing DCB, or green coffee extracts containing DCB, targeting symbiotic microorganisms and/or the mucin gel layer within the colon; and foods containing such supplements;
- Food products containing DCB, or green coffee extracts containing DCB, including:
  - Dairy products, e.g., milk, cheese, or yogurt;
  - Baked goods, e.g., breads, cakes, cookies, or granola bars; and
  - Chocolate bars;
- Chewable tablets, buccal tablets, or sublingual tablets containing DCB, or green coffee extracts containing DCB, targeting symbiotic microorganisms in the microbiome within the oral cavity. Such tablets may increase salivary pH values and salivary buffer capacity;
- Candies containing DCB, or green coffee extracts containing DCB, including:
  - hard candies containing a boiled sugar syrup, flavorants, and colorants; and chewable or gummy candies containing sugar, glucose syrup, flavorants, colorants, and a base containing gelatin, pectin, or starch;
- Rectal suppositories containing DCB, or green coffee extracts containing DCB, targeting symbiotic microorganisms and/or the mucin gel layer within the colon;
- Enteric tablets or capsules containing DCB, or green coffee extracts containing DCB, targeting symbiotic microorganisms and/or the mucin gel layer within the colon;
- Toothpastes, gel toothpastes, and mouthwashes (oral rinses) containing DCB, or green coffee extracts containing DCB, to improve the health of the oral microbiome;
- Creams, ointments, or gels containing DCB, or green coffee extracts containing DCB, for topical administration to the skin, to improve the health of the skin microbiome;
- Solid or liquid soaps, shampoos, and conditioners containing DCB, or green coffee extracts containing DCB, for improving the health of the skin or scalp microbiome; and Vaginal ointments or suppositories containing DCB, or green coffee extracts containing DCB, to improve the health of the vaginal microbiome.

Any of the above products may be administered in conjunction with probiotic bacteria for improving microbiome health. For example, oral dosage forms containing DCB may be administered in combination with symbiotic bacteria intended to colonize the gut. The probiotic bacteria may be:

Bacteria from a phylum Bacteroidetes, Firmicutes, or a combination thereof;

Bacteria from a genus *Lactobacillus, Bifidobacterium, Leuconostoc, Pediococcus, Bacteroides, Akkermansia, Streptococcus*, and *Bacillus*, or a combination thereof; and/or Bacteria from a species *Leuconostoc mesenteroides, Lactobacillus plantarum, Pediococcus pentosaceus, Lactobacillus brevis, Leuconostoc citreum, Leuconostoc argentinum, Lactobacillus paraplantarum, Lactobacillus coryniformis, Leuconostoc mesenteroides, Lactobacillus lactis, Lactobacillus fermentum, Lactobacillus acidophilus, Bifidobacterium bifidum, Lactobacillus delbrueckii* subsp. *bulgaricus, Lactobacillus helveticus, Lactobacillus kefiranofaciens*, or a combination thereof.

The probiotic bacteria may be administered in a capsule or in a food product, e.g., milk or yogurt. The probiotic bacteria may be administered in a separate dosage form from DCB, or the probiotic bacteria may be administered in the same dosage form as DCB.

DCB is protected from acids or/and enzymes in the stomach and small intestine. Chlorogenic acids are, generally, resistant to acid environment and digestive enzymes. As seen in FIG. 11, DCB is indigestible at pH values prevailing in the small and large intestine. The DCB complex is dissociated in the colon by borate group transfer to cis-diol sugars, e.g., fructose and sialic acid, in bacteria in the microbiome in the gut mucus membrane. The sugar/borate complexes have a high association constant. However, the DCB complex does not break down in human cells. At a gastric pH of 1.2, DCB undergoes about 50% degradation. See FIG. 11. When there is food in the stomach, after a meal, the stomach pH can raise to as high as 4-5. Under conditions prevailing after a meal (pH 4.5), DCB undergoes <6% degradation. Under conditions prevailing in the intestines (pH 7.2), DCB undergoes <4% degradation. Thus, when administered with a meal, DCB is protected in the gastrointestinal tract and works as a classical prebiotic. Alternatively, DCB may be administered in a dosage form with an enteric coating which is stable and protects DCB from stomach acids, but which dissolves or breaks down at pH values in the intestines. Suitable enteric polymers include methyl (meth)acrylate-(meth)acrylic acid copolymers, cellulose acetate phthalate (CAP), cellulose acetate succinate, hydroxypropyl methyl cellulose phthalate, hydroxypropyl methyl cellulose acetate succinate, polyvinyl acetate phthalate, and similar polymers.

Similarly, rectal or vaginal suppositories containing DCB may be administered in combination with symbiotic bacteria intended to colonize the vaginal surfaces, e.g., a microorganism of the genus *Lactobacillus*. The probiotic bacteria may be administered in the DCB-containing suppository, or in a gel or ointment.

The invention disclosed herein is beneficial in creation of recipes (special mixtures) for the nutrition of microbiota with DCB, or green coffee extracts containing DCB, for improving health of the following "axes": gut-brain axis, gut-immunity axis, intestine-bone axis, intestine-cartilage axis, intestine-heart axis, intestine-lung axis, axial intestinal-thyroid gland axis. Suitable mixtures include the borate ester DCB, in combination with a probiotic microorganism from the genus *Bifidobacterium, Lactobacillus*, and/or *Saccharomyces*; and/or a strain of *Streptococcus salivarius*. Symbiotic nutraceuticals containing DCB promote healthy gut microbiota, and may also offer anti-arthritic effects and anti-inflammatory effects. Symbiotic nutraceuticals containing DCB may help treat symptoms of cancer, heart diseases, and bone diseases.

Regarding the gut-brain axis, psychobiotic products may contain DCB, or green coffee extracts containing DCB, in conjunction with live bacteria that, when ingested in appropriate amounts, may confer a mental health benefit by affecting the microbiome of the host organism. Suitable psychobiotic bacteria may include bacteria of the genus *Lactobacillus*, bacteria of the genus *Bifidobacterium*, and *Streptococcus salivarius*. Such bacteria might play a role in the gut-brain axis, the two-way biochemical signaling that takes place between the gastrointestinal tract (GI tract), including the gut microbiome, and the central nervous system (CNS). Certain species in the gut microbiome may influence the CNS by producing compounds which function as neurotransmitters. Such products may improve the health of the gut microbiome, while also offering nootropic benefits and/or mood-improving benefits to the host organism.

The compositions of the invention can be administered to reduce blood pressure in mildly hypertensive people. Reducing the blood pressure of hypertensive patients is effective in preventing, treating, and/or reducing recovery times for ischemic stroke (IS). For every 10 mmHg decrease in systolic blood pressure and/or 5 mmHg decrease in diastolic blood pressure, the risk of IS can be reduced by up to 41%. Hypertension is a high-risk factor for IS. Hypertension induced by gut microbiota dysbiosis through inflammation, immune and anabolism directly increases the risk of IS, and impairs recovery after IS.

IS represents the disease with the greatest morbidity and mortality in the entire world. Several GI diseases are associated with increased risk of IS after adjusting for known risk factors for IS. The most significant positive correlations included gastric diseases, functional GI diseases, and inflammatory GI diseases. Also, the gut microbiota may contribute to the progression of IS. By regulating the intestinal microbiota, inflammation, atherosclerosis, and thrombosis are attenuated to prevent IS. Also, by intervening and regulating the gut microbiota, it alleviates obesity, diabetes, and hypertension to reduce the risk of developing IS. Even after an IS, the gut microbiota can be adjusted to promote recovery and improve prognosis. Rebuilding the intestinal microbiota after an IS can also stop the progression of the disease and improve the prognosis. The use of prebiotic natural DCB-rich GCBE supplements, or the compound DCB to restore the balance of the gut microbiota may assist in the management of IS in the future. In addition, these prebiotics can be considered as a substitute for probiotics or as an additional support for probiotics. Gut microbiota has become a potential diagnostic and nutritional adjuvant target for IS, Alzheimer's disease, Parkinson's Disease, depression, and many other diseases.

The accumulation of boron in the intestinal mucus gel layer after the ingestion of DCB may have beneficial health effects. Exogenous supplementation with a DCB-rich natural extract or DCB alone may increase AI-2B concentrations, reduce intestinal damage, and corrected microbial flora changes in diarrhea. Thus, many factors lead to microbiota dysbiosis and significantly decrease the concentration of AI-2B, which leads to reduced ability of the QS system to maintain the stability of the intestinal microbiome, potentially leading to the occurrence of diarrhea. In addition, the addition of DCB, or a green coffee bean extract containing DCB, can increase boron levels in the intestine, which is conducive to the regulation of intestinal homeostasis by the QS system and reduces the inflammatory response and microbiota dysbiosis.

Mouthwashes containing DCB, or a green coffee bean extract containing DCB, may have an effect on the oral microbiota balance by reducing the formation of dental plaque, which is an accumulation of different species of bacteria. In addition, administration of a DCB-rich natural extract-containing mouthwash may also reduce the development of plaque, and concomitant mineralization and formation of calculus. Thus, the action of a mouthwash with a DCB-rich natural extract may improve the balance of oral microbiota, and their influence on the oral systemic health. In the future, an analysis of AI-2B in saliva may be an important biomarker regarding the prognosis of a healthy oral microbiome.

Manipulation of the QS AI-2 signal affects the antibiotic-treated gut microbiota. These findings provide new mechanistic insights into how AI-2 functions as a signal for intraspecies and interspecies communication because increased AI-2 amount counteracts antibiotic-induced dysbiosis. DCB or a DCB-rich natural extract may serve as a nutritional adjuvant for the gut microbiota in patients undergoing long-term antibiotic therapy for respiratory tract infection, including tuberculosis. The essentiality of boron for a healthy relationship between the microbiota and the human host make DCB and/or DCB-rich natural extracts into a promising prebiotic candidates in human and animal nutrition. The microbiota influences the health of the body through the intestine-brain axis, intestine-immunity axis, intestine-bone axis, intestine-cartilage axis, intestine-heart axis, intestine-lung axis, intestine-thyroid axis. This may explain the beneficial role of B in preventing certain diseases, such as: osteoarthritis, osteoporosis, rheumatoid arthritis, cardiovascular inflammation, depression, obesity, diabetes, viral and bacterial infections, and thyroid diseases. The mechanism of action of organic borates is related to the AI-2B signaling molecule, as well as to the fortification of the colonic mucus with boron from prebiotic diet.

Various embodiments disclosed herein relate to a borate ester of chlorogenic acid, wherein the borate ester has a structure of formula (I) or a structure of formula (II), wherein the boron atom in the borate ester is enriched in $^{10}B$.

Various embodiments disclosed herein relate to a method of treating intestinal cancer in a subject in need thereof by boron neutron capture therapy, by administering a $^{10}B$-enriched borate ester of formula (I) or (II) to the subject and allowing the borate ester to enter a mucus gel layer of an intestine of the patient; irradiating the intestine with neutrons, thereby converting the $^{10}B$ to excited $^{11}B$; and allowing the excited $^{11}B$ to decay, producing high-energy alpha particles ($^4He$ nuclei) and high-energy lithium-7 ($^7Li$) nuclei in the intestine. The $^{10}B$-enriched borate may be produced by reacting $^{10}B$-enriched boric acid with chlorogenic acid, using synthetic methods disclosed herein.

The current disclosure is based on the discovery that:

i) Boron is essential for the symbiosis between the beneficial microorganisms in the microbiome and the human or animal host; and ii) Borate esters are not required for the human cell.

The cells of the human or animal host do not need boron. Boron is only required for healthy symbiosis between the microbiome and the human/animal host. In other words, boron is essential for the healthy symbiosis between the host organism and the various microbiomes of the gut, scalp, mouth, skin, and vagina. The borate ester DCB is indigestible by the host organism, but is accessible to the microbiome.

EXAMPLES

Method of Present Invention for Preparing DCB

The optimum method for obtaining a green coffee extract containing a borate ester of chlorogenic acid involves extraction using specific polar solvents, which may be acetonitrile, water, or mixtures thereof. In some embodiments, use of specific solvents having a polarity higher than that of water or alcohol may be used in combination with extraction using aqueous alcohol to result in an enriched extract of green coffee beans containing upwards of 70% chlorogenic acids.

The optimum method for synthesis of a borate ester of chlorogenic acid involves reaction of boric acid and chlorogenic acid in a solvent, which may be acetonitrile, water, or mixtures thereof. In some embodiments, boric acid and chlorogenic acid are reacted in aqueous acetonitrile or in superheated water.

Ultra-High-Performance Liquid Chromatography (UHPLC) Analytical Conditions

Reference solution preparation. 1 mg of each reference compound [caffeine (Sigma-Aldrich, Germany), CA (Alfa Aesar, Thermo Fisher GmbH, Kandel, Germany) and DCB obtained according to Example 2 below] is added to a 10 mL volumetric flask. 10 mL of acetonitrile-water mixture (1:1, v/v) is added, and sonication is carried out for 20 minutes. The final volume is made up with the same acetonitrile-water mixture. The solution is shaken well and filtered through a 0.2 m syringe filter.

Sample solution preparation. 10 mg of test compound sample, e.g., DCB or green coffee bean extract, is taken in a 50 mL volumetric flask. 40 ml of acetonitrile-water mixture (1:1, v/v) is added, and sonication is carried out for 20 minutes. The final volume is made up with the same acetonitrile-water mixture. The solution is shaken well and filtered through 0.2 m syringe filter.

Chromatographic assessment of purity. The solvent flow rate, analytical column type, flow rate conditions, etc. are described in Tables 1, 1A, 2A, 2B, 3, and 4. Tables 1A and 2A correspond to the UHPLC conditions of Protocol A, which was used in all cases unless otherwise specified. Tables 1B and 2B correspond to the UHPLC conditions of Protocol B.

TABLE 1A

UHPLC conditions; Protocol A.

| | |
|---|---|
| UHPLC system | ACQUITY Arc System |
| Column | Waters CORTECS ® C18, 4.6 × 50 mm, 2.7 μm |
| Column temperature | 25° C. |
| Injection volume | 5 μL |
| Flow rate | 0.5 mL/min |
| Mobile phase A | 10 mM Ammonium formate |
| Mobile phase B | Acetonitrile |
| Runtime | 21 minutes |

TABLE 1B

| UHPLC conditions; Protocol B. | |
|---|---|
| UHPLC system | ACQUITY Arc System |
| Column | Waters CORTECS ® C18, 4.6 x 50 mm, 2.7 μm |
| Column temperature | 25° C. |
| Injection volume | 5 μL |
| Flow rate | 0.5 mL/min |
| Mobile phase A | 0.1% formic acid in water |
| Mobile phase B | 0.1% formic acid in acetonitrile |
| Runtime | 21 minutes |

TABLE 2A

Elution gradient for UHPLC analysis; Protocol A.

| No. | Time [min] | Flow rate [mL/min] | % A | % B |
|---|---|---|---|---|
| 1. | Initial | 0.5 | 92 | 8 |
| 2. | 8 | 0.5 | 80 | 20 |
| 3. | 16 | 0.5 | 73 | 27 |
| 4. | 19 | 0.5 | 40 | 60 |
| 5. | 20 | 0.5 | 40 | 60 |
| 6. | 21 | 0.5 | 92 | 8 |

TABLE 2B

Elution gradient for UHPLC analysis; Protocol B.

| No. | Time [min] | Flow rate [mL/min] | % A | % B |
|---|---|---|---|---|
| 1. | Initial | 0.5 | 90 | 10 |
| 2. | 5 | 0.5 | 70 | 30 |
| 3. | 10 | 0.5 | 50 | 50 |
| 4. | 11 | 0.5 | 90 | 10 |

TABLE 3

| Mass Spectroscopy Conditions. | |
|---|---|
| MS detector | ACQUITY QDa (Performance) |
| Ionization mode | $ESI^-$, $ESI^+$ |
| Capillary voltage | 0.8 kV |
| Sample temperature | 400° C. |
| Cone voltage | 20 V |
| Sampling rate | 8 points/second |
| SIR channels | See Table 4 |

TABLE 4

Selective ion recording (SIR) channels' m/z values, the electrospray ionization (ESI) polarity, and the retention time (RT) for the analyzed compounds.

| Analyte | SIR channels' m/z values and ESI polarity | Retention time [min]; Protocol A | Retention time [min]; Protocol B |
|---|---|---|---|
| Caffeine | 195 (+) | 3.85 | — |
| CA | 353 (−) | 3.30 | 2.48 |
| DCB | 715 (−) | 7.88 | 5.75 |

Example 1

Semi-Synthesis and Purification of Food-Grade DCB

Figure 1A:
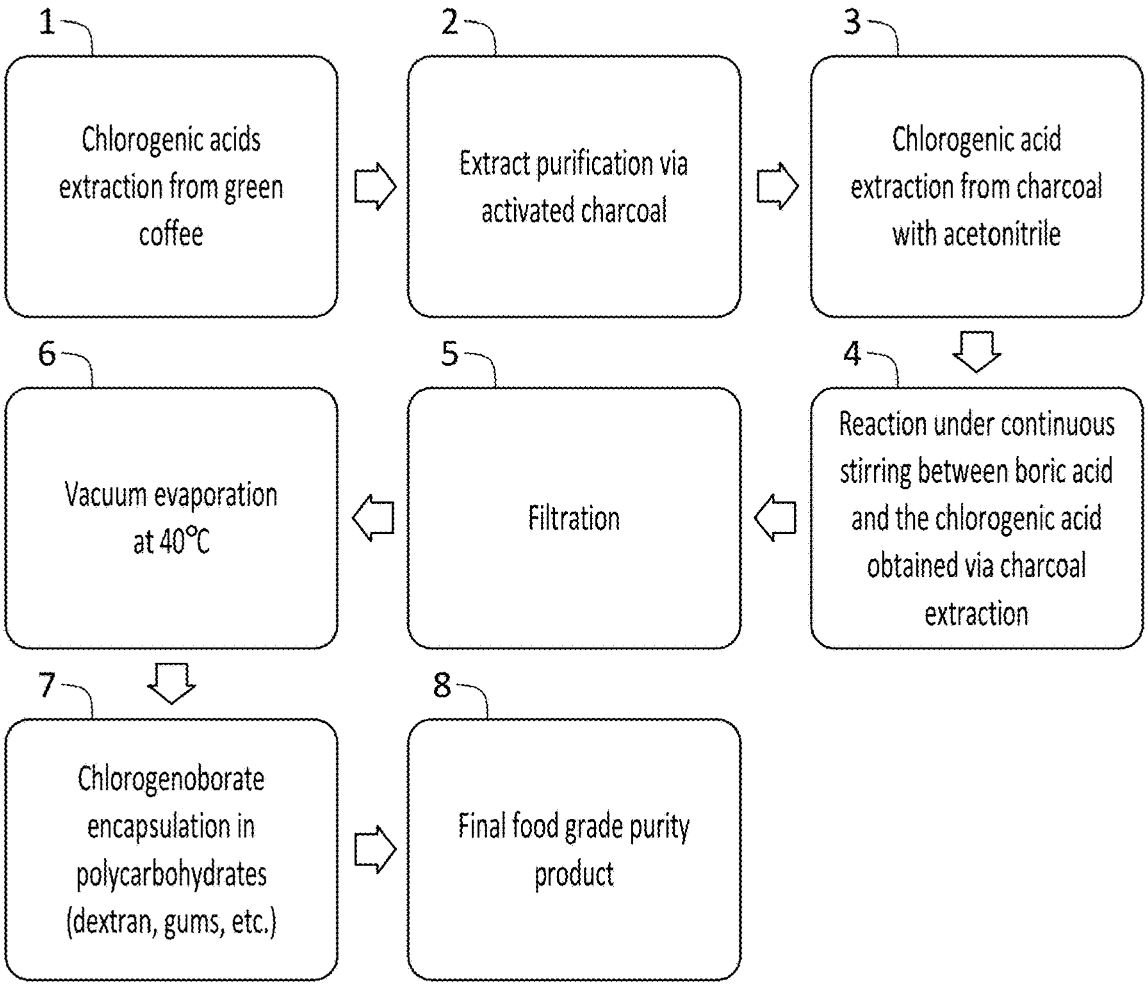
FIG. 1A is a food-grade and pharmaceutical-grade DCB manufacture flow chart (DCB: Chlorogenoborate diester complex)

An illustrative embodiment of the production method and purification can be exemplified by the following non-limiting sequence of steps for the food preparation-grade DCB comprising the steps of:

a) Extracting chlorogenic acids from green coffee beans with aqueous acetonitrile (FIG. 1, step 1);

b) Purifying the aqueous acetonitrile extract by filtration through activated charcoal (FIG. 1, step 2);

c) Extracting adsorbed chlorogenic acids from the activated charcoal by washing with acetonitrile (FIG. 1, step 3);

d) Dissolving an appropriate amount of chlorogenic acid and boric acid (mass ratio 1:1) in an acetonitrile-water solvent (1:1 by volume), and stirring the mixture to form a homogeneous solution in an ultrasound bath (FIG. 1, step 4);

e) filtering the homogeneous solution (FIG. 1, step 5); and f) recovering DCB from the filtrate.

HPLC preparative or flash chromatography may be used for purification of DCB to obtain a pharmaceutical-grade DCB complex.

Synthesis optimization: Multiple synthetic protocols were tested, varying different parameters of the reaction. The carried tests are presented in the FIG. 10. The coupling reaction between chlorogenic acid and boric acid was discovered to be efficient at temperatures of 60-65° C. This comprises the presently preferred embodiment of the invention. The synthetic profiles differed in the method of isolating DCB from the filtered homogeneous solution, as follows:

(1) Rotary evaporated (solvent acetonitrile-water 1:1, v/v);

(2) Oven evaporated (solvent acetonitrile-water 1:1, v/v);

(3) Freeze dried (solvent water);

(4) Freeze dried with calcium (solvent water);

(5) Air evaporated (solvent water)

As can be seen in FIG. 10, rotary evaporation of the acetonitrile/water solvent mixture (1) or oven evaporation of the acetonitrile/water solvent mixture (2) produced 0.5 to 1.1% DCB product. Evaporating acetonitrile from the filtered homogeneous solution to produce a water solution, and then freeze drying the water solution (3), or evaporating water from the water solution in air (5), produced 32 to 41% DCB product. However, freeze drying the water solution in the presence of calcium (4) produced 0.2% DCB product. Thus, the preferred protocol for recovering DCB in good yield from the filtered acetonitrile/water solution involves:

evaporating the acetonitrile solvent from the filtrate under vacuum at 40° C. (FIG. 1, step 6); and lyophilizing (freeze-drying) the water solution of DCB to obtain a food-grade DCB.

The food-grade DCB may be combined with a carrier, e.g., a carbohydrate polymer, a carbohydrate gum, a mono- or disaccharide, a sugar alcohol, a gelatin, etc. (FIG. 1, step 7) to produce a final food- or pharmaceutical-grade product (FIG. 1, step 8).

Example 2

Synthesis of DCB with Superheated Water

A process for preparing a borate ester of chlorogenic acid involves reacting a solution comprising chlorogenic acid and boric acid in a mass ratio of 1:1 in a superheated water solvent, i.e., liquid water under pressure at temperatures between the usual boiling point, 100° C. (212° F.) and the critical temperature, 374° C. (705° F.) comprising a mixture of water and acetonitrile. The reaction is carried out in an autoclave reactor o form a reaction mixture.

In an exemplary method, green coffee beans were frozen with liquid nitrogen to produce freeze-died green coffee bean powder while minimizing CA degradation. A mixture of the freeze-died green coffee bean powder (100 g), boric acid (at least 10 g) and distilled water (300 mL) was magnetically stirred for 30 minutes at 150° C. (4.8 atmospheres) in an autoclave. After cooling, the solution was vacuum filtered. The filtrate was freeze-died to obtain GCBE dry powder, which was then ground with a grinder.

Example 3

Identification and Quantification of DCB in Green Coffee Beans (GCB) Using Acetonitrile.

The borate diester of chlorogenic acid was identified and quantified in green coffee beans. A green coffee bean (GCB) extract was prepared by macerating 1 g of powdered GCB, overnight, with 50% acetonitrile. The solvent was evaporated, and the extract was dissolved in 1 mL 50% acetonitrile, and filtered through 0.2 m syringe filters. Then 5 μL of the filtrate were injected into a UHPLC chromatographic column (Protocol B). The chlorogenoborate peak was identified in SIR mode with a retention time of 5.75 minutes in a concentration of 2.48 μg/g of dry product.

A UHPLC/MS analysis was performed on the Waters Arc System coupled with a Waters 2998 photodiode array (PDA) and a quantitative data analysis (QDa) was performed with an electrospray ionization (ESI) probe. The column was a Waters Cortecs C18 column (4.6×50 mm, 2.7 m), eluting with solvent A (0.1% formic acid in water) and solvent B (0.1% formic acid in acetonitrile), using Protocol B. The flow rate of the mobile phase was set at 0.6 mL/min. The column temperature was equilibrated to 20° C. The injection volume was 5 μL. The detectors were set as follows:

The PDA was set to only detect the 325 nm wavelength and the QDa was set to negative mode at 0.8 kV for the capillary, 50 V for the cone voltage and 400° C. for the capillary.

The MS range was set between m/z 100-800. A relatively high amount of CA remains after the reaction and can be identified by the large peak at 2.50 minutes.

The compound DCB has a retention time of ~5.75 minutes, as shown in Table 5. Table 5 shows the retention times and relative areas of the compounds (CA, DCB). CA has a specific fragmentation pattern with m/z 191 $[M-H]^-$ for quinic acid, m/z 353 $[M-H]^-$ for CA and m/z 707 (CA dimer; $[2M-H]^-$). The compound DCB exhibits the specific pattern for a boron-containing compound: 80% m/z 715 $[M-H]^-$ for $^{11}B$ and 20% m/z 714 $[M-H]^-$ for $^{10}B$. For quantification purposes, the SIR for m/z 715 was used, as shown in Table 6. Table 2 shows fragment ions (m/z) found in the mass spectra and the assigned molecular structures. The limit of detection (LOD) and limit of quantification (LOQ) were 0.396 μg/mL and 1.202 μg/mL, respectively.

TABLE 5

| Compound | Retention time [min] | Relative area |
|---|---|---|
| Chlorogenic acid | 2.478 | 20 921 574 |
| DCB $^{10}B$ | 5.742 | 173 776 |
| DCB $^{11}B$ | 5.742 | 818 884 |

TABLE 6

| Compound | Fragment ions (m/z) | Assigned molecular structure |
|---|---|---|
| Chlorogenic acid | 191 | Quinic acid |
| | 353 | Chlorogenic acid |
| | 707 | Chlorogenic acid dimer |
| DCB | 191 | Quinic acid |
| | 715 | Newly formed DCB |

To obtain a DCB standard, CA (Alfa Aesar, Thermo Fisher GmbH, Kandel, Germany) and boric acid (Merck, Burlington, Massachusetts, USA) were used. A mixture of CA and boric acid in water solution were mixed at 65° C. for three hours. After cooling, the solution was frozen and freeze-dried for 24 hours. Then, the solid mass obtained was separated by preparative thin-layer chromatography (TLC) by utilizing a thick layer of adsorbent (5 mm). Approximately 250 mg DCB was obtained in a purity of 95% DCB, and used to create a calibration curve. The freeze-dried powder was dissolved in water to obtain DCB concentrations of 2 μg/mL, 4 μg/mL, and 8 μg/mL.

Figure 3A:
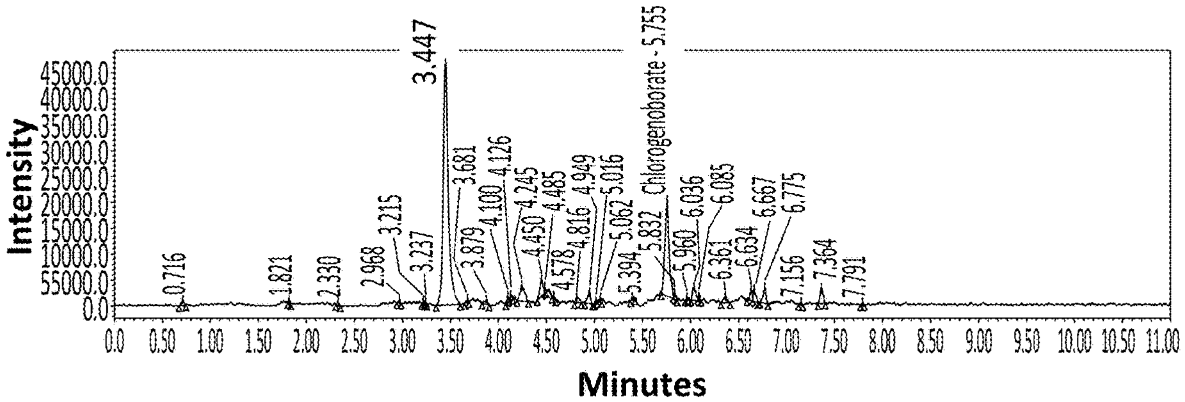
FIGS. 3A to 3I show.
Figure 3B:
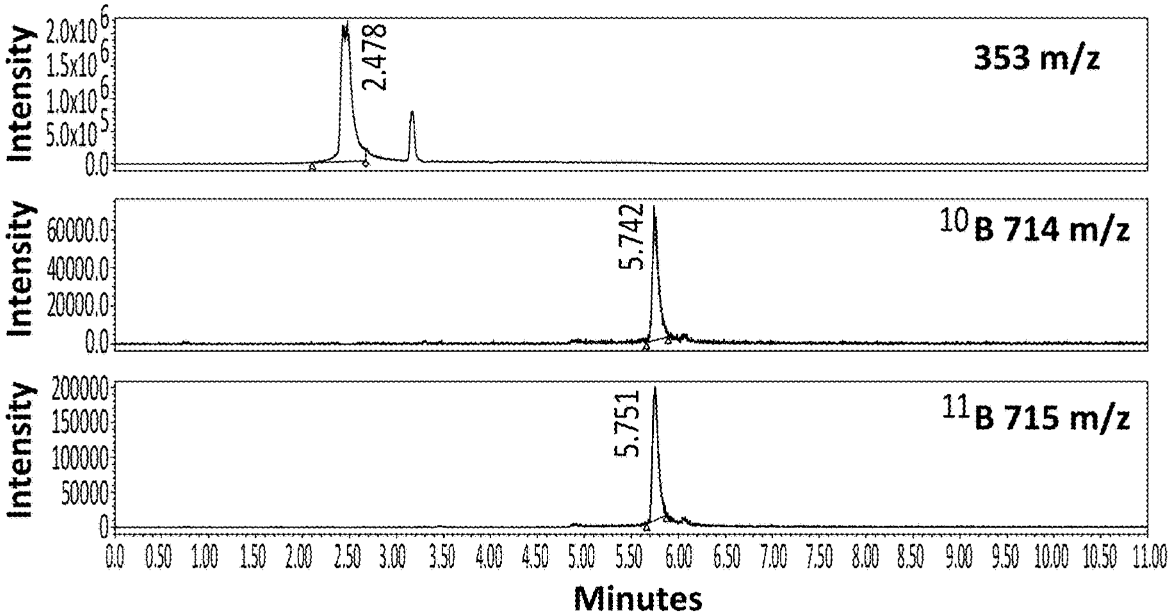

The DCB was also identified in GCB via high-performance thin-layer chromatography (HPTLC)/UV-densitometry (FIGS. 2A to 2D) and UHPLC/MS (FIGS. 3A and 3B). Extraction was achieved using 90% acetonitrile, which was then evaporated and solubilized in the first line of the gradient. The 1:5 boron isotope ratio was observed.

Figure 3C:
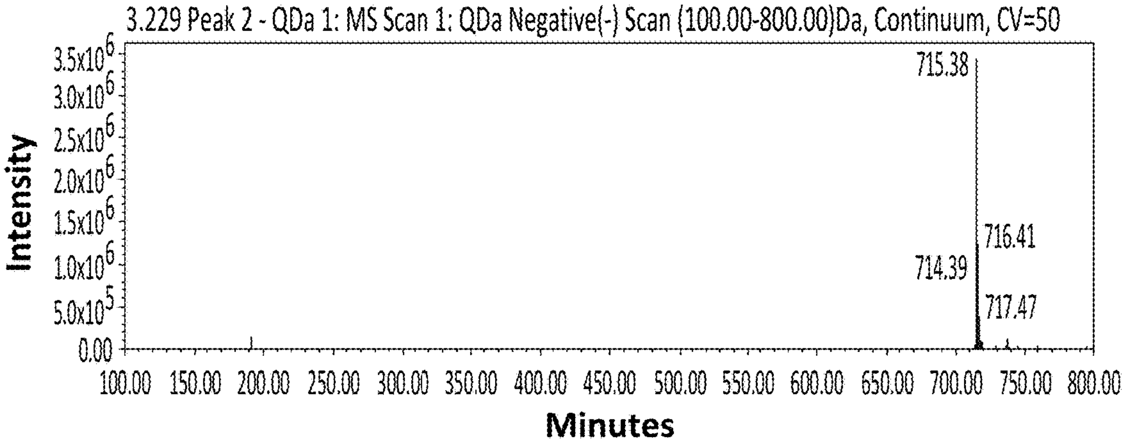
Figure 3D:
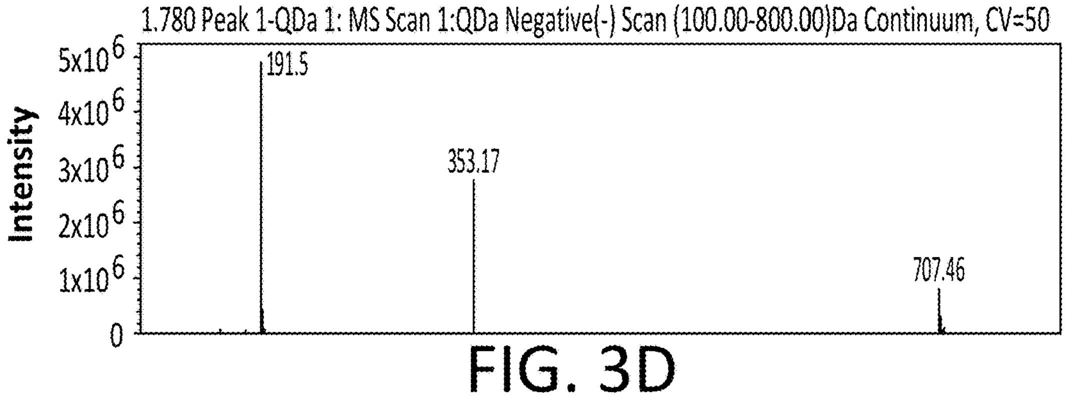
Figure 3E:
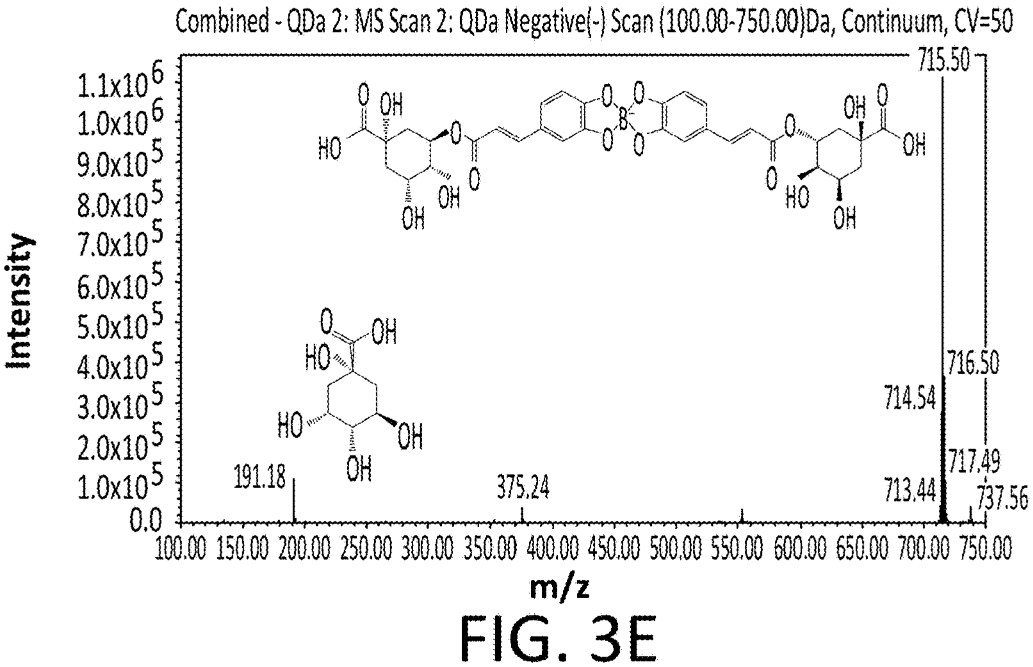
Figure 4A:
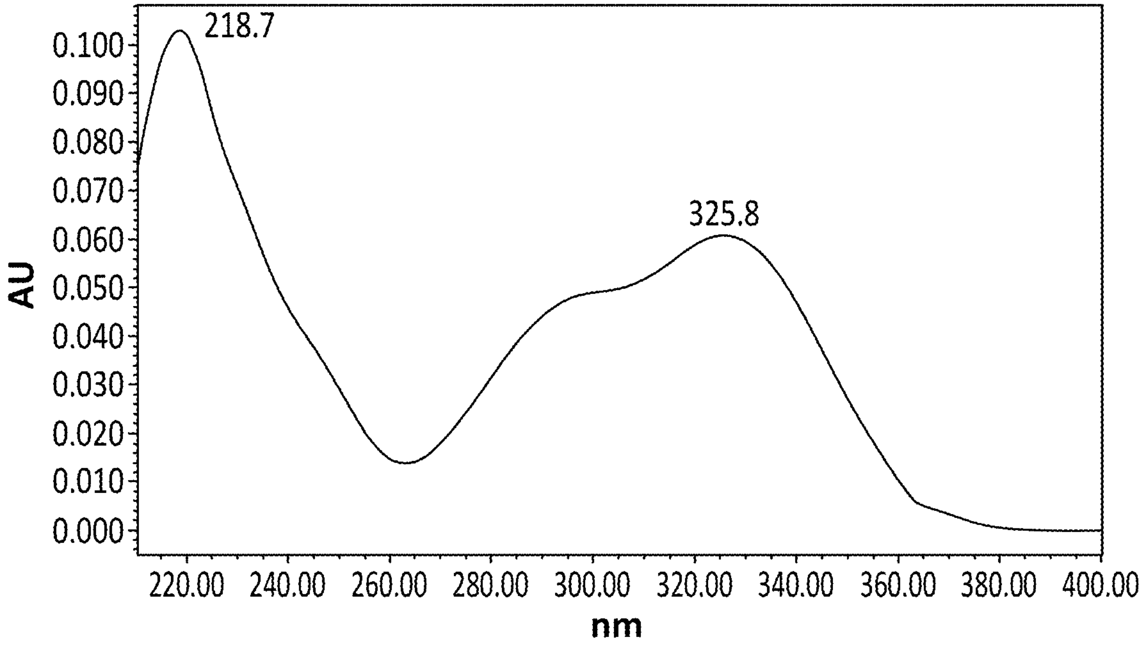
FIGS. 4A and 4B show.
Figure 5:
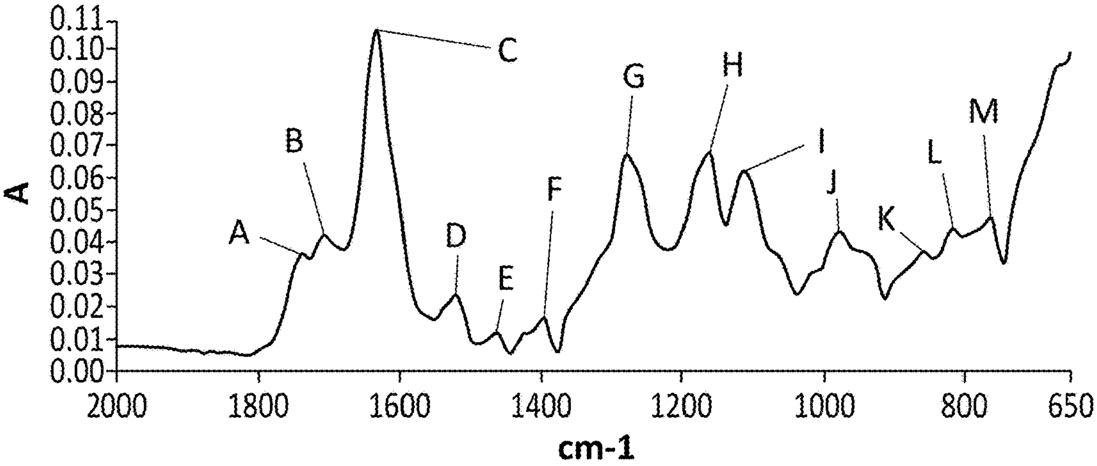
FIG. 5 is FTIR spectrum of DCB, where the following peaks are assigned.

The structure of the DCB standard was proven by UV spectroscopy (FIG. 4A), UHPLC/MS analysis (FIGS. 3C and 3E, with fragment ion m/z 715), FTIR spectra (FIG. 5), and the proposed structural formula (FIGS. 6C and/or 6D) was confirmed by $^1H$-NMR spectroscopy (FIG. 7A). The resulting DCB is readily separated from unreacted CA by chromatography, ion exchange chromatography, or solvent extraction, as is well known in the art.

Figure 3F:
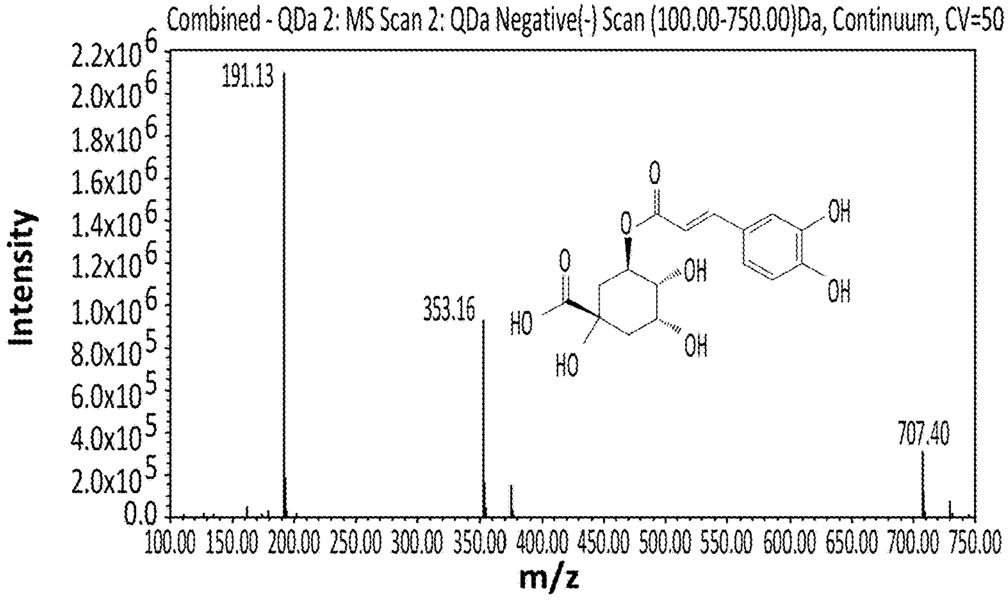
Figure 3G:
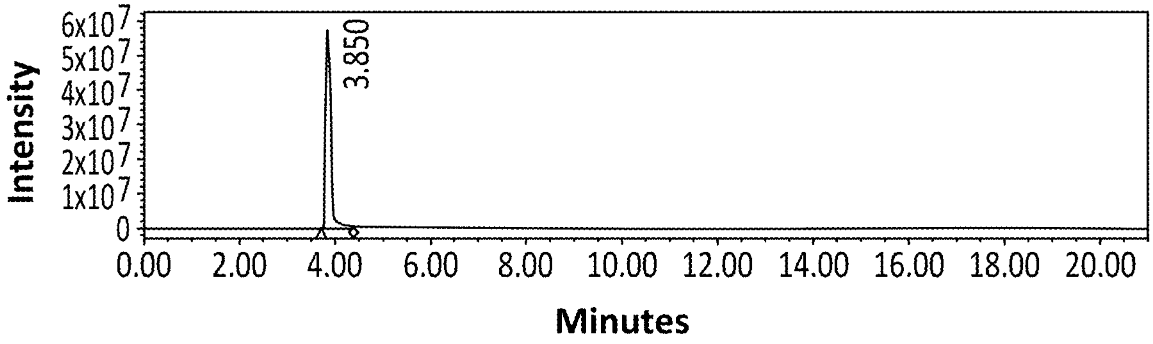
Figure 4B:
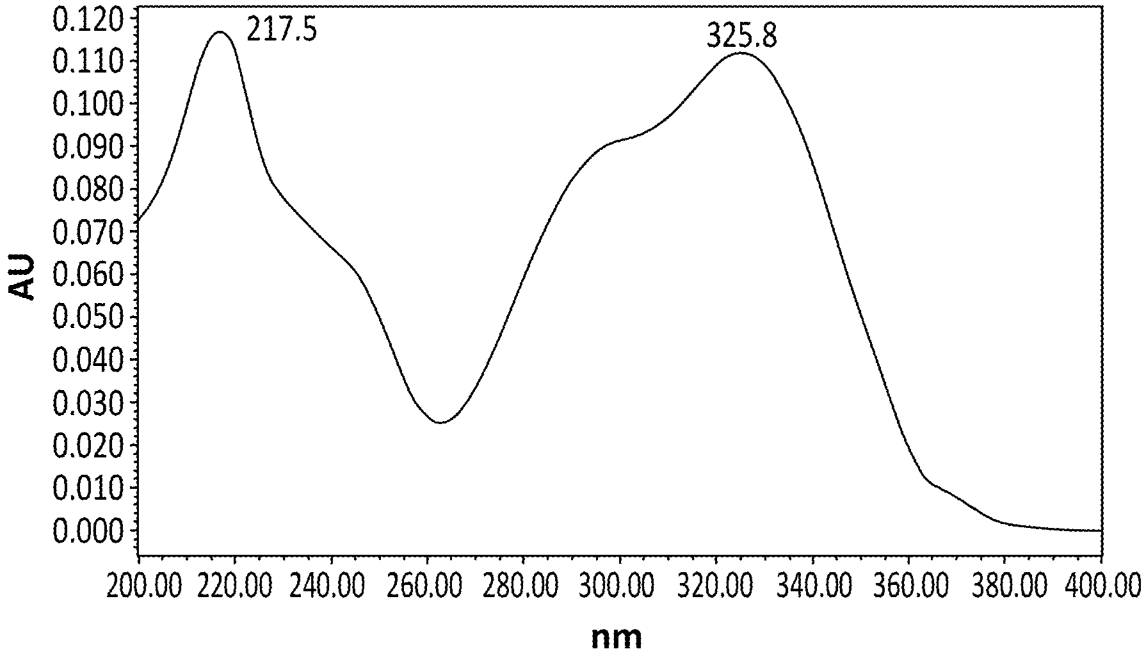

The structure of the chlorogenic acid compound was proven by UV spectroscopy (FIG. 4B), and UHPLC/MS analysis (FIGS. 3D and 3F, with fragment ion m/z 353), FTIR spectra (FIG. 5), and the proposed structural formula (FIGS. 6A-6D) was confirmed by $^1H$-NMR spectroscopy (FIG. 7B).

FIGS. 2A to 2D highlighted the HPTLC/UV-densitometry analysis of BA, CA, DCB, GCB extract and of GCB extract with BA, using Protocol B. The DCB peak was identified in SIR mode at 5.75 minutes in a concentration of 2.48 μg/g of dry product (Table 1; FIG. 8). CA has the specific fragmentation pattern with m/z 191 $[M-H]^-$ for quinic acid, m/z 353 $[M-H]^-$ for CA and m/z 707 $[2M-H]^-$ (CA dimer). The newly formed compound exhibits the specific pattern for a B-containing compound: 80% m/z 715 $[M-H]^-$ for $^{11}B$ and 20% m/z 714 $[M-H]^-$ for $^{10}B$. For quantification purposes, the SIR for m/z 715 was used (Table 2). DCB emerges in stable form by direct reaction of chlorogenic acid and boric acid. A mixture of chlorogenic acid and boric acid in acetonitrile or water solution is mixed at 65° C. for one to eight, two to five, or about three hours. The mixture is analyzed by reverse phase UHPLC/UV. DCB (RT 3.6 minutes) was recovered in this procedure (40% yield) together with unreacted chlorogenic acid (RT 7.4 minutes) (FIG. 9).

From the above table and examples, the modified process of the present invention results in a green coffee bean extract in which the content of the bioactive compounds, i.e., total chlorogenic acids, is higher at about 70-80% than extracts known from the prior art. The extract of the present invention accordingly has a considerably improved therapeutic profile owing to a higher concentration of the bioactive compounds (Chlorogenic acids and other polyphenol compounds), and also higher purity. In contrast, a commercially available sample of green coffee bean extract when analyzed not only shows a lower content of chlorogenic acids, but also several other additional peaks (FIGS. 2C and 2D), thus indicating the presence of other compounds which are absent in the extract of present invention.

Example 4

Extraction with Ethyl Acetate

Ethyl acetate is used to carry out extraction of the chlorogenic acids and DCB. Thereafter, the extract is purified by using solvents to remove fats and caffeine. The process thus uses only three solvents in the entire process. These solvents are water, ethyl acetate, and a chlorinated solvent, e.g., chloroform or methylene chloride, for removal of caffeine.

Extraction: Powdered coffee beans (1 Kg or 1000 grams) are charged in a 5.0-liter flask fitted with a stirrer. 2 liter acidic water is added at 40-50° C. and gradually heated to 55°-70° C. with constant stirring for 4 hours. Thereafter, 4 liter of ethyl acetate is added and stirring is carried out at a slightly elevated temperature of 50-55° C. The reaction mixture is filtered, and the solid powder is transferred back to the flask. Steps of extraction with water and ethyl acetate are repeated 2-3 times, till the herb is completely exhausted. The organic solvent layer is separated from the water layer, and concentrated to dryness.

Purification: The dry material (dry extract) obtained is dissolved in 500 ml water. The water solution is then washed with 250 ml chlorinated solvent (Chloroform, Methylene chloride etc.) two times, to remove caffeine, which can be harmful if concentrated to excess amounts. Hence, its removal is necessary. The water is then evaporated to obtain the green coffee bean extract as a dry powder. No defatting step or use of solvent to remove fats is needed.

Figure 3H:
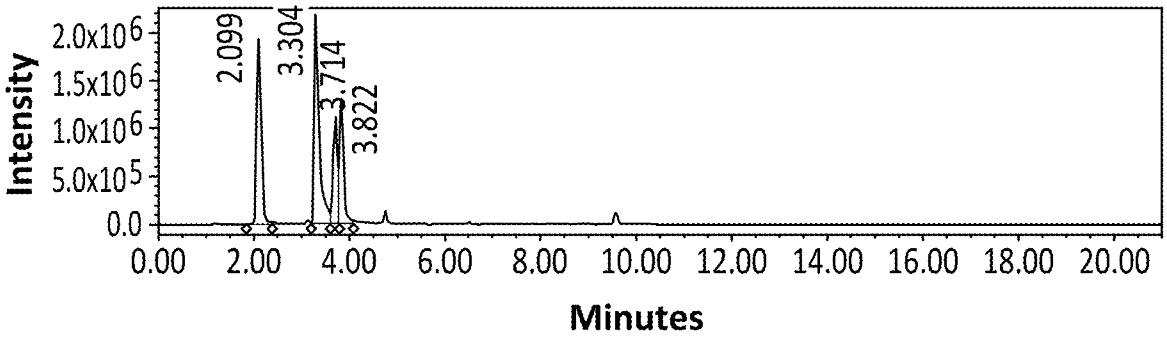
Figure 3I:
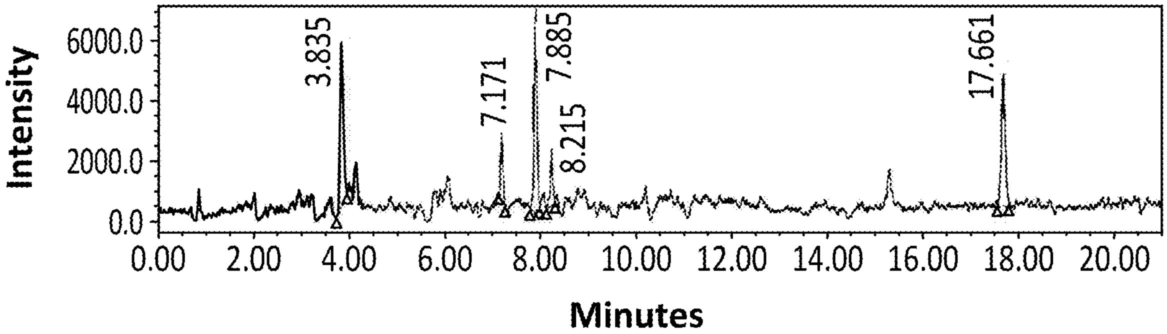

Yield and Chlorogenic acid and DCB content: 110-120 g of extract, i.e., 11-12% in form of pale yellow fine powder. Content of Chlorogenic acids by HPLC is in the range of 70-80%. Analytical profile of the extract showed presence of peaks for Chlorogenic acids & DCB, using UHPLC/MS under Protocol A (CA Retention time RT is 3.30; m/z=353; DCB RT is 7.89; m/z=715; See FIGS. 3H and 3I).

Example 5

Extraction Using Water-Acetonitrile Mixture

In this method, acetonitrile is used to carry out extraction of the CAs and DCB from green coffee beans (GCB). The process uses only acetonitrile and water in the entire process.

Extraction. Powdered decaffeinated GCB (1000 g) and 1 L water are charged in a flask fitted with a stirrer, and the temperature is increased to 55-70° C., with constant stirring for four hours. Thereafter, 4 L of acetonitrile are added, and GCB is stirred in 80% aqueous acetonitrile at a temperature of 50-55° C. The reaction mixture is filtered, and the GCB powder is transferred back to the flask. Extraction with 80% aqueous acetonitrile is repeated 2-3 times, till the GCB is completely exhausted. The liquid layer is separated from the GCB residue, and the acetonitrile is evaporated to produce a water solution of GCB extract.

Purification. The water solution of GCB extract is freeze-dried to obtain a GCBE dry powder extract. No defatting step or use of solvent to remove fats is needed. Yield of DCB-rich extract content: 90-100 g/1000 g of decaffeinated GCBE in the form of pale-yellow fine powder. Content of CAs by HPLC is in the range of 30% and average 6% DCB. Analytical profile of the extract using HPLC conditions of Tables 1A and 2A showed the presence of peaks for Chlorogenic acids and DCB, where CA (Retention time RT is RT 3.30; m/z=353; See FIG. 3H) and DCB (RT is 7.89; m/z=715; See FIG. 3I).

Example 6

Extraction with the Use of Superheated Water

Another method of extracting CA and DCB is the use of liquid water under pressure at temperatures between the usual boiling point, 100° C. (212° F.) and the critical temperature, 374° C. (705° F.). It is also known as "subcritical water" or "pressurized hot water".

Figure 1B:
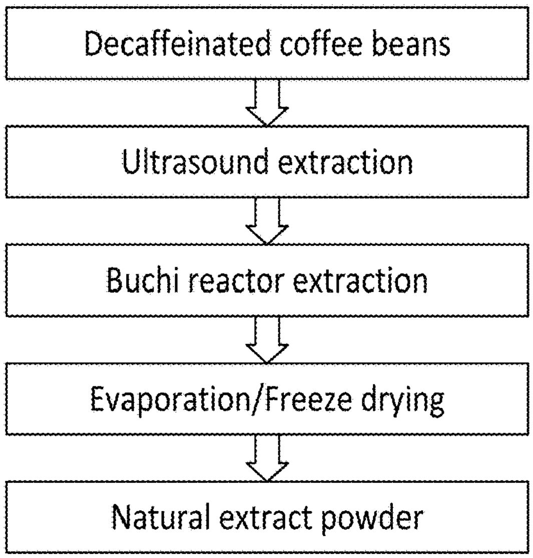
FIG. 1B is a flow chart for manufacture of a DCB-containing green coffee bean extract.
Figure 2A:
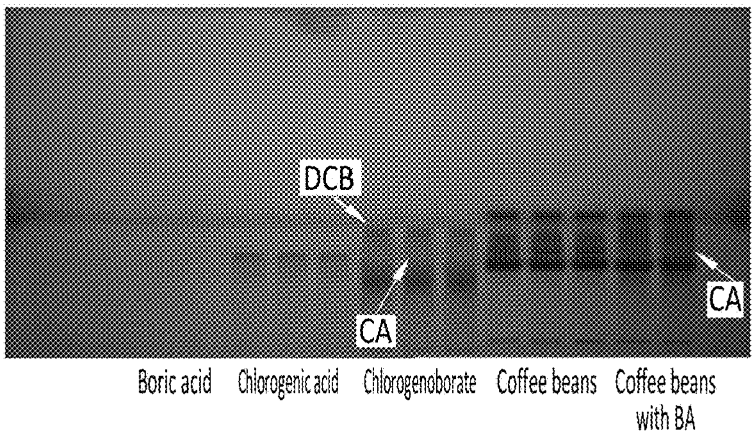
FIGS. 2A to 2D show HPTLC/UV-densitometry analysis.
Figure 2B:
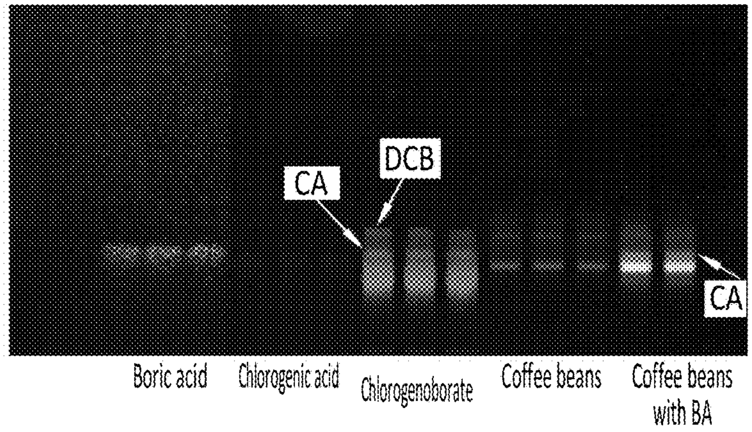
Figure 2C:
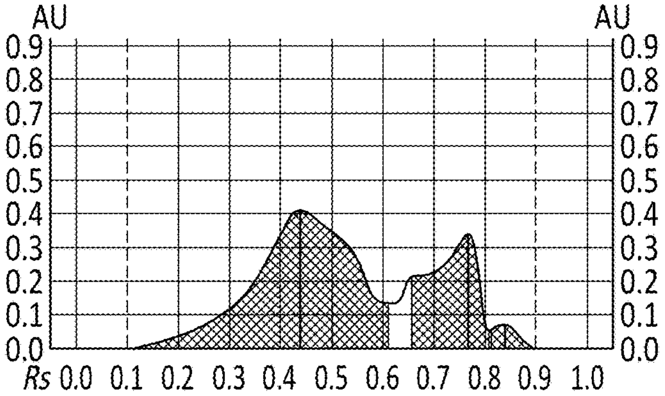
Figure 2D:
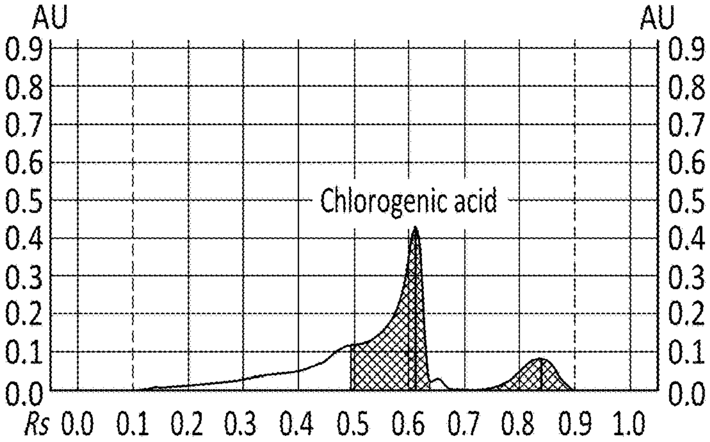

Extraction. A mixture of freeze-died, optionally decaffeinated, green coffee bean powder (100 g; FIG. 1B, step 1) and distilled water (300 mL) was magnetically stirred for 30 minutes at 150° C. (4.8 atmospheres) in an autoclave or Buchi reactor (FIG. 1B, step 3). Prior to use of superheated water, extraction with water may be carried out with ultrasound (FIG. 1B, step 2). After cooling, the solution was vacuum filtered. GCBs were previously frozen by liquid nitrogen to minimize CA degradation, freeze-died, and ground with a grinder.

Purification. The separated water is freeze-dried or evaporated to obtain the GCBE dry powder of the present invention (FIG. 1B, step 4) to produce a natural extract powder containing DCB (FIG. 1B, step 5).

Boron fortification. Boric acid may be added to the reaction mixture at 150° C. temperature (4.8 atmospheres) for 30 minutes. After that, separation by filtration and freeze-drying will be performed in order to obtain boron-enriched food-grade semisynthetic DCB (up to 30% DCB).

Example 7

DPPH Scavenging Assay for Chlorogenic Acid and DCB

The antioxidant activity of Chlorogenic Acid was assessed based on radical scavenging of the stable 2,2-diphenyl-1-picrylhydrazyl (DPPH) free radical. CA showed strong free radical scavenging activity against DPPH radicals, with a half maximal inhibitory concentration ($IC_{50}$) value of 15.24 μg/mL (0.044 μM/mL) (FIG. 12B). This antioxidant activity increased dramatically at 10 μg/mL (100% inhibition of DPPH).

The $IC_{50}$ values of DCB and CA are first separately determined using the DPPH assay. FIG. 12A shows the antioxidant activity of DCB, while FIG. 12B shows the antioxidant activity of CA. The $IC_{50}$ value of CA was determined by the DPPH assay and was 15.24 μg/mL, while for DCB, the $IC_{50}$ value was 2.55 μg/mL (0.007 μM/mL). This roughly sixfold increase in antioxidant activity, resulting in a decrease in $IC_{50}$, seems to be due to the formation of an adduct with the DPPH superoxide radical by the trigonal form of DCB (radical adduct formation (RAF) mechanism; see FIG. 12C) and an increase in the proton transfer rate (hydrogen atom transfer (HAT) mechanism) from the carboxylic acid groups in the quinic acid ester moiety.

Additionally, the borate ester of CA, DCB, is metabolized only after loss of the borate group. DCB itself is not metabolized in the colon. After microbiota and the mucus gel layer are saturated with boron, then DCB remains intact in the colon, where it acts as an antioxidant. As seen in the present example, the indigestible borate ester DCB offers approximately six times more antioxidant activity than CA.

Example 8

Effect of DCB on in vitro acetylcholinesterase activity assay

In vitro, DCB was found to inhibit acetylcholinesterase (AChE) activity ($IC_{50}$ 28.25 μg/mL) and free radical scavenging activity ($IC_{50}$ 2.55 μg/mL) in a dose-dependent manner. CA strongly inhibited AChE activity at 110 μg/mL (over 80%) and at the other concentrations in a dose-dependent manner. The $IC_{50}$ value of CA for AChE activity was 86.02 μg/mL. Thus, DCB inhibits acetylcholinesterase more effectively than CA, by a factor of about 3.4.

In the AChE assay, a reaction mixture containing DCB was incubated at 20° C. in the dark for 10 min, and 10 μL of AChE solution was then added. For measuring in vitro AChE activity, the test solutions contained DCB at various concentrations, including 5, 25, 50, 100, 200, and 400 g/mL (FIGS. 13A and 13B). After AChE was added, the reaction mixture was incubated at 20° C. for 10 min, and the absorbance was measured at 405 nm.

The enzyme acetylcholinesterase is elevated in patients with certain systemic diseases, resulting in low levels of acetylcholine. The "cholinergic anti-inflammatory pathway" mediated by acetylcholine inhibits the production of inflammatory proteins, e.g., tumor necrosis factor, interleukin-1, and macrophage migration inhibitory factor. Acetylcholine regulates the levels and activities of neuropeptides and modulates both immune response and neurotransmission. By inactivating acetylcholine, AChE may enhance inflammation, and can as a marker of low-grade systemic inflammation. Since DCB inhibits acetylcholinesterase, it may act as an anti-inflammatory agent.

Example 9

The Antibiotic/Antifungal Screening of the DCB on Urine Cultures

Agar disk diffusion testing was used for antimicrobial susceptibility testing. The test provides qualitative results by categorizing susceptible, intermediate or resistant bacteria. Agar disk diffusion testing cannot distinguish bactericidal and bacteriostatic effects. Moreover, the agar disk-diffusion method is not appropriate to determine the minimum inhibitory concentration (MIC), as it is impossible to quantify the amount of the antimicrobial agent diffused into the agar medium. The advantages of this method, mainly simplicity and low cost, have contributed to its common use for the antimicrobial screening of plant extracts, essential oils, and other drugs.

The study has been performed on 47 urine samples collected from patients diagnosed with urinary tract infection (UTI), before instituting any type of therapy. Several types of pathogens were identified from the urine cultures performed: *Escherichia coli*-34 cases; *Klebsiella pneumoniae*-six cases; *Proteus mirabilis*-one case; *Staphylococcus haemolyticus*-one case; *Enterococcus faecalis*-two cases; *Candida albicans*-three cases. The susceptibility testing of the pathogens has been performed using DCB-impregnated microdisks to identify the optimal value that induces a significant inhibition of microbial culture development, compared to certified antibiotic/antifungal microdisks. The antibiogram/antifungal was performed on the Müller-Hinton (MH)/Sabouraud medium, and the results obtained using DCB-impregnated microdisks are presented in the Table 7, compared to the action of the reference microdisks.

TABLE 7

| Pathogen | Antimicrobial Microdisk | Inhibition diameter (Ø, mm] of microbial culture |
|---|---|---|
| *Escherichia coli* | Ciprofloxacin (Certified) | 28-35 |
| | 0.025 μM DCB | 0 |
| | 2.5 μM DCB | 6-8 |
| | 5.0 μM DCB | 8-14 |
| | 50 μM DCB | 29-37 |
| *Klebsiella pneumoniae* | Ciprofloxacin (Certified) | 27-34 |
| | 0.025 μM DCB | 0 |
| | 2.5 μM DCB | 5-7 |
| | 5.0 μM DCB | 8-15 |
| | 50 μM DCB | 28-36 |
| *Proteus mirabilis* | Ciprofloxacin (Certified) | 33 |
| | 0.025 μM DCB | 0 |
| | 2.5 μM DCB | 0 |
| | 5.0 μM DCB | 15 |
| | 50 μM DCB | 35 |
| *Staphylococcus haemolyticus* | Cefoxitin (Certified) | 25 |
| | 0.025 μM DCB | 0 |
| | 2.5 μM DCB | 0 |
| | 5.0 μM DCB | 11 |
| | 50 μM DCB | 27 |
| *Enterococcus faecalis* | Cefoxitin (Certified) | 23-26 |
| | 0.025 μM DCB | 0 |
| | 2.5 μM DCB | 0 |
| | 5.0 μM DCB | 12-14 |
| | 50 μM DCB | 26-29 |
| *Candida albicans* | Fluconazole (Certified) | 29-33 |
| | 0.025 μM DCB | 0 |
| | 2.5 μM DCB | 0 |
| | 5.0 μM DCB | 12-18 |
| | 50 μM DCB | 37-40 |

Table 7 shows the antibiotic/antifungal screening of the DCB on urine cultures. At low concentrations (0.025 to 2.5 μM) DCB had little or no influence on the growing pathogens. At low concentrations of DCB, e.g., 50 μM, DCB-impregnated microdisks had antimicrobial activity which was comparable to, or superior to, that of the certified microdisks. The certified microdisks are considered beneficial when the inhibition diameter of the microbial agent development is ≥26 mm for Ciprofloxacin, ≥22 mm for Cefoxitin, and >27 mm for Fluconazole. The in vitro results presented in Table 3 show that 50 μM, DCB is effective against bacteria commonly found in patients with UTI. In vivo testing is realistic because the respective high concentrations is not toxic for patients.

Several of the microorganisms listed in Table 1 are commonly found in the microbiome of the gut and/or the skin. However, several of these microorganisms opportunistic, leading to harmful overgrowth and/or infection in the event of dysbiosis in the intestinal microbiome. Antimicrobial activity of DCB against these organisms inhibits such overgrowth or infection, without harming symbiotic *Bifidobacterium* or *Lactobacillus* within the microbiome.

Example 10

The In Vitro and In Vivo Toxicity of DCB

In vitro DCB cytotoxicity: The viability of L929 cells treated for 24 hours with different concentrations of DCB was tested by the 3-(4,5-dimethylthiazol-2-yl)-2,5-diphenyltetrazolium bromide (MTT) assay. See FIG. 14. The MTT assay is commonly used for cytotoxicity, viability, and cell proliferation studies. The treatment of cells with MTT allows the assessment of oxidative metabolism and cellular response to external factors that can have a positive or negative effect on cell survival in culture. This quantitative colorimetric method is based on the reduction of the yellow-colored compound MTT to a dark blue formazan. The reduction of MTT, achieved by mitochondrial enzymes, e.g., succinate dehydrogenase, is directly proportional to the number of viable cells, being an index of cellular/mitochondrial integrity. The optical density is evaluated spectrophotometrically, resulting in a direct relationship between absorbance, dye concentration, and the number of viable and metabolically active cells.

In multi-well plates, L929 cells were plated at a cell concentration of 104 cells/$cm^2$. MTT (1 mg/ml, in a culture medium without serum) and DCB was added to each well. After 24 hours of treatment with DCB, the cell monolayer was washed with phosphate buffer solution (PBS) and a solution of MTT (1 mg/ml, in culture medium without serum) was added over it. After incubation for four hours at 37° C., the formazan crystals formed in the metabolically active viable cells were solubilized in DMSO. The resulting solution was densitometered at 550 nm, there being a direct proportional relationship between the recorded optical density and the number of metabolically active cells.

As shown in FIG. 14, the optical density (DO) at 550 nm shows little or no change at a DCB concentration of 0.1 mM to 5 mM, relative to a control which is not exposed to DCB. The optical density at 550 nm, corresponding to yellow MTT, shows relatively minor changes at a DCB concentration of up to 10 mM, relative to control. All tested DCB concentrations show much less impact on MTT concentration, and thus cell viability, than a negative control treated with 5% aqueous DMSO.

In vivo DCB toxicity: The laboratory animals and the experimental protocol for determining acute, subchronic and chronic toxicity were established in accordance with the Organization for Economic Co-operation and Development (OECD) Guidelines for Testing of Chemicals. The toxicodynamic experiment was performed on groups of 10 BALB/c mice, eight weeks old, with an average weight of 25 g, the number of females and males being equally distributed (five for each group), which were administered different doses of DCB, at various intervals, as follows:

(i) for the acute experiment (at 24 hours):
  (a) per os (p.o.), by oral gavage, five different doses of DCB in distilled water: 5 mg/kg body weight (b.w.), 50 mg/kg b.w., 300 mg/kg b.w., 2000 mg/kg b.w. and 5000 mg/kg b.w.;
  (b) intra-peritoneal (i.p), a single dose of DCB, in saline: 50 mg/kg b.w.;
(ii) for the subacute experiment (lasting 28 days), three different daily doses of DCB in drinking water: 50 mg/kg b.w., 300 mg/kg b.w. and 1000 mg/kg b.w.;
(iii) for the chronic experiment (lasting 90 days), three different daily doses of DCB in drinking water: 50 mg/kg b.w., 300 mg/kg b.w. and 1000 mg/kg b.w.

Throughout the duration of the experiment, the condition of the animals was monitored daily, at the same hour every day (during morning). Also, the animals were maintained in standard conditions of temperature, humidity, and lighting. Food and water were administered ad libitum.

Standard Conditions Include:

A 14-hour light/10-hour dark cycle or 12 light/12 dark cycle;

A temperature of 65-75° F. (~18-23° C.); and

A humidity of 40-60%.

The control mice were monitored and maintained under the same conditions, only that instead of the DCB they received:

(i) for the acute experiment: (a) distilled water, p.o., by oral gavage and (b) saline, i.p., respectively;
(ii) for the subacute experiment and for the chronic one: only the drinking water normally consumed.

The experimental protocol was applied in accordance with the European Convention for the Protection of Vertebrate Animals used for experimental and other scientific purposes.

Depending on the duration of the experiments, the animals were sacrificed after 24 hours (acute), 28 days (subchronic) and 90 days (chronic), respectively, by euthanasia under general anesthesia with an injectable mixture of Ketamine/Xylazine, administered intraperitoneally, for the purpose of harvesting internal organs (brain, liver, myocardium, pancreas, lung, kidney, stomach, intestine). From the point of view of acute toxicity, considering the median lethal dose ($LD_{50}$) value (>5000 mg/kg b.w.) upon p.o. administration in mice, DCB belong to the class of substances with very low toxicity: Category V, practically non-toxic (OECD, 2012). From a histopathological point of view, in the case of the acute, subchronic and chronic experiments, normal aspects were highlighted for all internal organs analyzed.

Example 11

DCB Levels in Mouse Feces

DCB levels in feces from a group of 10 BALB/c mice, eight weeks old, with an average weight of 25 g, were monitored over a seven day period. The number of females and males was equally distributed with the group. which were administered a daily dose of DCB corresponding to 150 ppm boron/kg b.w., in drinking water.

As seen in FIG. 15, during the first two days of DCB administration, boron concentration in the feces is low, i.e., >25 ppm. Between days three and five of DCB administration, boron concentration in the feces gradually increases to ~120 ppm. After day five, boron concentration in the feces is roughly constant at between 100 ppm and 130 ppm.

The low levels of boron in the feces in the first two days after administration of DCB begins indicates that boron is not excreted. Since DCB is not digested and is not utilized in human cells, it is believed that DCB is incorporated into bacterial cells in the microbiome. In the microbiome, DCB is metabolized and borate is released from chlorogenic acid. Borate is then incorporated into the signaling molecule AI-2. Boron is used in the microbiome to maintain bacterial cell wall structure, and complexes with bacterial glycoproteins involved with membrane synthesis. Thus, bacteria is incorporated into, and metabolized by bacteria in the microbiome. As the microbiome becomes saturated with borate, DCB is no longer metabolized by the bacteria therein. Since the human body does not metabolize DCB, the amount of boron-containing DCB in the feces increases as DCB is excreted.

Seeing boron (as DCB) in the feces shows that, after five to seven days of administration, microbiota and mucus gel layer are saturated with boron. Subsequently, since it is not needed anymore in the microbiota, DCB remains intact and is excreted. DCB remains intact because the borate ester of chlorogenic acid cannot be metabolized in human cells. DCB is metabolized only if cleavage of the borate group occurs.

After the microbiota and the mucus gel layer in the gut have been saturated with boron, then DCB is not digested, and remains intact in the colon. The undigested borate ester acts in the colon as an antioxidant, an anti-inflammatory agent, and an antibacterial agent. As shown in FIGS. 12A and 12B, the antioxidant activity of DCB is approximately six times greater than that of chlorogenic acid. As shown in FIGS. 13A and 13B, the antioxidant activity of DCB as an AChE inhibitor is significantly greater than that of chlorogenic acid. As seen in Table 3, DCB is an effective agent against various undesirable bacterial infections.

Generally, bacteria using boron for communication with the AI-2 molecule include Gram-positive and Gram-negative bacteria. Lactic bacteria also need boron for their growth, so probably lactic acid may be involved in the DCB dissociation in the microbiome. Boron which does not enter the microbiome is not absorbed in the colon; it is excreted through feces. The human/animal body does not need boron, only the microbiota needs born for healthy symbiosis with the host body. In humans/animals, there is no metabolic pathway to use boron.

Example 12

Dietary DCB supplementation improved diarrhea index and increased AI-2B in a rat model of castor oil-induced diarrhea.

In vivo DCB-rich natural extract feeding. In vivo DCB-rich natural extract feeding was carried out on three groups of six month old male Wistar rats, each of four animals, with an average weight of 290±10 g, as follows:

Group 1 (Reference)→ rats fed the normal diet;

Group 2 (castor oil-induced diarrhea)→ rats with castor oil-induced diarrhea;

Group 3 (DCB)→ rats fed with DCB-rich green coffee bean extract (as 15 ppm B) intake five days after diarrhea appeared.

Throughout the experiment, animals were kept under observation in individual cages under standard conditions of temperature, humidity, and lighting (12-hour light/dark cycle). Food and water was administered ad libitum. The next seven days, fecal matter was collected from each rat and food was resupplied at four days. The experimental data are shown in FIGS. 17A and 17B. It is observed that the AI-2B values in Group 2 with induced diarrhea are very low at an average of 1.4 μM AI-2B (FIG. 17A), which corresponds to the increased diarrhea index of 21.8 (FIG. 17B). The diet with DCB-rich green coffee bean extract five days after the onset of diarrhea leads to a consistent concentration of AI-2B in the feces of 45.3 μM and a near-normal diarrhea index of 1.5.

AI-2B analysis from saliva, colonic mucus gel layer, and stool samples. Saliva, colonic mucus and stool samples obtained from the mice were stirred for 24 hours in 1 mL of an acetonitrile-water (1:1, v/v) mixture. After a day, the samples were homogenized using a Heidolph Silent Crusher, and 10 μL of an ultrapure 1 mg/mL fructose solution were added over each sample. The column used for the method development was the Waters Atlantis HILIC Silica (2.1×150 mm, 3 m) eluting with solvent A (0.1% acetic acid in 10 mM ammonium acetate aqueous solution) and solvent B (acetonitrile). The solvent was used in isocratic conditions, as follows: 0-4 minutes, 20% A. The flow rate of the mobile phase was set at 0.25 mL/min. The column temperature was equilibrated to 30° C. The injection volume was 5 μL. The QDa detector was employed and set to negative mode at 0.8 kV for the capillary, 25 V for the cone voltage and 400° C. for the capillary. The mass range was set between m/z 100-500 for the spectrum. For quantification purposes, the SIR for m/z 337 was used.

Ultrapure fructose was reacted with AI-2B (FIG. 18A) to form a new compound (AI-2B-fructose) (FIG. 18B). AI-2B (98% purity, HPLC) solution (0.3 mg/mL, dissolved in ultrapure water) was purchased from Glixx Laboratories, Inc. (MA, USA). The working standard solutions with a range of 10-14000 ng/mL were obtained through diluting the stock solution of AI-2B. The HPLC-MS method was validated in terms of linearity, limit of detection (LOD), limit of quantification (LOQ), accuracy and precision following the International Conference on Harmonization (ICH) guidelines. For linearity validation, nine concentration levels (10-14000 ng/mL) were tested following the method stated above and calibration curves were constructed by plotting peak area versus concentration.

Under the conditions described above, AI-2B had an m/z of 192, and AI-2B-fructose had an m/z of 336.

The LOD and LOQ were defined as the concentration that produced a signal-to-noise (S/N) ratio of 5 and a S/N ratio of 15, respectively. The assay was linear in the concentration range of 1-1000 ng/mL (coefficient of determination, $R^2$=0.999) and had a lower LOQ of 0.58 ng/mL.

Experiments and Results. The diarrhea index was calculated by the loose stool rate×the loose stool grade. Under the castor oil-induced diarrhea model, castor oil was administered as a single dose of 20 mL/kg body weight by using oral gavage. A DCB-rich natural extract is a natural supplement that protects against external agents that reduce the number of commensal bacteria in the gut, and lead to increased levels of AI-2B in the gut. AI-2B may be a control biomarker for dysbiosis. In general, dysbiosis leads to a decrease in the number of commensal bacteria and an increase in pathological bacteria that cause diarrhea. The use of DCB-rich natural extract in the relief of diarrhea increases the level of AI-2B in feces and reduces dysbiosis.

Example 13

Uses of DCB-rich natural extract in dentistry: a pilot clinical study on the effect of a mouthwash containing DCB-rich decaffeinated GCBE on the oral health Experimental Design A randomized, double-blind, placebo-controlled test of daily use of a DCB-rich natural extract-containing mouthwash was made. A group of 20 patients with chronic marginal periodontitis were tested over a period of three months. They were divided into two study groups:

Group 1 (control group), in which only the mechanical treatment was performed; and Group 2, a group that in addition to the mechanical treatment received a mouthwash with DCB extract natural.

All patients also received instructions on oral hygiene and mouthwash use. During the first examination session, a complete examination of the soft and hard tissues was performed to record the condition of the oral mucosa, so that any changes during the study could be identified, assessing whether these changes could be related to mouthwash. For each patient, one tooth per sextant was analyzed, including the first maxillary and mandibular molars and an upper and lower central incisor. If these teeth had crowns or were absent, for the lateral area a premolar and another incisor was used. First, the dental plaque was revealed by applying a bullet soaked with a plaque disclosing agent on the upper buccal side and lower lingual sides. The following clinical parameters were used to assess the degree of periodontal health at each consultation:

the Silness and Löe (S&L) plaque index was used to assess the degree of oral hygiene, in which the presence of dental plaque was graded from 0 (absence of dental plaque) to 3 (the presence of plaque on more than half of the buccal side of the tooth);

the calculus index, with values from 0 (absence of calculus) to 3 (calculus covering over ⅔ of the tooth)

probing depth or periodontometry, measuring the mesial and distal periodontal sulcus for each tooth analyzed in the six sextants, and the bleeding on probing index, assigning the value 0 for a lack of bleeding or 1 for the presence of bleeding, regardless of bleeding severity. All these examinations were repeated at the following sessions at one month and three months, respectively. After the initial examination, each subject received a complete prophylactic treatment, which included ultrasound scaling, airflow, and professional brushing. Shortly afterwards, the subjects received, depending on the group, a mouthwash, being instructed to perform their tooth brushing as usual. All participants were instructed on the use of mouthwash, to use it in the morning and evening, at the end of the routine of teeth brushing by rinsing for 30-60 seconds. The recommended amount for a rinse was 20 mL (about two tablespoons). They were instructed not to swallow the product and to avoid eating and drinking for 10-15 minutes after cleaning, to allow the product to continue to act. The analysis of AI-2B in saliva was performed at the end of the study both for the control and for the group treated with DCB-rich natural extract.

Results and Discussions. The analysis of the S&L plaque index on the mandibular molars showed a progressive reduction of the dental plaque on the group that used DCB-rich natural extract mouthwash. The global calculus index showed the same pattern in all groups, with a decrease in the second stage and some increase in the third stage. The bleeding on probing also showed promising results. There was a progressive decrease in values in Group 2, the group using DCB-rich natural extract mouthwash.

The level of salivary AI-2B in Group 1 was very low, around 1.5 μM, while Group 2 has, after finishing the treatment with mouthwash containing DCB-rich natural extract (average 8% DCB-rich natural extract in pure distilled water) increased to 35 μM (FIG. 19).

Example 14

Dysbiosis Index (DI) and AI-2B Correlations for Patients with Long-Term Antibiotic Therapy Experimental Design.

Number of participants:

Group 1: 10 healthy subjects (control);

Group 2: 10 subjects with standard intravenous antibiotic treatment (Sulcef);

Group 3: 10 subjects with standard intravenous antibiotic treatment and supplemented with DCB-rich standardized GCBE (three capsules/day—1 mg of B, cca. 65 mg of DCB) during the 30 days.

Inclusion criteria:

(i) male or female patients, 40-60 years age;

(ii) 1:1 gender ratio selection, approximately the same age per pair;

(iii) BMI range 17-27 (normal, overweight, but not obese);

(iv) normal or minor hypertension (<140/80-90 mmHg);

(v) informed consent obtained at selection.

Exclusion criteria:

(i) refusal to participate or to sign the informed consent;

(ii) proven *Clostridium difficile* co-infection;

(iii) other infection excepting the respiratory tract;

(iv) known IBD or other diseases that may significantly influence gut microbiota.

Primary outcome measures:

(i) significant differences assessed by questionnaires regarding quality of the stool and general significant symptoms associated with gut dysbiosis;

(ii) level of AI-2B in the stools depending on DI [derived from a log-normal distribution by assigning estimated portions of the distribution to different values on a scale set from 0 to 5.

Secondary outcome measure:

significant microscopy changes, if colon biopsy is going to be performed in any patient (only when necessary for other pathologies or indications).

For the pilot study, DCB has been prepared as a natural green coffee bean extract (cca. 6.5% DCB) at a standard concentration of 1000 ppm of boron.

FIG. 20 shows that the dysbiosis index DI of Group 2, treated with antibiotics, shows a strong increase, and there is a corresponding decrease in the level of AI-2B, which means that commensal bacteria are reduced in number. The group supplemented with the DCB-rich natural extract, Group 3, shows a reduction of the DI, relative to Group 2, and a significant increase in the level of AI-2B. Supplementation with DCB-rich natural extracts can prevent dysbiosis induced by antibiotic treatment, by increasing AI-2B in the intestinal microbiota. AI-2B is a potential marker of intestinal dysbiosis.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method of producing an extract comprising a chlorogenic acid and a borate diester of chlorogenic acid, wherein the method comprises:

i. extracting green coffee beans in a solvent comprising water or a mixture of water and an organic solvent to produce an aqueous reaction mixture; and ii. producing the extract comprising the chlorogenic acid and the borate diester by a step selected from the group consisting of:

freeze-drying the aqueous reaction mixture; and evaporating water from the aqueous reaction mixture;

wherein the method further comprises adding boric acid to the aqueous reaction mixture to provide the extract with an increased content of the borate diester.

2. A method of producing an composition comprising a borate ester of chlorogenic acid, wherein the method comprises:

i. reacting a chlorogenic acid with boric acid in a solvent comprising water or a mixture of water and an organic solvent to produce an aqueous reaction mixture; and ii. producing the extract comprising the borate ester of chlorogenic acid by a step selected from the group consisting of:

freeze-drying the aqueous reaction mixture; and evaporating water from the aqueous reaction mixture.

3. The method according to claim 2, wherein:

the reacting step comprises reacting a green coffee bean extract comprising the chlorogenic acid with the boric acid in superheated water at a pressure of 1.5 bar to 85 bar and a temperature of 110° C. to 300° C.; and the aqueous reaction mixture is freeze-dried.

4. The method according to claim 2, wherein:

the reacting step comprises reacting the chlorogenic acid with the boric acid in superheated water at a pressure of 1.5 bar to 85 bar and a temperature of 110° C. to 300° C.; and the aqueous reaction mixture is freeze-dried.

5. The method according to claim 4, wherein the reacting step is carried out at a pressure of 4 bar to 25 bar and a temperature of 125° C. to 225° C.

6. A method of treating boron insufficiency of a microbiome in a subject in need thereof, comprising administering an effective amount of a borate ester of chlorogenic acid to the subject, wherein the borate ester has a structure of formula (I) or a structure of formula (II), where X is hydrogen or a pharmaceutically acceptable cation:

(I)

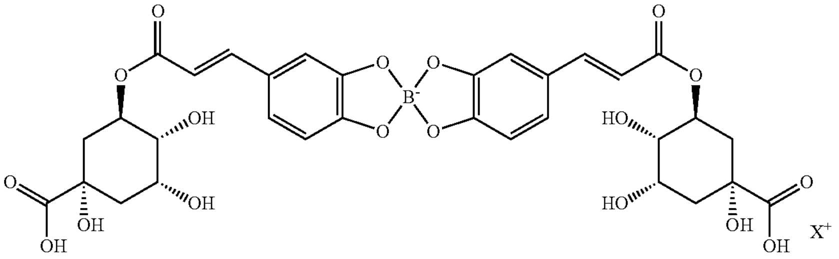

(II)

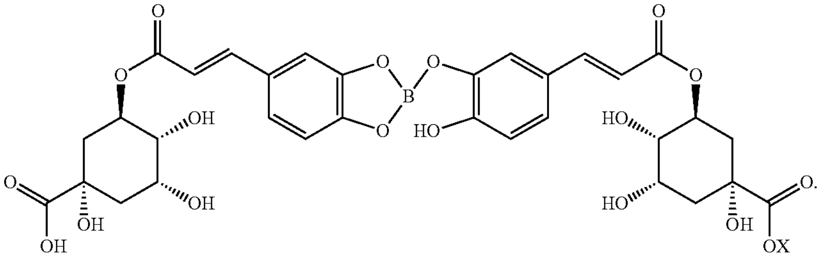

7. The method of claim 6, wherein the microbiome comprises microorganisms found in a lower gastrointestinal tract, an oral mucosal surface, a skin surface, or a vaginal surface.

8. The method of claim 7, wherein the microbiome comprises the microorganisms found in the lower gastrointestinal tract or the vaginal surface, and the borate ester is administered to the subject in a suppository.

9. The method of claim 7, wherein the microbiome comprises the microorganisms found in the lower gastrointestinal tract, and administering the borate ester relieves diarrhea caused by dysbiosis of the microbiome.

10. The method of claim 7, wherein the microbiome comprises the microorganisms found in the oral mucosal surface, and the borate ester is administered to the subject in a mouthwash, a toothpaste, a sublingual tablet, a buccal tablet, or a candy.

11. The method of claim 7, wherein the microbiome comprises the microorganisms found in the skin surface, and the borate ester is administered to the subject in a topical cream or ointment.

12. The method of claim 6, wherein administering the borate ester to the subject improves microbiome health by:

a. alleviating boron insufficiency in a beneficial microorganism of the genus *Bifidobacterium*, a beneficial microorganism of the genus *Lactobacillus*, or a mixture thereof;

b. inhibiting the growth of a pathogenic microorganism of the species *Escherichia coli*, a pathogenic microorganism of the species *Klebsiella pneumoniae*, a pathogenic microorganism of the species *Proteus mirabilis*, a pathogenic microorganism of the species *Staphylococcus haemolyticus*, a pathogenic microorganism of the species *Enterococcus faecalis*, a pathogenic microorganism of the species *Candida albicans*, or a mixture thereof; or c. both (a) and (b).

13. The method of claim 6, wherein the method further comprises administering a probiotic bacteria to the subject, wherein the probiotic bacteria is:

a bacteria from a phylum Bacteroidetes, Firmicutes, or a combination thereof;

a bacteria from a genus *Lactobacillus, Bifidobacterium, Leuconostoc, Pediococcus, Bacteroides, Akkermansia, Streptococcus*, and *Bacillus*, or a combination thereof, a bacteria from a species *Leuconostoc mesenteroides, Lactobacillus plantarum, Pediococcus pentosaceus, Lactobacillus brevis, Leuconostoc citreum, Leuconostoc argentinum, Lactobacillus paraplantarum, Lactobacillus coryniformis, Leuconostoc mesenteroides, Lactobacillus lactis, Lactobacillus fermentum, Lactobacillus acidophilus, Bifidobacterium bifidum, Lacto-*

*bacillus delbrueckii* subsp. *bulgaricus, Lactobacillus helveticus, Lactobacillus* kefiranofaciens, or a combination thereof; or a combination thereof.

14. The method of claim 6, wherein administering the borate ester improves the health of the subject by at least one of:

ameliorating metabolic diseases;
ameliorating psychiatric diseases;
ameliorating dysbiosis of gut and oral microbiota;
ameliorating gut mucus layer degradation;
ameliorating intestinal barrier hyperpermeability;
attenuating brain ischemic injury in patients at risk of ischemic stroke;
ameliorating atherosclerosis;
increasing neurotransmitter levels;
ameliorating hormone imbalance;
assisting in obesity management; and
slowing the aging process.

15. A method of treating dysbiosis of a microbiome in a patient, comprising:

obtaining a sample comprising bacteria from the microbiome of the patient, wherein:

the microbiome is in an oral mucosa, and the sample comprises a sample of saliva or an oral mucus gel layer; or the microbiome is in a colon, and the sample comprises a stool sample or a sample of a colonic mucus gel layer;

detecting a level of furanosyl borate diester in the sample, where the detected level of furanosyl borate diester is less than a target value; and increasing the level of furanosyl borate diester in the microbiome of the patient by administering a composition to the patient;

wherein the composition is produced by a process comprising:

i. reacting a green coffee bean extract comprising a chlorogenic acid with boric acid in a solvent comprising water or a mixture of water and an organic solvent to produce an aqueous reaction mixture, wherein boric acid is added to the aqueous reaction mixture to provide the green coffee bean extract with an increased content of the borate diester; and ii. freeze-drying the aqueous reaction mixture to produce the composition comprising the borate ester of chlorogenic acid.

16. The method of claim 15, wherein the detecting step comprises:

converting furanosyl borate diester (AI-2B) to a fructose adduct AI-2B-fructose by reacting the sample with fructose;

detecting a level of AI-2B-fructose in the sample.

17. The method according to claim 2, wherein:

the reacting step comprises reacting the chlorogenic acid with boric acid in the mixture of water and the organic solvent to produce the aqueous reaction mixture; and the method further comprises evaporating the organic solvent from the aqueous reaction mixture after the completion of the reacting step.

18. The method according to claim 17, wherein:

the mixture of water and the organic solvent is aqueous acetonitrile.

19. The method according to claim 18, wherein:

the reacting step comprises reacting the chlorogenic acid or a green coffee bean extract comprising the chlorogenic acid with the boric acid in the aqueous acetonitrile at a temperature of 40° C. to 80° C.

* * * * *